(12) United States Patent
Webster et al.

(10) Patent No.: US 11,253,234 B2
(45) Date of Patent: Feb. 22, 2022

(54) USER FRIENDLY VAGINAL TEMPERATURE SENSOR SYSTEM

(71) Applicant: Prima-Temp, Inc., Boulder, CO (US)

(72) Inventors: Wade Webster, Woodinville, WA (US);
Richard Pollack, Boulder, CO (US);
Eric Harden, Arvada, CO (US);
Calder Daenzer, Boulder, CO (US);
James Frank Kasic, II, Boulder, CO (US)

(73) Assignee: Prima-Temp, Inc., Boulder, CO (US)

( * ) Notice: Subject to any disclaimer, the term of this patent is extended or adjusted under 35 U.S.C. 154(b) by 0 days.

(21) Appl. No.: 17/075,608

(22) Filed: Oct. 20, 2020

(65) Prior Publication Data

US 2021/0030403 A1 Feb. 4, 2021

Related U.S. Application Data

(63) Continuation of application No. 16/628,197, filed as application No. PCT/US2018/041908 on Jul. 12, 2018, now Pat. No. 10,828,015.

(51) Int. Cl.
*A61B 10/00* (2006.01)
*A61B 5/00* (2006.01)

(52) U.S. Cl.
CPC ........ *A61B 10/0012* (2013.01); *A61B 5/0008* (2013.01); *A61B 5/4337* (2013.01);
(Continued)

(58) Field of Classification Search
CPC ..... A61B 5/7278; A61B 5/0008; A61B 5/742; A61B 5/01; A61B 5/431; A61B 5/14546;
(Continued)

(56) References Cited

U.S. PATENT DOCUMENTS

| 4,151,831 A | 5/1979 | Lester |
| 4,888,074 A | 12/1989 | Pocknell |

(Continued)

FOREIGN PATENT DOCUMENTS

| DE | 3342251 A1 | 5/1985 |
| DE | 3802479 A1 | 10/1989 |

(Continued)

OTHER PUBLICATIONS

Wikipedia, Artificial neural network, https://en.wikipedia.org/wiki/Artificial_neural_network, Jun. 12, 2018, 40 Pages.

(Continued)

*Primary Examiner* — Hoi C Lau
(74) *Attorney, Agent, or Firm* — Santangelo Law Offices, P.C.

(57) ABSTRACT

Embodiments of a vaginal temperature sensing apparatus, a visually sense-able battery power-on indicator (16), manufacturing with cure temperatures that protect a battery, substantially error-free, user-initiated device activation componentry (30) to start battery power, and a timer to automatically terminate flow of battery power. Data can, by an automatic data transform recalculator (138) with body temperature dips in transformed and recalculated diurnal high body temperatures, predict an ovulation event and provide an indication through a zenith based ovulation indicator (106). Systems can include neural network based artificial intelligence to automatically self-improve by using historical or even other, multi user data and user input and improve its indication result.

20 Claims, 13 Drawing Sheets

(52) U.S. Cl.
CPC .......... *A61B 5/6847* (2013.01); *A61B 5/7275* (2013.01); *A61B 5/74* (2013.01); *A61B 2010/0019* (2013.01); *A61B 2010/0029* (2013.01); *A61B 2560/0214* (2013.01); *A61B 2562/12* (2013.01)

(58) Field of Classification Search
CPC ..... A61B 5/4306; A61B 5/024; A61B 5/0444; A61B 10/0012; A61B 10/00; G16H 40/67; G16H 40/63
See application file for complete search history.

(56) References Cited

U.S. PATENT DOCUMENTS

| | | | |
|---|---|---|---|
| 5,406,961 A | | 4/1995 | Artal |
| 6,447,448 B1 | | 9/2002 | Ishikawa et al. |
| 6,939,569 B1 | | 9/2005 | Green et al. |
| 8,496,597 B2 | | 7/2013 | James et al. |
| D703,319 S | | 4/2014 | Ziegner |
| 8,715,204 B2 | | 5/2014 | Webster et al. |
| 8,930,147 B2 | | 1/2015 | Pollack et al. |
| 9,155,522 B2 | | 10/2015 | James et al. |
| 9,155,523 B2 | | 10/2015 | James et al. |
| 9,314,227 B2 | | 4/2016 | Runkewitz et al. |
| 10,314,540 B2 | | 6/2019 | Fougere et al. |
| 10,383,604 B2 | | 8/2019 | Pardey |
| D889,649 S | * | 7/2020 | Beer ............................ D24/141 |
| D896,958 S | * | 9/2020 | Beer ............................ D24/141 |
| D896,959 S | * | 9/2020 | Beer ............................ D24/141 |
| D897,530 S | * | 9/2020 | Beer ............................ D24/141 |
| D899,593 S | * | 10/2020 | Beer ............................ D24/141 |
| 10,828,015 B2 | * | 11/2020 | Webster ............... A61B 5/4337 |
| D922,575 S | * | 6/2021 | Beer ............................ D24/141 |
| 2005/0055731 A1 | * | 3/2005 | Burnett ................... H04R 5/04 725/141 |
| 2005/0288737 A1 | | 12/2005 | Feliss et al. |
| 2007/0150025 A1 | | 6/2007 | Dilorenzo |
| 2009/0221882 A1 | | 9/2009 | Furman |
| 2009/0234200 A1 | | 9/2009 | Husheer |
| 2009/0270948 A1 | | 10/2009 | Nghiem |
| 2009/0296742 A1 | | 12/2009 | Sicurello et al. |
| 2009/0326410 A1 | * | 12/2009 | James ..................... G16H 40/67 600/551 |
| 2010/0004707 A1 | | 1/2010 | Hochman et al. |
| 2010/0036208 A1 | | 2/2010 | Koh et al. |
| 2010/0274105 A1 | * | 10/2010 | Rosenshein ......... A61M 5/1723 600/301 |
| 2012/0016258 A1 | | 1/2012 | Webster et al. |
| 2012/0053534 A1 | * | 3/2012 | Mahashabde ........ A61K 9/0036 604/285 |
| 2012/0238900 A1 | | 9/2012 | Rechberg |
| 2012/0283581 A1 | | 11/2012 | Olde et al. |
| 2013/0053657 A1 | * | 2/2013 | Ziarno ................ A61B 5/14539 600/304 |
| 2013/0131541 A1 | | 5/2013 | Tsai et al. |
| 2013/0137940 A1 | * | 5/2013 | Schafer .................. G16Z 99/00 600/301 |
| 2013/0225922 A1 | | 8/2013 | Schentag et al. |
| 2013/0237771 A1 | * | 9/2013 | Runkewitz ......... A61B 10/0012 600/301 |
| 2014/0104059 A1 | | 4/2014 | Tran |
| 2014/0213927 A1 | * | 7/2014 | Webster .................. A61B 5/01 600/549 |
| 2014/0296834 A1 | * | 10/2014 | Moss .................... A61K 9/0036 604/515 |
| 2015/0044398 A1 | | 2/2015 | Oguri et al. |
| 2015/0250457 A1 | | 9/2015 | Yamtao |
| 2016/0030011 A1 | | 2/2016 | James et al. |
| 2016/0074276 A1 | | 3/2016 | Scheuring et al. |
| 2016/0143630 A1 | * | 5/2016 | Pardey ................. A61B 5/0008 600/549 |
| 2016/0213354 A1 | | 7/2016 | Levin |
| 2016/0296210 A1 | | 10/2016 | Matsushima |
| 2017/0079587 A1 | * | 3/2017 | Fougere ............. A61B 5/14507 |
| 2018/0035954 A1 | | 2/2018 | Swezey |
| 2018/0214028 A1 | | 8/2018 | Zhang |
| 2018/0228474 A1 | | 8/2018 | Suzuki |
| 2018/0271500 A1 | | 9/2018 | James et al. |
| 2019/0357891 A1 | | 11/2019 | Pardey |
| 2020/0000441 A1 | | 1/2020 | Lafon |
| 2020/0113470 A1 | * | 4/2020 | Friedman ............... A61B 5/344 |
| 2020/0297328 A1 | * | 9/2020 | Webster ............... A61B 5/4337 |
| 2021/0030403 A1 | * | 2/2021 | Webster ................... A61B 5/01 |

FOREIGN PATENT DOCUMENTS

| | | |
|---|---|---|
| DE | 19943456 A1 | 4/2001 |
| DE | 10345282 B3 | 4/2005 |
| DE | 19943456 B4 | 10/2005 |
| EP | 0424102 B1 | 12/1998 |
| EP | 1636594 A2 | 3/2006 |
| EP | 2061380 B1 | 5/2011 |
| EP | 2567680 A1 | 3/2013 |
| EP | 1579007 B1 | 5/2015 |
| RU | 2241375 C1 | 12/2004 |
| WO | 2004058999 A2 | 7/2004 |
| WO | 2007059761 A2 | 5/2007 |
| WO | 2008029130 A2 | 3/2008 |
| WO | 2012125650 A1 | 9/2012 |
| WO | 2015044398 A1 | 4/2015 |
| WO | 2016120402 A1 | 8/2016 |
| WO | 2018023037 A1 | 2/2018 |
| WO | 2019199819 A1 | 10/2019 |
| WO | 2020013830 A1 | 10/2020 |

OTHER PUBLICATIONS

CNET, Youtube, Fertility trackers at CES 2015, https:/lwww.youtube.com/watch?v=cSjFeKPOsUw, Jan. 7, 2015, 4 pages.
U.S. Appl. No. 13/021,806, filed Feb. 7, 2011, entitled "Multi-Sensor Patch and System ".
U.S. Appl. No. 13/182,565, filed Jul. 14, 2011, entitled "Wireless Vaginal Sensor Probe".
U.S. Appl. No. 14/253,560, filed Apr. 15, 2014, entitled "Physiologic Change Sensor Probe".
U.S. Appl. No. 61/364,034, filed Jul. 14, 2010, entitled "Wireless Vaginal Sensor Probe".
U.S. Appl. No. 62/287,806, filed Jan. 27, 2016, entitled "User-Enhanced Body Temperature Sensing Device".
Liu et al., Materials for Lithium-Ion Battery Safety, Science Advances I Review, Jun. 22, 2018, 12 pages.
Trademark Application No. 011727633, filed Apr. 10, 2013, OvulaRing Individual Word Mark, Aug. 12, 2013, 7 pages.
Pessary, Define Pessary at Dictionary.com, (http://www.dictionary.com/), May 3, 2018, 5 pages.
Regidor et al., Identification and prediction of the fertile window with a new web-based medical device using a vaginal biosensor for measuring the circadian and circamensual core body temperature, Gynecological Endocrinology, Oct. 28, 2017, 6 pages.
Shop—OvulaRing, https://www.ovularing.com/shop.html, Jul. 9, 2018, 2 pages.
Patent Cooperation Treaty, PCT/US2018/041908, International Search Report, dated Nov. 15, 2018, 6 pages.
Translucent, Define Translucent, Dictionary.com, http://www.dictionary.com/browse/translucent?s=t, May 3, 2018, 6 pages.
Transparent, Define Transparent, Dictionary.com, http://www.dictionary.com/browse/transparent, May 3, 2018, 6 pages.
The VivoSensMedical Leipzig GmbH article, https://www.ovularing.com/, 1 page.
Machine Translated version of DE 10345282, Machine translation was provided by espace.net, Dec. 17, 2013, 6 pages.
Rodrigues, Intra-Body Sensor for Vaginal Temperature Monitoring. Open Access; Sensors ISSN: 1424-8220; 2009. 12 pages.
Patent Cooperation Treaty, PCT/US2018/041908, Written Opinion of the International Searching Authority, dated Nov. 15, 2018, 14 pages.
International Patent Application No. PCT/US2018/041908 filed Jul. 12, 2018.

(56) References Cited

OTHER PUBLICATIONS

U.S. Appl. No. 16/628,197, filed Jan. 2, 2020. First Named Inventor: Webster.
Russian Patent Application No. 2021103513(007607), Search Report dated Aug. 20, 2021. 2 pages.

* cited by examiner

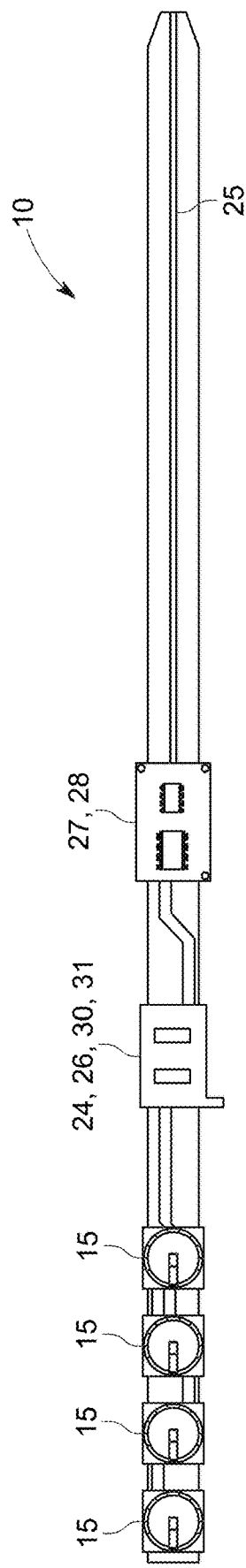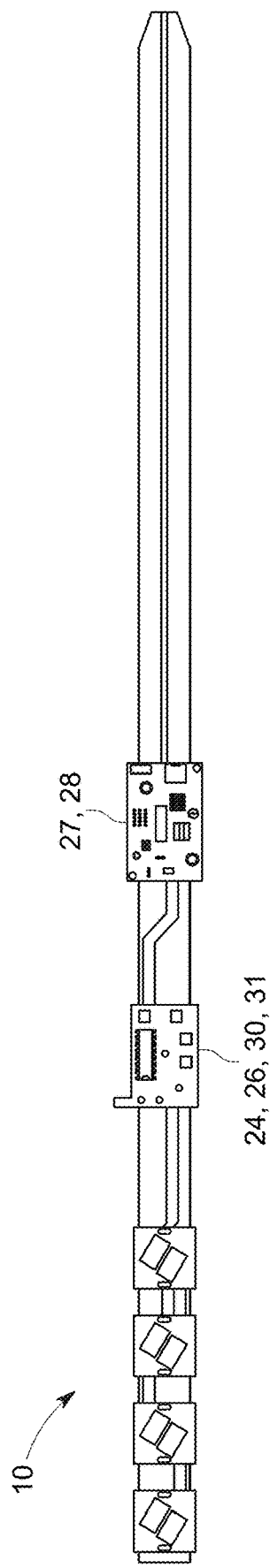

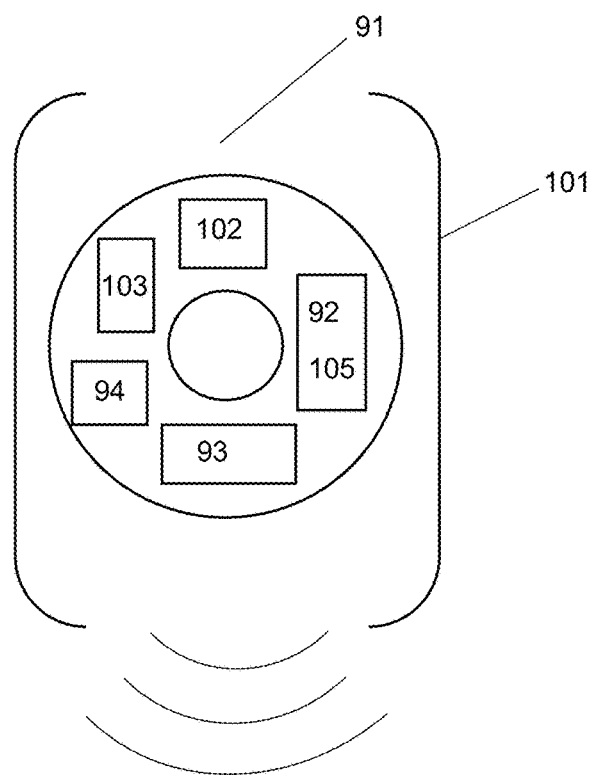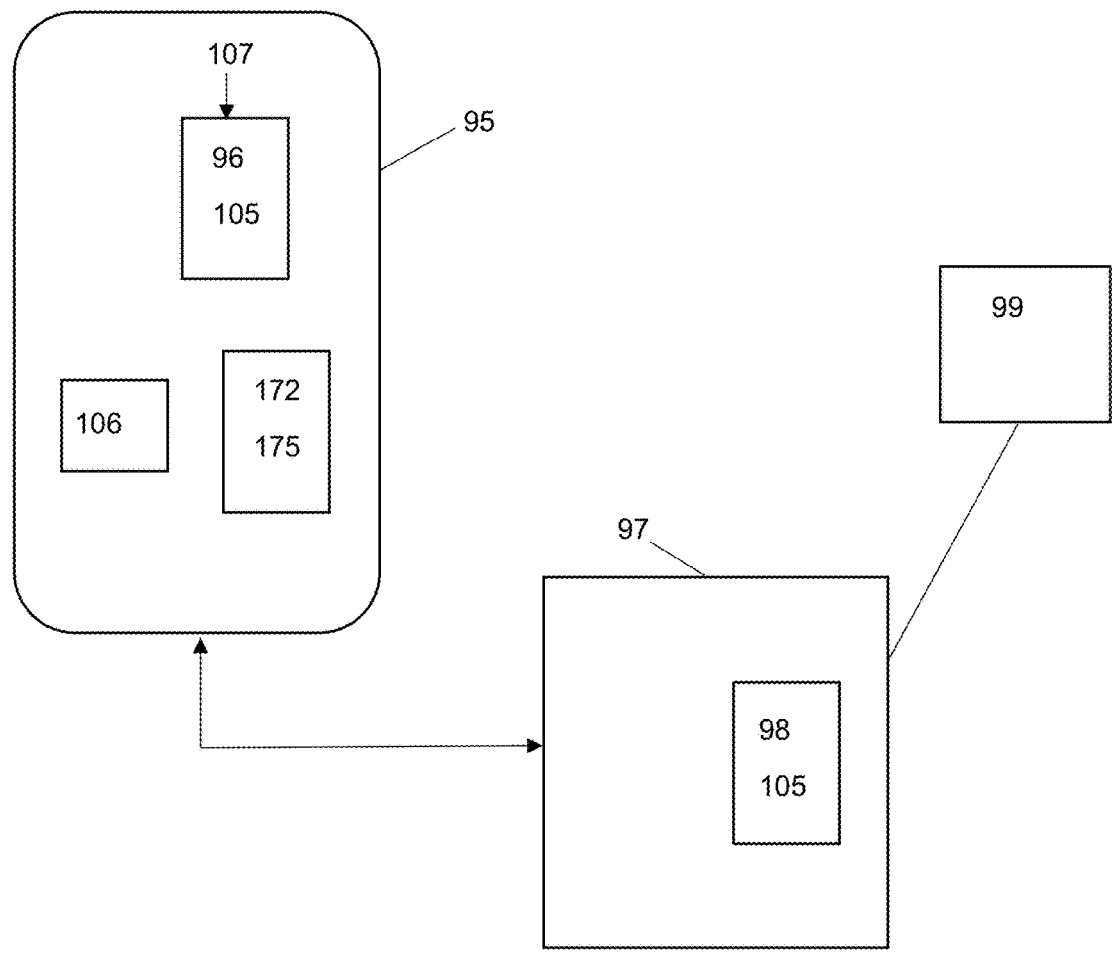
FIG. 17

USER FRIENDLY VAGINAL TEMPERATURE SENSOR SYSTEM

This application is a continuation application of U.S. patent application Ser. No. 16/628,197, filed Jan. 2, 2020, which is the United States National Phase of international PCT application number PCT/US18/041908, filed 12 Jul. 2018. Said applications and any priority cases are hereby incorporated by reference in their entirety herein.

TECHNICAL FIELD

This invention relates to devices and processes for sensing and using body temperature to predict ovulation events for a user.

BACKGROUND

As has been well known for years, a woman typically may monitor and record her body basal temperature on a daily basis by way of inserting a thermometer into her vagina and recording her temperature. As a result of this perhaps complex daily procedure, a woman may be likely to forego recording her more accurate core temperature obtained vaginally and instead may keep track of her oral temperature. Furthermore, although temperature monitoring may have been used for years to help determine a fertile phase of a woman, the pattern recognition and relationship of temperature variation may not have been practically achieved such as due perhaps to the lack of frequent temperature monitoring and statistical analysis of baseline core body temperature. Other methods of obtaining a woman's body temperature over time may include frequent temperature measured orally or from her axilla, however there may be accuracy issues, and frequent insertion of a wired rectal probe or vaginal probe may be inconvenient and uncomfortable. Hence there has long been a need for improved methods, systems, and apparatuses for obtaining an accurate basal temperature vaginally while reducing inconvenience and discomfort; in-situ vaginal temperature sensing was conceived in response to such disadvantages.

Indeed, in-situ vaginal temperature sensing apparatus and methods are known. However, they are not without limitations with respect to battery life, manufacturing, and operation. For example, user confidence in device operation may be compromised in certain ways due to user uncertainty about whether the device is actually in an operational mode while it is located in the vagina vault. Current manufacturing processes may be protracted or rendered prohibitively expensive in an effort to mitigate the negative effect of high temperatures used during manufacturing process heating profiles (used to cure device materials such as silicone) on batteries, including on their amp-hour capacity. Further, batteries used in vaginal temperature sensing rings are, of necessity, exceedingly small, and accordingly have a very limited amp-hour capacity; any technology that conserves battery power is a welcome improvement.

Due to the use of the device in the vagina, the surface of the insertable device may preferably be smooth, such as with no seams or crevices to trap biological matter, and there may be no protruding parts, such as may injure the user. This may require that the switch be sealed into the device during silicone molding. Reed switches, which are actuated by a magnet placed near the switch (e.g. within 6 mm), often may be used as switches in sealed devices. Some sealed devices utilize a normally closed reed switch that is in the open state only when a magnet is held nearby such that the magnetic field holds the switch open. One example of such a device is the PillCam™. In these devices utilizing a normally closed reed switch, a magnet may be placed near the switch as soon as the device is manufactured and held there until the device is packaged. Once the device is packaged, a magnet can be held in place at the proper location relative to the device by the package design. When the device is removed from the package, it may be moved away from the magnet, perhaps causing the reed switch to close, and the device may be turned on. This normally closed reed switch method may have the disadvantage that special fixturing and handling may be required to keep magnets near the reed switch once the batteries are inserted during manufacturing and until they are placed in the final packaging containing a magnet. An advantage may be that it may be very simple for the end-user to turn the device on, such as by merely removing the device from the package.

Another aspect of ovulation prediction is desire for increasing accuracy and time of indication. Traditional systems rely on basal temperature activity to make their determinations. This is largely based on the fact that daytime, diurnal temperatures are notoriously noisy and subject to activity and other being-awake temperature impacts. Many improvements in basal temperature processes have been pursued and yet a desire for even better indications remains. Further, there has been a desire for systems that can better satisfy user desires as well as improve with use as a system learns any peculiarities of that particular user or gains overall user experiences.

Accordingly, particular embodiments of the inventive technology address one or more of these concerns by conserving battery power by reducing its consumption during non-use of the device; enabling a user can reliably, quickly and easily determine whether the device is powered on, e.g., during insertion or removal of the device by a user; and/or providing a more efficient, two step curing process; and providing earlier and better indications that a user desires. Of course, the inventive technologies that achieve each of these can be combined in any manner. Other advantages may be indicated elsewhere in this specification.

DISCLOSURE OF THE INVENTION

Embodiments of the various aspects of the inventive technology may include one or more of the following: methods and related apparatus that avoid harming or reducing power of battery(ies) of a vaginal temperature sensing device during its manufacture; apparatus and related methods that allow for user determination that a vaginal temperature sensing device is in a power-on mode; and apparatus and related methods that conserve battery power of an in-situ vaginal temperature sensing ring. They may also provide systems that avoid the traditional basal temperature approach, compare different approach to more appropriately satisfy a user, and even are in themselves intelligent to improve their capabilities. Of course, embodiments may involve combinations of one or more of such aspects, in any combination or permutation.

BRIEF DESCRIPTION OF FIGURES

FIGS. 11A and 11B shows views from both sides of electrical componentry as may appear in particular embodiments of the inventive technology.

FIG. 17 depicts and overall system to show where programming routines and processing or firmware may be located and activity achieved.

MODE(S) FOR CARRYING OUT THE INVENTION

Figure 1:
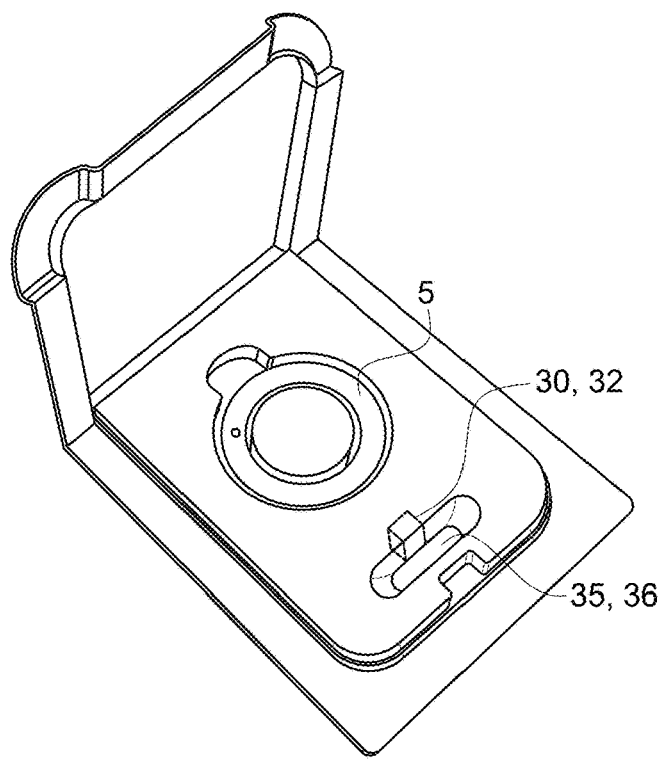
FIG. 1 shows an embodiment with the device in packaging, including a switch reconfiguration site, in its "during shipment" location.
Figure 2:
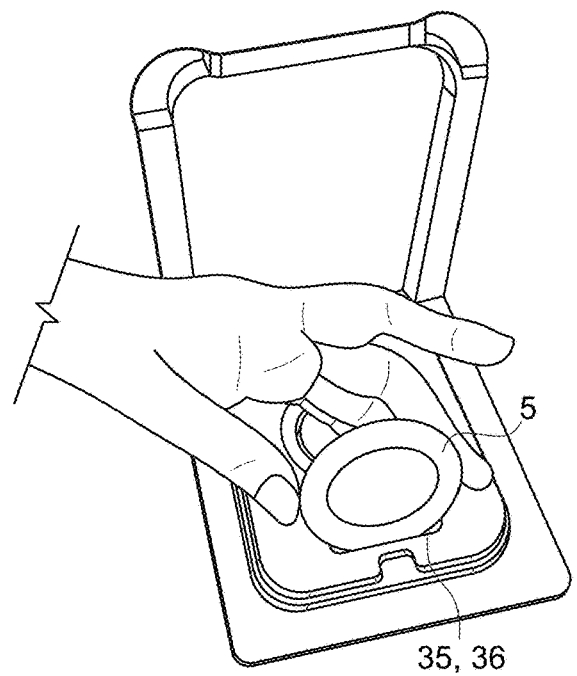
FIG. 2 shows manual placement by a user of the device from its shipment location to the switch reconfiguration site, in the embodiment shown in FIG. 1.
Figure 3:
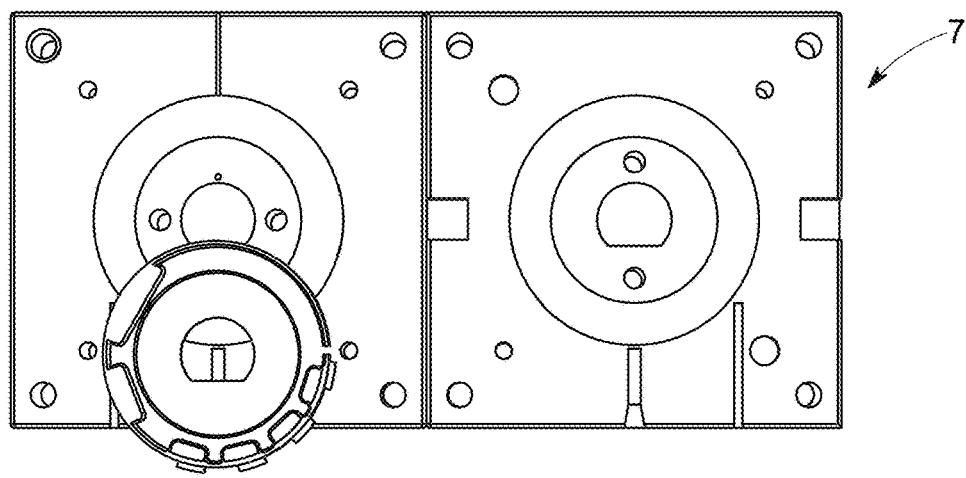
FIG. 3 shows an open device mold, with the insert displaced from the relative position it holds during a first of two moldings, the first used to mold an outer shell in particular embodiments of the inventive technology.
Figure 4:
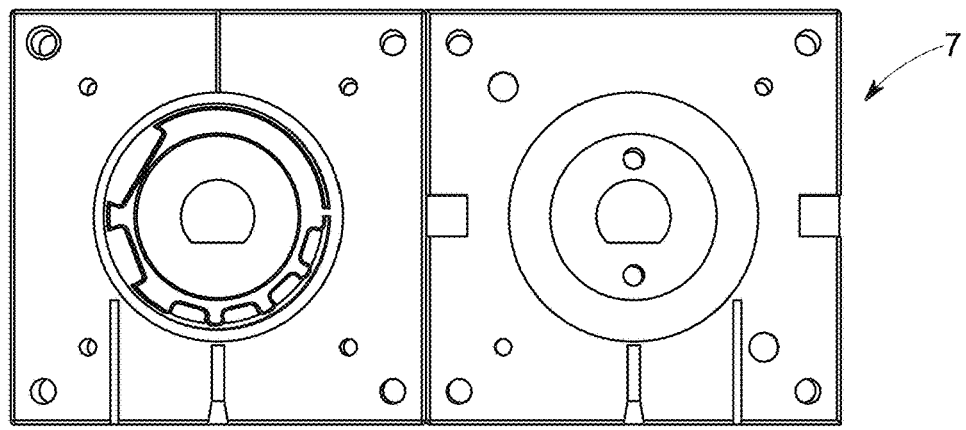
FIG. 4 shows an open device mold of FIG. 3, with the insert in the relative position it holds during the first of two moldings, in particular embodiments of the inventive technology.
Figure 5:
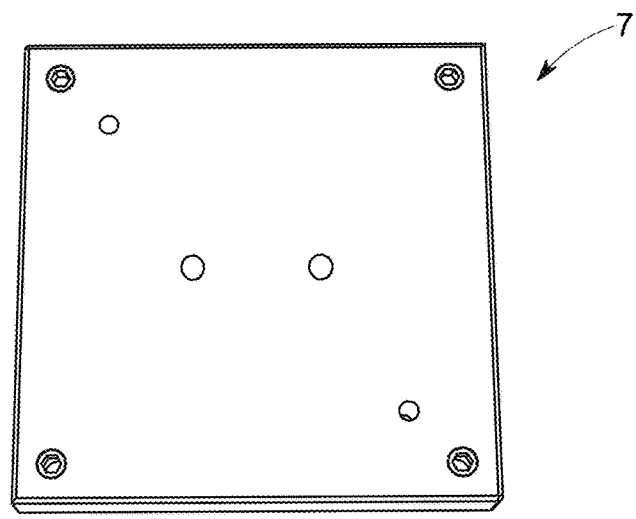
FIG. 5 shows the mold of FIGS. 3 and 4 in closed position, as it would appear during at least the first molding, in particular embodiments of the inventive technology.
Figure 6:
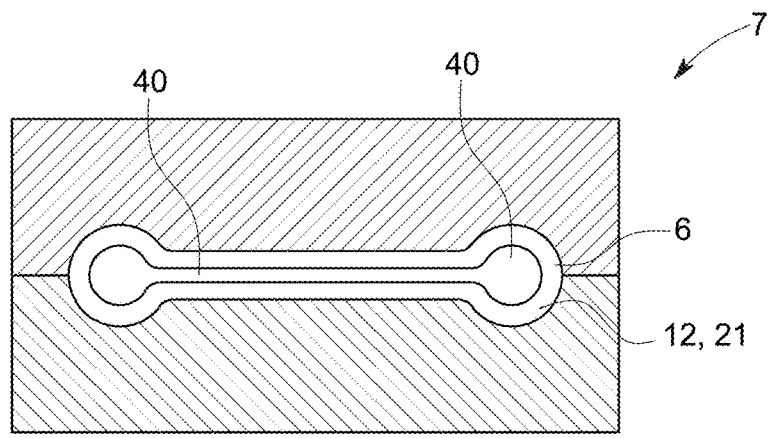
FIG. 6 shows a cross-section from the side of a mold, with insert, and first material between the insert and the mold, as may appear in the first molding in particular embodiments of the inventive technology.
Figure 7:
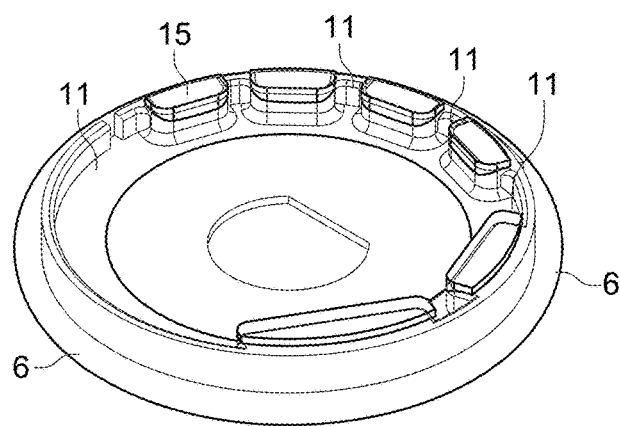
FIG. 7 shows a transparent, perspective view of the device after a first molding, with mold insert still in position, before its removal from the cured outer ring shell, as may appear in particular embodiments of the inventive technology.

As mentioned earlier, the present invention includes a variety of aspects, which may be combined in different ways. The following descriptions are provided to list elements and describe some of the embodiments of the present invention. These elements are listed with initial embodiments; however, it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments are not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

One aspect of the inventive technology focuses on a two step molding process (e.g., with a first molding and a distinct second molding that occurs later) that may use two different materials, each perhaps being curable at different temperatures. As mentioned, in some embodiments, the electronic circuitry, including batteries, may be molded in a medical grade silicone. Medical grade silicones with the proper durometer, tensile strength and tear strength that may be required by the device may require curing at a high temperature, for example at 125° C. Lower temperatures may be used but as the cure temperature is decreased the cure time may be extended. The batteries used in the device may be very small, such as to enable it to meet dimensional requirements. Batteries this small may have been developed for watches and hearing aids. There may not have been any requirement for these types of batteries to be able to survive or maintain amp-hour capacity after exposure to high temperature. A typical battery of this type may be only rated to survive an exposure to 60° C. At 60° C., the medical grade silicones that may have necessary properties may take many hours to cure, perhaps causing the manufacturing process to be too slow and expensive.

A solution to this problem may be a two-step molding process perhaps using a first material (6) (e.g., a first cure temperature material (12)) and a second material (11) (e.g., a second cure temperature material (13)). The first step may be to mold an outer shell in a mold (7), such as using a strong, high temperature cure medical grade silicone (a type of first cure temperature material). Since this step may be done without the electronics (which include the battery (15), a term that includes one or more battery/ies), the outer shell may be cured at a high temperature (e.g., the high maximum temperature observed during such first cure). The shape of this cured, flexible, outer shell (8) (e.g., ring shell) may be chosen such that it may fit snugly around the electronic assembly (a snug fit may be observed even where voids exist between the installed electronics and the shell at any time after installation of the electronics. The electronic assembly (or perhaps a portion of it or its componentry) with, inter alia, battery(ies), where such assembly may also be flexible (e.g., a small width, longer length, flexible circuit board), may be then inserted into the outer shell (e.g., through an access opening (9)). In perhaps a final step (perhaps performed while the outer shell is still in its mold, but not necessarily), lower strength, low temperature curing silicone (a type of second cure temperature material) may be injected into the outer shell, such as to fill at least a portion of voids (between the outer shell and the electrical componentry installed therein). This second silicone may be transparent and a small section may be exposed on the inner diameter (e.g., perhaps filling a window (17) that is established, e.g., via cutting, through the ring), such as to allow the LED to be seen (perhaps as described elsewhere herein). Note that at least a portion of voids could be at least a significant portion of the voids (i.e., at least 20%, by volume), at least a majority portion of voids, or substantially all voids (90% or more). Where only a portion of the voids are filled, it may be that the opening is fully and reliably sealed (e.g., with the second cure temperature material), separating voids within the ring from the outside environment.

Accordingly, particular embodiments of the inventive technology may be described as a method of manufacturing a vaginal temperature sensing ring (5), and may include the steps of: establishing (e.g., via injection or other known insertion technique) first material in a mold (7); curing the first material in the mold at a first heating profile having a first maximum cure temperature, to form a cured, flexible, outer ring shell (8); and establishing an access opening (9) in said cured, flexible, outer ring shell. Like all heating profiles used during device manufacturing, the profile (temperature vs. time graph) may be linear or non-linear, using variable temperatures or constant temperature. The maximum cure temperature is the temperature at which the materials are actually cured; they are the maximum temperatures observed during the respective heating profiles and can be higher than the lowest temperature of the range at which the materials are curable. Even a constant temperature heating profile has a maximum temperature; it is the constant temperature used.

The access opening (9) may be, as but one example, a circumferential slit (14) along the inside or outside circumference of ring-shaped embodiments (including a cut along all or a majority portion of such embodiments). As but one of many additional embodiments, other access openings may be along the circumference at the top or bottom of ring shaped embodiments (where top and bottom refer a device when laid on a horizontal surface). For an opening to be circumferential, it need not be along the entire circumference. Note that the step of establishing an access opening (9) in the cured, flexible, outer ring shell (8) can either be performed during performance of the step of curing the first temperature material in the mold (7) (the mold would be shaped to form the access opening), or after performance of that step (e.g., where the cured, flexible, outer ring shell is cut to form, e.g., a circumferential slit along its inner circumference).

Figure 8:
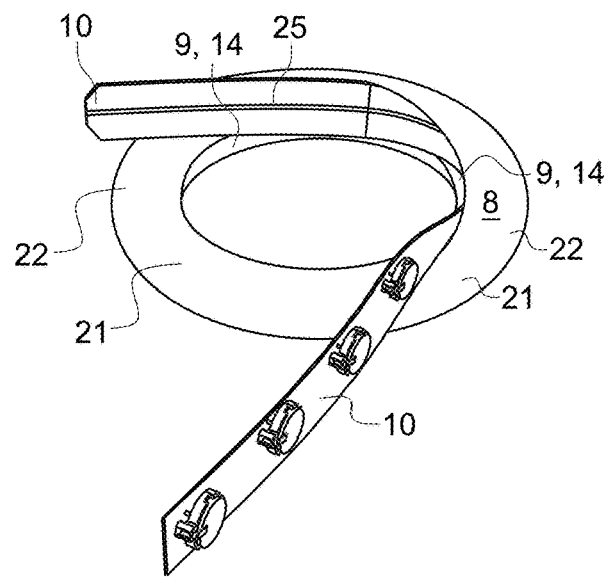
FIG. 8 shows how electrical componentry may be inserted into the cured outer ring shell after the mold insert is removed therefrom, as may be seen in particular embodiments of the inventive technology.
Figure 9:
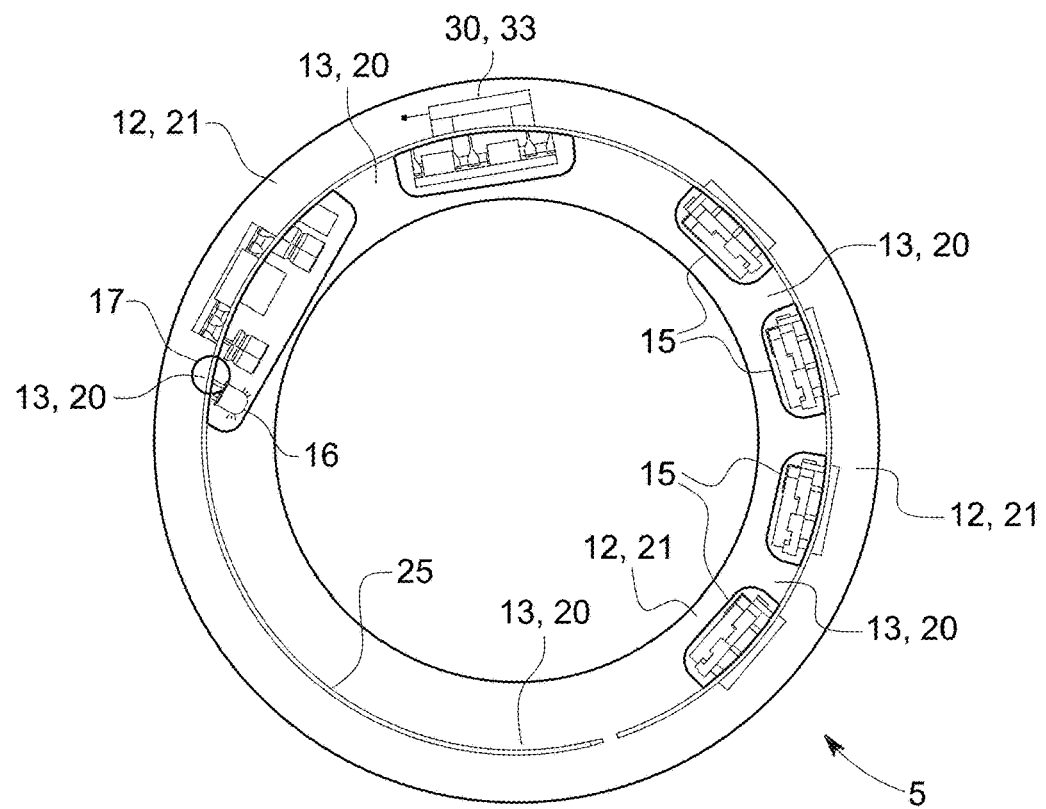
FIG. 9 shows a transparent top view of the device as may appear in particular embodiments of the inventive technology.
Figure 10:
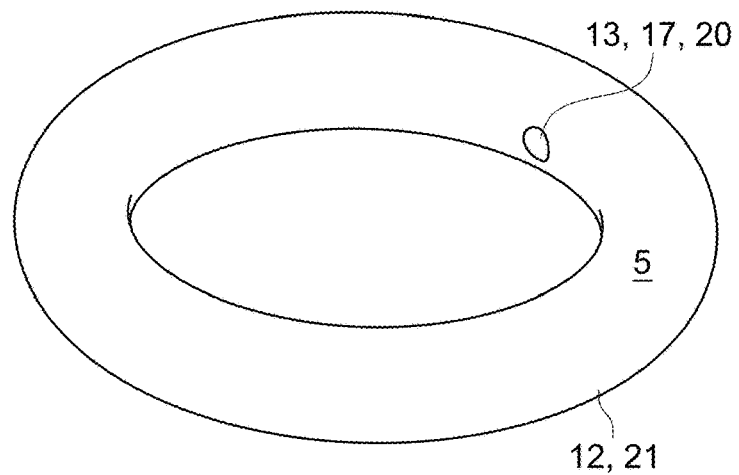
FIG. 10 shows a perspective view of the device as may appear in particular embodiments of the inventive technology.
Figure 12:
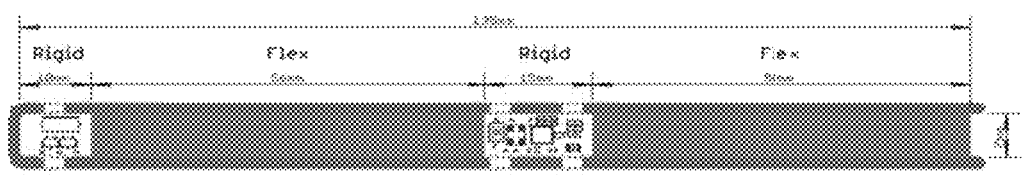
FIG. 12 shows a view from one side of electrical componentry as may appear in particular embodiments of the inventive technology. It shows a flexible printed circuit substrate design with two short rigid sections and two flexible sections as may appear in embodiments of the inventive technology.
Figure 13:
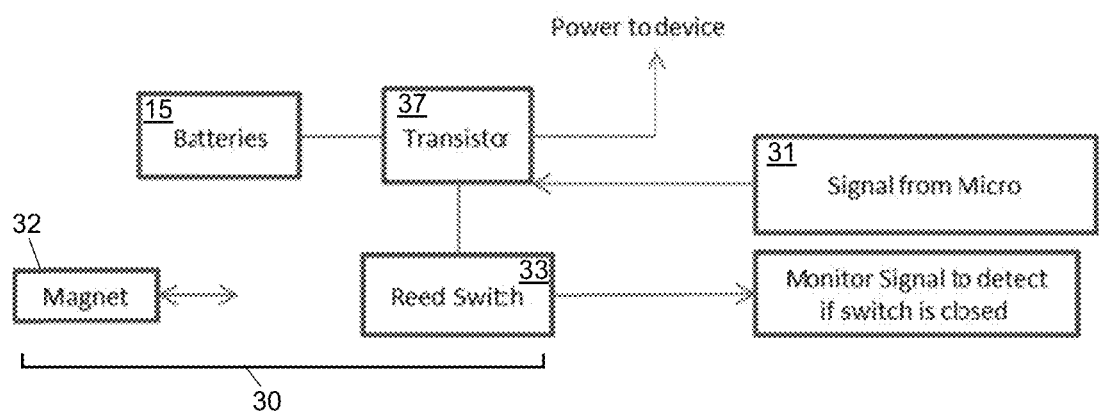
FIG. 13 shows a block diagram of an electrical schematic as may appear in particular embodiments of the inventive technology.
Figure 14:
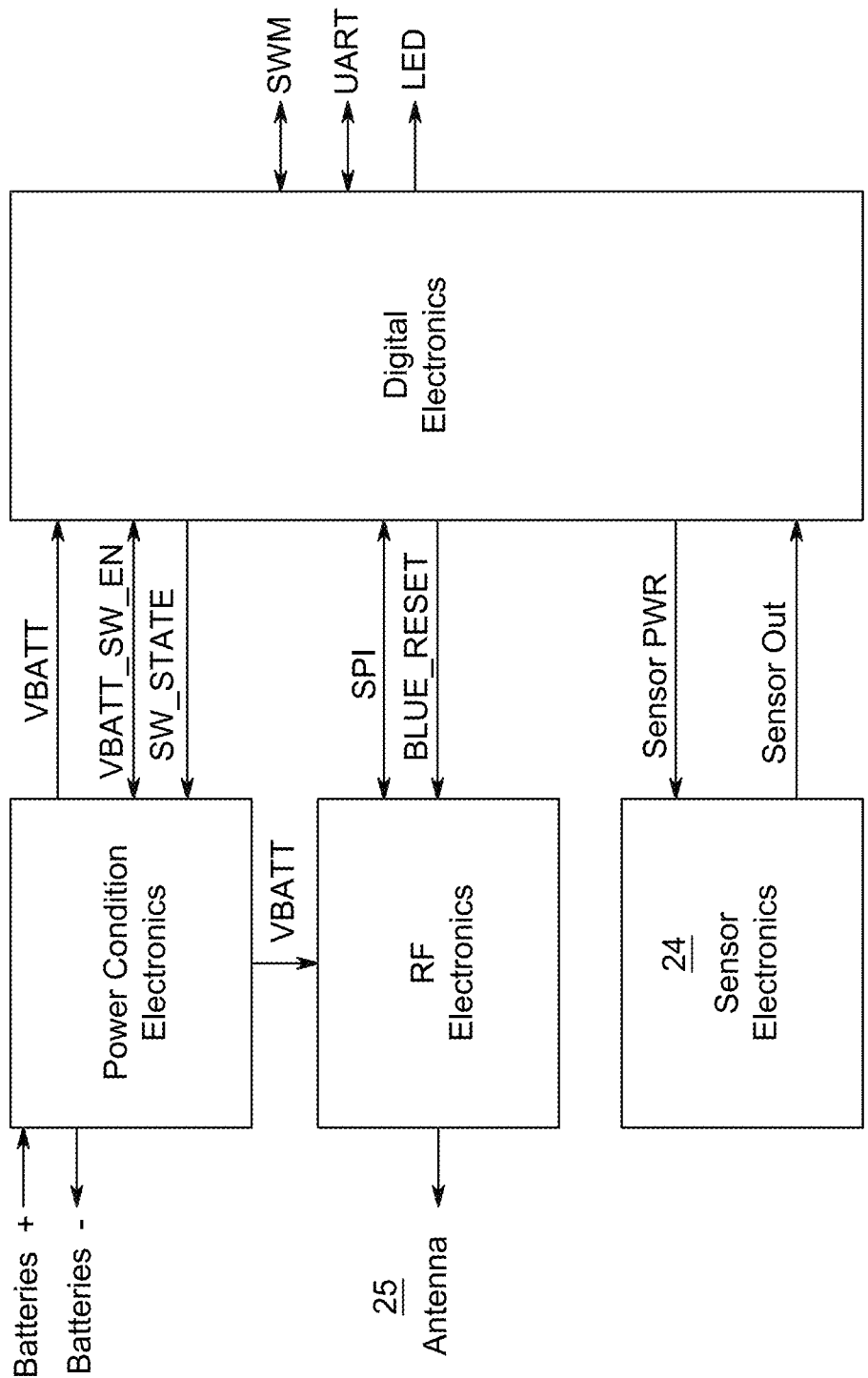
FIG. 14 shows a block diagram of an electrical schematic as may appear in particular embodiments of the inventive technology.
Figure 15:
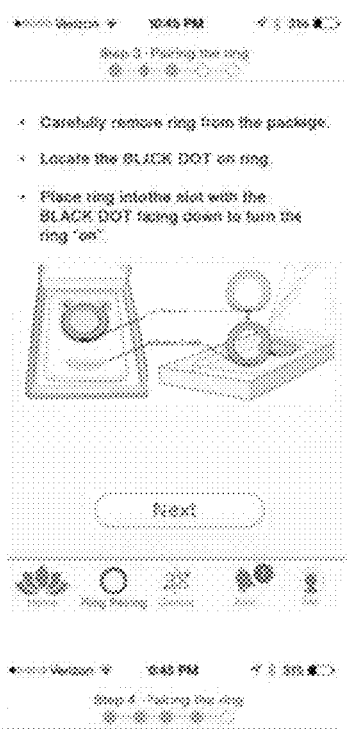
FIG. 15 shows an image (a screen shot) from a cellphone app that instructs users as to how to reposition the vaginal temperature sensing ring to a switch reconfiguration site (a cradle as appears in packaging in the embodiment of FIGS. 1 and 2) in order to activate the ring so that a communication between it and an external device such as a cellphone may be established.
Figure 16:
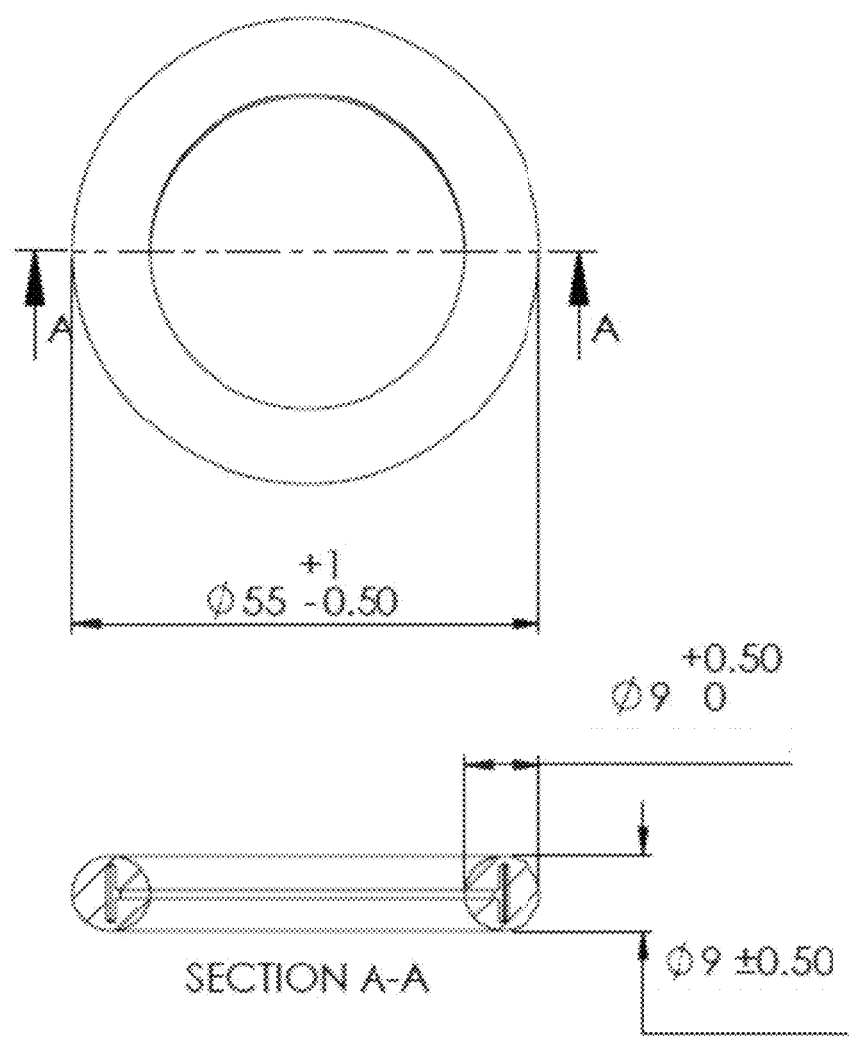
FIG. 16 shows possible dimensions of a vaginal temperature sensing ring as may appear in embodiments of the inventive technology.

Additional steps may include inserting temperature sensing electrical componentry through the access opening (9) and into the cured, flexible, outer ring shell (8) establishing second material within the cured, flexible, outer ring shell (e.g., via injection or other known insertion technique) to fill at least a portion of voids between the temperature sensing electrical componentry and the cured, flexible, outer ring shell (thereby perhaps embedding such componentry in the second cure material); and curing the second material at a second heating profile having a second maximum cure temperature, wherein the second maximum cure temperature is lower (e.g., by at least 10%, at least 15%, at least 20%, at least 25%, at least 30%, at least 35%, at least 40% or at least 50%) than the first maximum cure temperature. The "at least a portion of voids" could be at least a significant portion (i.e., at least 20%), at least a majority portion (i.e., at least 50%), or substantially all voids (i.e., at least 90%). Note that the manner of inserting temperature sensing electrical componentry through the access opening (9) may depend on the type of access opening. For example, where it is an inner circumferential slit (as shown in FIG. 8), it may involve positioning the componentry (e.g., an assembly, such as components strung together to form an electrical circuit string) near and interiorly of the slit and then forceibly inserting the assembly through the slit, which may be held in open position by a tool. Where the access opening is a smaller hole, perhaps a pull string is molded into the circumferential void of the cured outer ring shell, with both ends passing through the access opening; this pull string can then be connected to the electrical componentry (e.g., to one end of an assembly in the form of an electrical circuit string) and pulled through so that the electrical componentry is/are established in the cured, outer ring shell (likely with voids between the componentry and the cured, outer ring shell in which it/they rest(s)). The smaller hole can be, e.g., just large enough to pull the electrical componentry through it.

Steps, from the beginning, followed in manufacturing at least one embodiment of the vaginal temperature sensing apparatus may include one or more of the following: place a mold insert (40) into a cavity defined by at least part of remaining parts of the mold (note that the mold insert, a part of the mold, may, inter alia, help to create cavities within the shell within which electronics may be installed); close mold (including perhaps tightening of bolts to keep mold closed, with its components in proper relative position); preheat mold (e.g., to 59° C.); inject (e.g., hand inject) first cure temperature material (e.g., MED 4950 silicone) into mold (e.g., via injection into a mold gate until the first temperature material exits the mold vent (exemplary pressure may be 80 psi), perhaps after mold is removed from heating equipment; place mold (with, e.g., silicone thereon) back into heating equipment for, e.g., 6 mins at 205° C.; allow mold and injected material to cool; remove silicone from gate and vent holes; open mold; remove silicone, with embedded insert from remainder of mold (e.g., from clamshell portions of mold), referred to as a ring part; hand trim silicone flash from outside of ring; hand trim interior flash by cutting close to the center of the ring and insert; pull silicone ring off of insert, said ring having an interior space substantially along its annular centerline, and a circumferential slit/opening at the inner circumference of the ring (of course, however, such slit/opening could be established elsewhere, e.g., along the outer circumference of the ring, or along the top or bottom circumference (e.g., substantially the highest, circumferential "ridge" or the lowest circumference, i.e., that portion that may contact an underlying surface when the ring is laid flat), or any circumference anywhere between any of such circumferences). After such steps are performed, one may have a cured, flexible outer (ring) shell (i.e., without electronics in it).

Additional steps may be as follows: the cured, flexible outer ring shell (8) may be wiped with, e.g., isopropyl alcohol; the ring may then be opened at the access opening (9), e.g., where the two opposing edges at the access opening are forced apart, and electronics (e.g., an assembly) is installed so it (or sub-component(s) of it, such as battery(ies) (15), PCB's) fits in any pockets/cavities created by the mold (e.g., by the insert); using a Q-Tip, e.g., coat entire inside of ring and electronics with a primer such as MED 160 Nusil Silicone Primer; pre-fill battery cavities only, with MED4-4220 silicone (a second material); fill ring with silicone adhesive (another type of second material); place ring in mold (in clamshell mold, without insert, where a clamshell type mold is used, orienting main circuit board with gate; close mold and tighten; fill mold (e.g., via injection, such as manual injection, here actual injection pressure may be unknown) with Nusil MED4-4220 silicone adhesive (a type of second material) until it flows out of vent to fill substantially all voids within the cured outer shell; place mold on heated press and heat at 59° C. for 12 minutes (a lower intensity heating profile than that used for curing the first cure temperature material); and open mold and remove part from mold (perhaps after first hand trimming flash). Such steps may result in a ring device with electronics inserted therein, and in a device that, but for any componentry that is external of the ring (e.g., part of the (possibly substantially error-free) user-initiated device activation componentry (30)), and any packaging, is substantially ready for sale. Note that all steps indicated as manual could be accomplished in another manner, e.g., robotically.

More specifically as to the electrical assembly (electrically connected electrical componentry), as in any embodiment, may be vaginal temperature sensing electrical componentry, such as including a battery (15), vaginal temperature sensor (24), wires (perhaps in the form of conductive connections such as traces between other electrical components), possibly (wireless) signal receiver (28) (e.g., an antenna (25) and associated componentry, for receiving wireless signal commands from a user to, e.g., send data), switch componentry and data transmission componentry (e.g., to send temperature-related data, whether at a pre-determined time and/or when commanded by an external communication device such as a cell phone). Componentry as used herein may refer to all electrical components, or merely only one component or a larger portion of all components; assembly implies some sort of electrical connection between such components). In certain embodiments, componentry may include batteries, power conditioning electronics (e.g., power conditioning board), sensor electronics (including a sensor), digital electronics, RF electronics, trace antenna (25), switch componentry, perhaps as (substantially error free) user-initiated device activation componentry (30) or part thereof, with connections thereamong as appropriate (see, e.g. FIGS. 11A and 11B). In particular embodiments, certain componentry may be established on or to include a sensor, digital electronics and radio PCB. Circuitry may be established as part of a flex circuit, i.e., one whose function is not compromised by the flexing that may be observed when the device (e.g., ring) in which the circuitry may be embedded and of which it may form a part is bent (e.g., upon insertion into a vaginal vault). Note that, particularly with respect to those embodiments that include user-initiated device activation componentry (30), portion(s) of such componentry may be established outside/externally of the device (e.g., the ring), e.g., in the packaging.

In some embodiments, the device flexible circuit substrate design may include two rigid sections, located such that when the flex circuit is curved into the ring shape, they may be spaced 180 degrees apart. The length of each of the rigid sections may be short enough such that when the device is flexed it may meet the standards for bend radius and percent compression, for example, as established in ISO Standard 8009 (2014) "Mechanical contraceptives—Reusable natural and silicone rubber contraceptive diaphragms—Requirements and tests." For some embodiments, the maximum length of a rigid section that meets these criteria was determined to be 17 mm. Even when very small surface mount and chip scale packaged components are used, placing all the circuitry and batteries on one rigid section may cause the section to be longer than 17 mm and therefore one longer rigid section might not meet the standards mentioned above in these situations.

The electrical componentry may also include a visually sense-able (capable of being visually sensed), battery power-on indicator (16) (e.g., a LED that is lighted, whether blinking or otherwise, when any amount of battery power, even only sleep mode power, is drawn). Such may help to avoid mis-readings, and improve user confidence in the device and data produced thereby. Transparent material (20), such as low (second) cure temperature material may be used in the proximity of the battery (a term that includes a plurality of electrically connected batteries) and may be used to fill at least a portion of any voids between the inserted electrical componentry (e.g., batteries and electrical componentry) and the flexible outer ring shell. It may also be established between the installed indicator and an outwardly exposed surface of the device (at that location) so that the visually sense-able indicator can be visually sensed (e.g., seen) by a user. A manufacturing step that may enable the intentional establishment (e.g., placement) of such transparent material (20) so as to allow a user to see the visually sense-able battery power-on indicator (16) is the creation of a window (17) (whether by, e.g., cutting, drilling or punching of a portion of the cured ring shell, or by molding that window during the first cure through use of the mold). Transparent material (20) (which may be second cure temperature material) may be be established in that window 17 (e.g., via injection, etc.) at some point after the first cure but before the second to create a transparent material filled window. Of course, manufacturing steps should consider the location of the window, the location of the indicator on the assembled circuit, and the orientation of the circuitry during installation so that the visually sense-able indicator, after installation, is at the window. The window may be a small window (i.e., with a radius that is less than 20% a characteristic radius (e.g., radius where the ring is circular; average radius where it is, e.g., oval or elliptical) of an unbent ring. It may be: just large enough to allow light from the indicator to pass through it to outside of the vaginal temperature sensing ring, and/or just large enough to allow injection therethrough it of the transparent, vaginal ring material (20).

A first material (6) is typically used during the first of two distinct cures, and a second material (11) is typically used during the second cure. Note that the first and second materials may indeed be the same type of material, perhaps even having a range of temperatures and curing profile that are identical. Indeed, the most striking feature of the inventive technology is the use of two distinct curing steps (one with the first material, and the second with the second material), and not whether the two materials are different. However, the second material may indeed have a different range of materials at which it is curable than the first material, and may be curable at a temperature that is lower than the temperature at which the first material is curable (note that such cure temperatures may be temperatures that material specifications show are required to sufficiently cure the respective material under constant temperature heating profiles of equal duration, and may be different from maximum temperatures used in the respective heating profiles actually used). As such the first material (6) may be a first cure temperature material (12) and the second material (11) may be a second cure temperature material (13). It should be understood that any particular curable material may be curable within a range, and where at least a lower portion of that range is at or below the highest temperature that batteries can survive (without unacceptable degree of damage/loss of capacity, etc.), it is possible that embodiments of the two-step curing procedure could use the same curable material for each step such that the first material is the same type of material as the second material. However, the maximum cure temperature of the second cure step is typically lower than the maximum cure temperature of the first cure step, and no greater than the highest temperature that a battery can endure without unacceptable impairment or damage. Note that while certain embodiments may indeed include identical curable materials for the first and second moldings, it may be preferred to use different materials (which may indeed have different cure temperatures) because it may be preferred that, e.g., the first cure temperature material, once cured, has, e.g., a higher tensile stress than the second cure temperature material and/or only materials with different cure temperatures offer the manufacturing efficiency advantages (e.g., speed during curings) sought by certain embodiments.

A first cure of a pre-completion device that lacks a battery (and indeed perhaps any electrical componentry) allows the use of a higher maximum curing temperature, and if preferred, a material (a first cure temperature material) that cures at a higher cure temperature (such as a maximum cure temperature) than (and this is of different type than) the material used for the second cure (a second cure temperature material); the following, second cure, where heating of the battery was unavoidable, will typically use a lower maximum cure temperature (and perhaps a material with a different range of curing temperature than the first material). Note again, however, that while it may be preferred that the first material is of different type (and has a different curing temperature range) from the second material (i.e., the first material is a first cure temperature material and the second material is a second cure temperature material), in certain other embodiments, it may be that the first temperature material is the same type of material (e.g., the same medical grade silicone) as the second temperature material.

Advantages of segregating the cures into a two cure step process, with each step using different heating profiles, may include one or more of the following: reduction or avoidance of heat caused injury to battery, faster first cure time, faster overall manufacturing time, and/or ability to use stronger tensile strength material for the curing of the outer ring shell (during the first cure).

As such, the following characteristics may apply to the two materials that are cured in the first and second cures, when the materials are different type materials: first material may have a higher tensile strength (once cured) than the second material; the second material may be transparent while the first material may be opaque (e.g., it may be non-transparent vaginal ring material (21), perhaps to prevent visual recognition of electronic componentry, which a user may find disconcerting, given that the device is inserted into the human body); and second material may be second cure temperature material that is curable at a lower temperature than is the first material, which may be first cure temperature material; the first material and the second material may each a type of silicone; both curable materials, and at least the first temperature curable material may meets International Standard ISO 8009 (2004) and/or ISO 8009 (2014) requirements (related publications cited and incorporated herein) when the device is to be worn intra-vaginally; and the first and/or the second material may be medical grade material, may be medical grade plastic, or may be thermoplastic. Further, each may be a type of flexible, non-conductive vaginal ring material, and as the first (cure temperature) material may be cured to form the outer ring shell, it may be a cured, flexible, outer ring shell material (22); the second (cure temperature) material, given that it may be used, inter alia, to fill at least a portion of the space between installed electrical componentry and the outer ring shell, may be referred to as void filling (internal ring) material.

The second cure may be one of the final steps in manufacture, if not, the final step. The manufactured device may have a ring shape (e.g., a toroidal shape, a circular shape, an oval shape, elliptical shape, closed curvilinear shape, diamond ring shape, wedding band shape, kettlebell shape, or polygonal shape, all whether in one plane or not). Note that the device may be shaped so that it occupies one plane, i.e., it is flat (ignoring its height) before user-insertion into a vagina, but that when pinched immediately before insertion, and effectively, while in inserted condition, might not be flat, not unlike a pinched rubber O-ring. In particular embodiments, it may be elastically biased towards the shape it occupies before insertion, e.g., unbent (possibly flat) shape; in others, it may be biased towards the shape it occupies after insertion. Notable is the possible location of certain electrical components, such as any antenna (25) that is used, as such antenna in certain embodiments may be established substantially along the entire circumferential length of the ring (e.g., substantially along at least 90% of the curved circumferential centerline of the ring), or substantially at only a localized portion of it (e.g., along less than 30%, less than 25%, less than 20%, less than 15%, less than 10%, or less than 5%), as may be seen where an antenna is fit into a box or container established at less than 15% of the curved ring centerline. Indeed, in certain embodiments, all electrical componentry may be contained in such localized portion. Accordingly, it should be understood that the inventive technology is not limited merely to those designs where electrical componentry, such as an antenna, is established substantially along the entire circumferential length of the ring. Indeed, in the various manifestations of the inventive technology, electrical componentry (such as, but not limited to, any antenna that is used) can be established almost anywhere with respect to the non-conductive material (e.g., silicone) in which that componentry may be established—electrical componentry can be distributed along the circumferential length of the device or can be "bunched" or packaged together at only a localized portion of it. In such designs, such might cause the device to have an increased width (e.g., difference between outer and inner radii), although this is not a required feature in such designs.

A vaginal temperature sensing ring (5) may be described as including: a cured, flexible, outer ring shell (8) made of first material; temperature sensing electrical componentry established in the cured, flexible, outer ring shell; and cured second material established within the cured, flexible, outer ring shell and between the temperature sensing electrical componentry and the cured, flexible, outer ring shell. As mentioned, the second cured material and the cured, flexible, outer ring shell may have been cured during two distinct cures (indeed, such may be discerned from a distinct boundary between the two materials, after the final cure is entirely completed, where such boundary is an interface of three dimensional surfaces of the two cured materials). Such materials may be identical, or instead may be a first cure temperature material and a second cure temperature material.

An independent but potentially related aspect of the inventive technology may focus more on the use of transparent material, such as to allow for visual recognition of a visually sense-able, battery power-on indicator (16) (e.g., a light, such as but not limited to a LED) that enables the user to reliably conclude that the device is indeed on, whether in sleep mode or another power mode, such as full activation power mode, which may be present immediately after signaling a device that is in sleep mode. In such manner, a user can know that the device is on before insertion into a vagina, and/or that the device is on upon removal therefrom. Accordingly, a vaginal temperature sensing ring (5) may include: temperature sensing electrical componentry that comprises a battery and a visually sense-able, battery power-on indicator (16) electrically connected with the battery; and flexible, non-conductive vaginal ring material in which the temperature sensing electrical componentry is established, the flexible, non-conductive vaginal ring material comprising transparent, vaginal ring material (20). In particular embodiments, at least a portion of the transparent, vaginal ring material is positioned so that light from the visually sense-able, battery power-on indicator passes through the at least a portion of the transparent vaginal ring material to outside of the vaginal temperature sensing ring. As mentioned, one way such positioning may occur is via establishment of transparent vaginal ring material (20) (e.g., cured, second cure temperature material) in a window (17) that is cut so that the visually sense-able indicator is/will be at the window (e.g., positioned within the ring so that sufficient light from the indicator passes through the window). At least a portion of the transparent material (whether entirely clear, or just clear enough to allow sufficient light therethrough (enough to be visually sensed by a user holding the device), or between such extremes) may be established between the visually sense-able, battery power-on indicator and an outwardly exposed surface of the vaginal temperature sensing ring (such surface may be a window surface). Note that in certain embodiments, the second cure temperature material (e.g., the transparent vaginal ring material) may be only inside the ring, in the window, and perhaps as the seal at any former access opening (9) (e.g., a sealed access opening).

A related method may be described as a vaginal temperature sensing ring method comprising the steps of establishing temperature sensing electrical componentry in flexible, non-conductive vaginal ring material (e.g., such that it is eventually embedded therein), the temperature sensing electrical componentry comprising a battery and a visually sense-able, battery power-on indicator (16) electrically connected with the battery; where the non-conductive vaginal ring material comprises transparent, vaginal ring material; and positioning at least a portion of the transparent, vaginal ring material 20 so that light from the visually sense-able, battery power-on indicator (16) passes through the at least a portion of the transparent vaginal ring material to outside of the vaginal temperature sensing ring. Again, one manner the step of positioning at least a portion of the transparent vaginal ring material in such manner may be to establish such material in a window (17) that is cut or otherwise formed in the outer ring material (often opaque, such as having pink or other color), where such window is created at the location of the visually sense-able indicator (e.g., substantially outside that indicator).

In some embodiments, the inventive technology can include a unique ON/OFF method perhaps combined with a packaging method and even smartphone App types of communication. For example, vaginal sensor rings typically may need a long shelf life, such as of at least one year prior to use, to meet supply chain requirements. Dimensional constraints of the ring may dictate the use of extremely small and therefore low capacity batteries. To meet the requirement of long shelf life with the small batteries, it may be desirable to totally disconnect the electronic circuitry from the battery after manufacturing and testing (it may be that not even extremely small leakage currents or sleep currents of an electronic timer circuit can be tolerated). For example, a switch may be used to connect the battery to the circuitry for post-manufacturing testing and then to switch it off after testing so it is electrically disconnected during the supply chain period prior to sale. A simple means can be used by the final user to switch the device (e.g., a ring) on prior to use.

In some embodiments, the inventive device may have a reed switch that is normally open. The switch may be usually closed only when a magnet is nearby, such as within 4-6 mm, as but one example. This normally open switch may eliminate the need for a magnet to be kept near the device after manufacturing and prior to use. Instead, a magnet may be brought to the device and/or the device may be brought to the magnet for testing and again when the end user turns the device on for use. This normally open reed switch design may have disadvantages over the normally closed reed switch design. One disadvantage may be that this design may require the end user to carefully place a magnet and the device in precise, proximal correct relative location in order to close the switch to turn the device on prior to use. A second disadvantage may be that if a strong magnet unintentionally comes near the device, say during storage, shipping or in a retail store, the device could be turned on and the battery depleted prior to being used. However, these disadvantages may be acceptable for certain applications and/or may be deemed not as significant as disadvantages inherent in, e.g., normally closed switch designs (and thus may be observed in certain embodiments). Further, in certain other embodiments, novel methods (and apparatus) may be employed to overcome these disadvantages.

In some embodiments, the device may include a microcontroller (e.g., a microprocessor) running a software program and other circuitry that may include a transistor switch. The transistor switch may be opened or closed by an instruction from the microcontroller. When a magnet and reed of the reed switch of the device are brought sufficiently close to each other, the reed switch may close and provide power to the microcontroller and the other circuitry. When thus initially powered, the microprocessor program may cause a signal to be applied to the transistor switch which may then switch it to a closed state. In some designs, the transistor switch may be in parallel with the reed switch, and therefore may also connect the battery to the microcontroller and circuitry. The magnet may now be removed, since the transistor switch may maintain the battery connection when the reed switch switches open.

At the time the microcontroller may cause the transistor switch to close, it may start a timer. After the timer period, for example (30) seconds, the microcontroller (a microprocessor that may include or interact with a timer (31)) may send an instruction that will cause the transistor switch to open, disconnecting the battery. Such instruction may only be sent if a certain event, e.g., pairing of an external device (e.g., a cell phone) is not successfully initiated or completed by the end of the timer period. This method may provide for a short period of time after turning the device on with a magnet for testing (such certain event likely not occurring during testing). It may also prevent the device from staying turned on if it unintentionally comes into a strong magnetic field (such certain event likely not occurring in the time period after such unintentional activation).

To perhaps make it convenient for the end user to turn on the device, in various embodiments a magnet may be provided in the packaging (e.g., near a cradle (36) defined by the packaging). The location of the device and the location, size and strength of the magnet may be chosen so as to ensure the magnetic field is too weak to actuate the reed switch when the device and magnet are in their fixed, in-package, shipment locations. The device may, e.g., during shipment to consumer or point of sale, be held firmly in a fixed location, sufficiently away from the magnet so as to not cause switch reconfiguration to its closed mode, such as through the use of a molded insert with an indentation, or circular channel, that it may fit into with a slight compression fit. The magnet may be held firmly in place, such as in another section of the package molded insert, e.g., near a cradle (36), perhaps by either a slight compression fit, or with an adhesive, or the like.

When the user is ready to use the device, she may follow instructions to remove the ring from its fixed location and place it, such as at switch reconfiguration site (35) such as but certainly not limited to a slot (a type of cradle (36)) in the package that provides a slight compression fit. The switch reconfiguration site may be the general area, whether in a cradle or otherwise, into which the device may be placed in order to reconfigure the switch (e.g., reconfigure the magnetic reed switch from an open configuration to a closed configuration). Note generally that moving a magnet (e.g., in a hand-held wand) sufficiently close to the reed switch of a device is also deemed an example of moving the device to a switch reconfiguration site (35) (where such "moving" includes a type of relative movement). A magnet may be sufficiently close to that site so that when the device (e.g., ring) is placed in that site (including placed, perhaps, in specific orientation such as indicated by a marking on the device), the magnetic reed switch reconfigures from, e.g., open to closed configuration. This compression may hold the device in place, for example, in an upright or near upright placement. The user may be instructed to place the ring, such as in a specific rotational orientation, for example by aligning an indicated mark, indentation, molded feature, or the like on the ring with a mark on the packaging. Placing the device such that the indicated marks line up may assure that the reed switch in the device is placed sufficiently near the magnet molded into the package (see for example FIG. 1) to assure its reconfiguration to a different mode (e.g., from open to closed mode).

Once the device is placed, such as in the slot in the proper alignment, the magnet may cause the reed switch to close and the microcontroller and circuitry may cause the transistor switch to be closed, such as described above. The device may now be removed from the packaging, i.e. away from the magnet, and it may stay turned on, such as until the microcontroller timer (31) times out and the transistor switch is opened, perhaps by an instruction from the microcontroller. Indeed, users may be instructed, e.g., via written or video instructions (perhaps via webpage reference) accompanying the device (e.g., ring) as sold, to remove the device from the cradle shortly after it is inserted therein, thereby avoiding a condition where the reed switch remains closed (because it is sufficiently close to the magnet) after the timer period is reached.

In some embodiments, when the microcontroller is first powered, such as may be described above, a program may be initiated that may instruct the circuitry to send data, such as data packets, to attempt to communicate such as via wireless means, for example via Bluetooth Smart, with a computer, smartphone application, or the like. Indeed, at such time, any effort to communicate with an external device can be made automatically. At the time the user places the device, such as in the slot (a type of cradle (36)) (generally, at a switch reconfiguration site), which may be in or part of packaging (or external of it), she may be instructed to turn on (or have turned on) her phone or computer application and place it (or have placed it) into scan (or listen) mode. When placed in the scan mode, the computer program or Application (App) in the computer or smartphone may actively attempt to establish communication (pairing) through the wireless means with the external (body external) device. The App may be put into scan mode either shortly before or shortly after the device is actuated, as both the scan period and search period of the device may be timed, for example to continue to attempt pairing for (30) seconds or longer (or even shorter).

Once the device and App, computer program in the receiving device, or the like establish communication, instructions in the device microcontroller computer program may cause the timer (31) to be "turned off" (e.g., such that it does not lead to any opening of any circuit that it otherwise may be programmed to) and the transistor switch may stay closed, maintaining the battery connection to the circuitry. If no such communication is established with the App, the timer (31) may cause the transistor switch to open and if there is no magnet nearby (e.g., as may be the case if the ring has been removed from a switch reconfiguration site (35) and the switch of user-initiated activation componentry is a normally open switch), the device may turn off.

Naturally, these descriptions describe embodiments that are exemplary in nature, and should not be construed to limit other embodiments consistent with the underlying inventive principles disclosed. Generally, the apparatus may include user-initiated device activation componentry (30) configured to turn the device on (and initiate the consumption of battery power) upon the occurrence of a particular event, perhaps in conjunction with the aforementioned timer. Examples of such activation componentry (30) include but are not limited to: proximity switch such as, e.g., magnetic reed switch, and pressure switch, and device bend switch. A proximity switch is closed (i.e., is activated or initiated) when it is place in proximity with (sufficiently close to) a certain material (e.g., a magnet). Most preferably, a switch that does not consume any amount of power in order to determine if an attempt is being made to activate it, is used (e.g., a magnetic reed switch). For example, remote sensing switches used in, e.g., some television sets with wireless "remote control," may consume some low level sleep or standby power when the device appears to be "off" in determining whether an attempt is being made to turn them on, might not achieve low power consumption goals of certain aspects of the inventive technology disclosed herein. Certain types of proximity switches, or remotely signaled switches, are not preferred because they consume power even when the device they control power to appears to be "off."

The above magnetic reed switch approach may analogously work with other types of momentary contact switches that may be sealed in the device. The magnetic reed switch, and other types of proximity switches, may be viewed as part of an exemplary type of user initiated device activation componentry (30), that may possibly be substantially error free, that includes component(s) that are not only in the (inserted) device (e.g., like the switch) but also outside of the device (e.g., the magnet that is near, e.g., a cradle (36) of the packaging). Some embodiments may utilize a membrane or other push button switch, such as those that may be used on calculators and other small electronic devices, and that could replace the magnetic reed switch. This type of switch may contact or close when compressed, which may be done through flexible silicone or the like; with such switch, the entire user initiated device activation componentry (30) may be in or part of the device (e.g., the ring). The circuitry may behave in the same or an analogous way when the possibly momentary contact is made, such as by pressing the device in the correct spot, as when the magnet may be brought near the reed switch.

To enable testers and end users to know, perhaps immediately, that the device has successfully connected to the computer, smartphone, or the like, the device may contain a signal such as an LED that may blink a certain pattern when the microcontroller confirms a successful connection. This may be based on exchanging certain predetermined information with the App. This blinking may be momentary, say for several seconds, to conserve battery power. Instructions in the App computer program may also cause the computer or smartphone to display an indication that the communication link has been successful. However, once communication is established, the device might only communicate infrequently to conserve battery power and this long period between communications may delay the indication on the smartphone that communication is successfully established. The App may indicate successful pairing with the device.

The device may be more acceptable to users if it is opaque such that the user cannot see the electronic circuitry inside. Therefore, in particular embodiments, the silicon molded around the device electronics may contain a colorant or the like to make the silicone opaque. As mentioned, to allow the LED that indicates successful communication to be visible through the silicone, a custom molding method may be used to create a transparent or translucent opening (e.g., a window 17 such as a port or strip of any shape), such as on the inside diameter of the ring, that may expose the light from a properly oriented LED to the user.

Another embodiment, such as to eliminate the need for an LED and the issues it may cause with the molding, may be to use a small buzzer (perhaps such as like in a Fitbit™) that may buzz when a successful communication is established. This may be heard and felt through the molded device. The buzzer may be disabled after successful communication with the App is confirmed and should be configured so that it is not actuated while being worn by the user.

Accordingly, an aspect of the inventive technology may be described as a vaginal temperature sensor apparatus comprising temperature sensing electrical componentry comprising a battery, vaginal temperature sensor componentry (24), and sensed vaginal temperature transmission componentry; non-conductive, flexible material proximate the temperature sensing electrical componentry (e.g., substantially around that circuitry (around at least 90%, including entirely around that circuitry), along all sides of such circuitry, and substantially along its entire length (along at least 90%), including along its entire length); and user-initiated device activation componentry (30) (that may indeed be substantially error-free), configured to turn the device on (and initiate the consumption of battery power, however small) upon occurrence of a user-caused event. Such apparatus may further comprise a timer (31) configured to start a countdown of a time period in response to start of use of battery power. The apparatus may be configured to terminate use of battery power in the event of non-occurrence of establishment of a communication link between the apparatus (e.g., a ring of the apparatus) and a different electronic device (e.g., a cell phone) before the expiration of said time period.

Substantially error-free includes performance, where, but for rare, unanticipated, statistically low (less than 0.5%) probability events such as, e.g., pressure switch activation caused by a vehicular collision involving a truck that is transporting packaged devices, or activation of magnetic reed switching by, e.g., a power ambient magnetic field, there are no instances of premature initiation of battery use (i.e., drawing of any amount of battery power before a design event intended to initiate batter power consumption, such as, but not limited to, removal of device from package or insertion into cradle (36), user application of pressure to device, and user bending of device (typically in a direction opposite the bias force, and/or away from the device's biased shape, as may occur immediately prior or during device insertion into the vaginal vault)).

Note that in certain embodiments, the substantially error-free, user-initiated device activation componentry (30), at the instant when it initiates the consumption of power, may provide tactile feedback (e.g., a clicking, threshold displacement of a tactile dome), particularly with respect to manually operated versions (e.g., where the device is bent, or a pressure switch is pressed).

The occurrence of an indicated event may cause the (substantially error-free) user-initiated device activation componentry (30) to initiate entry into a power mode in which at least some power, even small power amounts, is drawn from the battery (as seen in, e.g., a lower power mode). Such initiation into entry of a power mode may occur even where that power mode is not immediately observed (e.g., there may be an initialization process, i.e., an initialization power mode, that may occur before the intended power mode, e.g., a different, longer term power mode, such as a lower power mode, is achieved). The lower power mode may be, e.g., a sleep/standby mode power mode, where, e.g., the device, in manner similar to many remote control devices in sleep mode until they are signaled to turn fully on, draws low, phantom or standby power, waiting for a signal (e.g., RF) from an external device (e.g., a cell phone, as but one example), upon receipt of which, it might enter a higher power mode where that device is in full activation (power) mode. Indeed, in embodiments of the inventive technology, wireless control protocols (RF or other) such as Blue Tooth™ may provide a sleep mode power mode that effectively awaits and "looks for" (monitors for) a signal from outside (e.g., from a user, via signal monitoring by the device) to enter a full activation mode where temperature can be and sensed, and data can be transmitted via a data transmitter (27). The device may also, or instead, attempt to establish a communication link with an external device by transmitting signals itself. Regardless, such general capability may help to conserve power. Note, incidentally, that any known wireless protocols, such as but not limited to that used in Blue Tooth™, may be used for wireless communication to the device (e.g., from the user via a computerized system such as a cellphone application) and/or wireless communication from the device (e.g., temperature data transmission to a phone or other external device capable of displaying information).

A variety of different kinds of events may cause the (substantially error-free) user-initiated device activation componentry (30) to initiate power consumption. Of course, such componentry provides the benefit of preventing any battery power draw until a certain event, thereby preventing battery use during at least some period of time when the product is not in use, e.g., during pre-sale product storage, pre-sale product transportation, post-sale product storage, or pre-device insertion, etc. The configuration/design of the substantially error-free, user-initiated device activation componentry (30) will typically be governed by the event selected as the event that is to have initiating effect on the substantially error-free, user-initiated device activation componentry, thus initiating some sort of power mode (whether lower, full activation, initialization, or other) where some degree of battery power is consumed. In one embodiment, that event may be placement of the device (e.g., a ring) into a component (e.g., of packaging) such as but not limited to a cradle (36) (a component that, inter alia, is shaped to hold the device). Such event, which may occur after removal of the device from the position (in packaging) in which it is perhaps shipped and sold, may cause the switch to close via, e.g., attraction of a magnet located near such component (near, e.g., below or to the side of, a cradle) with a magnetic metal component of a magnetic switch, e.g., a magnetic reed switch located within the device as part of its circuitry, thereby, upon switch closure, initiating the flow of at least some power from the battery (a general term for any type of electrical power storage element). A magnetic switch may use magnetic attraction (between, e.g., iron or other magnetic metal and a permanent magnet, where one is in the switch and the other in a part of packaging that is proximate the iron or magnet in the switch) to keep a switch in one position until magnetic attraction forces it into the other position. Typically, the switch is in the device (ring) and the magnet is outside of it (e.g., under the cradle (36), or perhaps even in a wand (any sort of manually graspable contiguity) of sorts that includes the magnet).

Particular examples of events that may cause the (substantially error-free) user-initiated device activation componentry (30) to initiate battery power consumption include but are not limited to: certain types of mechanical action initiated by a user or other person (e.g., device removal from packaging (typically observed only in normally closed switch designs), device placement at a switch reconfiguration site such insertion into a cradle (36) (or other switch reconfiguration site (35), and typical of normally open switch designs), sufficient device bending as may be effected by a user just prior to insertion of the device into a vagina as intended, pressurization of the device, such as pressurization of the device at a certain marked site on the device so as to pressurize and close a switch, movement of the device (e.g., from packaging, as sensed perhaps by a mechanical movement sensor), package manipulation, and proximity condition change (as sensed perhaps by a mechanical or magnetic proximity sensor), and perhaps even wand movement in the proximity of the device). Note that user bending includes but is not limited to bending that closes a circuit either via either a bend that achieves a threshold stress that creates a "cracking" (e.g., as seen in prior art light sticks) or a gradual bending that does not cause such cracking, but merely effects switch closure after the bend crosses a threshold.

As mentioned, the (substantially error-free) user-initiated device activation componentry may include a switch that is open until the occurrence of an event. In particular embodiments, as discussed, that switch may be a magnetic switch, where magnetic attraction closes the switch upon the occurrence of the event. It may be a mechanical switch that is closed upon, e.g., sufficient bending of the device, or upon pressurization of a switch. In certain perhaps less preferable, but still inventive and offering value, embodiments, the switch may be a latching switch, which stays open until it is moved to the closed position (a "push" to make switch), and possibly back upon, e.g., instruction after a timer period expires, where it stays until it is moved to a different position (e.g., back to the open position). The switch may, e.g., be a latching, magnetic reed switch. Some such latching switch designs may require particular circuit configuration if a timer is indeed to cause termination of all power use upon expiration of a certain amount of time.

In certain embodiments, as alluded to above, the device (e.g., ring) is placed in the cradle (36) in, e.g., plastic housing (which is considered part of the packaging), via assistance of a visible marker (e.g., a black dot) on the outside of the device; such marker may facilitate/enable proper orientation of the device in the cradle (e.g., the black dot should face down into the cradle) such that when placed into the cradle, the magnetic reed switch will be in proper position relative to the magnet near the cradle (e.g., below, such as attached to the underside of the slot of the cradle in the plastic housing), i.e., sufficiently close to the magnet, so that the magnet will attract part of the switch and close the switch. In particular embodiments, once the reed switch is closed by the magnet, power may be applied to the microcontroller (from the battery(ies)) which then may close a FET switch (37) (once this FET switch is closed the reed switch can re-open without opening the closed circuit). Such circuit closure may cause the visually sense-able battery power-on indicator 16 to light up, whether blinking or otherwise. It may, as mentioned, cause a timer to initiate a countdown through a certain perhaps predesignated time period (where countdown includes a "count-up" and indeed any way of determining when a certain time period has elapsed).

Accordingly, upon placement of the device into the cradle 36, a visually sense-able, battery power-on indicator (16) (e.g., a LED light(s)), whether non-blinking, blinking, white, other colored, patterned-blinking, or otherwise, shines through clear silicone in the window (17) (e.g., filled hole), and out of that window so as to be visually sense-able to, e.g., a user. Note that the light(s), in certain embodiments, may have a distinguishable display (e.g., an non-blinking pattern, and an on/off blinking pattern; different colors, etc.) to indicate one or more different events or modes, e.g., when a ring is ready to be paired with an external device such as a phone, when a ring has successfully been paired with that external device, when it has communicated with an external device, when battery power is low, when it is in sleep mode, when it is in full activation power mode, when it is has a malfunction, etc.

Upon initial activation (e.g., upon placement of the device, such as a ring, into a "permanent magnet proximate cradle"), the light(s) may only remain on while it is advertising to pair. Once the ring is paired, the LED may shut off. If the ring is unable to pair within, e.g., (30) seconds, the device may be programmed so that the ring/LED shuts off. Typically, the LED (or other light) is not on during full activation power mode (e.g., when the device is able to measure and record temperatures, whether inside or outside of the vaginal vault) after pairing.

In particular embodiments, (e.g., cradle-type embodiments) an indication is given to the woman to remove the ring from the cradle once the LED quits flashing, which occurs when the MCU detects that the FET switch (generally a transistor (37)) is closed. The reed switch typically will be reopened when the device is removed from the cradle (because the magnetic is no longer near enough the magnetically attractive part of the reed switch to deflect it); because the FET switch closed the circuit is typically unaffected by the removal of the device from the cradle, the circuit remains powered after removal of the device from the cradle (and during its subsequent placement into a vaginal vault).

Note that, in certain embodiments, intended use is for a woman, after opening the package, to then grasp the ring and place it in the cradle to turn it on, at which point she can then pair it with her phone. Then shortly thereafter she can insert it into position so it can read and transmit temperatures. In some applications, it is recommended that users wait to insert until the first temperature readings are visible on the app so they know the ring is working correctly.

In certain embodiments, after removal from its inserted position (in the vaginal vault), the ring can be turned off by holding the magnet to the reed switch for a minimum of, e.g., 6 seconds. The microprocessor (26) may be programmed so that such that this will reset the ring, where all temperature measurements stored will be erased, or so that the device will simply be turned off.

In an embodiment that is different from but related to that embodiment where intentional placement into a cradle (that, e.g., is sufficiently close to a permanent magnet) initiates battery power flow, if the chosen event is removal of the device from packaging, then perhaps the substantially error-free, user-initiated device activation componentry (30) will, as but one example, include a magnetic (reed) switch to keep a battery-powered circuit open until the device (e.g., the vaginal temperature sensing ring (5)) is removed from the packaging (using a normally closed reed switch). Though not without its attendant disadvantages as discussed above, such may indeed be an aspect of certain embodiments of the inventive technology. Upon such removal, magnetic attraction no longer acts to keep the switch open, and the circuit is closed, allowing perhaps an eventual or immediate lower power (consumption) mode. As with a latching switch, in certain timer including embodiments, such may require particular circuitry configuration (that would be ascertainable to one of ordinary skill in the art) that would allow for a termination of battery power consumption in the event that, e.g., a communication link with an external device is not established.

In certain embodiments, when an event occurs to cause the user-initiated device activation componentry (30) to initiate/effect power consumption, the device may shift from shutdown mode (zero power draw from batter(ies)) to a power utilization mode, whether lower power mode, higher (full activation) power mode, device operation initialization mode, or other.

Note also that particular embodiments may include componentry that includes, e.g., sensors, electrical, thermal, light or otherwise, and/or timers, and/or pressure or bending activated switches that, after initial start of battery power consumption, may trigger a shift from a lower power, sleep mode to a full activation power mode where vaginal temperatures can actually be sensed (or back to a zero power consumption made, as explained). Some such embodiments may also include a thermal duration sensor (duration of temperature activated componentry), where the length of time the device is within a certain temperature range can be sensed. With such componentry, when typical vaginal temperatures are sensed for, e.g., an hour or more, then the device may shift from lower power mode to full activation power mode. Other electrical sensors that may be used include but are not limited to: magnetic field sensor, capacitive sensor, induction sensor, photoelectric sensor, moisture sensor, device flexure sensor, thermal sensor, pressure sensor, and optical sensor. Mechanical sensors and switches (e.g., bending or pressure-activated) may also be used.

The substantially error-free, user-initiated device activation componentry (30) may be further configured to be re-enabled at some point after it is reset (e.g., reset to open circuit position) upon occurrence of a re-enabling event. The event that causes such re-enabling may be sensed mechanically (e.g., a mechanical switch that is opened when the device is "unbent" (e.g., allowed to elastically return to its unbent, flat shape), or a switch that can be pressurized again to cause a closed switch to then open)), or even electrically, using any of a known variety of sensors (e.g., electrical thermal sensor, where temperatures below those observed in a vagina cause a switch to open, or proximity sensor, or moisture sensor). A normally open switch can return to its open position upon the absence of a certain condition (e.g., sufficiently high temperature, presence of moisture, magnetic attraction, etc.), where the switch remained closed only when the condition existed. A latching switch can be used where, e.g., instead of absence of a condition as the re-enabling event, it is desired that an intentional act (e.g., re-placement of the device into a component, e.g., a cradle, with a magnet nearby that opens the switch) re-enables the substantially error-free, user-initiated device activation componentry (30).

Note that certain embodiments may involve a type of redundant protection against unintentional/premature battery use (i.e., that occurring before an intended, pre-selected user-initiated event that causes the substantially error-free, user-initiated device activation componentry (30) to effect power consumption); such may be achieved using substantially error-free, user-initiated device activation componentry that effects power consumption only upon a primary event and secondary event (where the secondary event is a different event, perhaps even a different event type). An example includes device removal from package as the primary event, and bending of the device as the secondary event. Of course, two independent mechanical switches, likely in series, may be used to effect such redundancy. In certain embodiments, the events may each be unlikely events, whether occurring simultaneous or not (although this is not a requirement). Events may be such that, in particular embodiments, there is a 4, 5 or even 6 sigma probability (3.4 out of 1 million for 6 sigma probability) of the occurrence of both (i.e., one or the other, or both) in error.

A related vaginal temperature sensing method may comprise the steps of establishing a battery, vaginal temperature sensor componentry (24), and sensed vaginal temperature transmission componentry as part of temperature sensing electrical componentry; establishing non-conductive, flexible material proximate the temperature sensing electrical componentry; configuring user-initiated device activation componentry (30) to effect battery power consumption upon occurrence of an event; and possibly also configuring a timer (whether as part of or merely connected with a microprocessor (26)) to terminate battery power consumption upon elapse of a certain amount of time if a different event (e.g., communication between the device and an external device such as a phone) does not occur. Such activation componentry (30) may be substantially error-free. Other features this related method may be as disclosed elsewhere in this application.

Some embodiments may include power saving aspects. The device may record often, for example every 6 minutes, but may transmit, for example, only once every few hours. Measuring every few minutes may generate data often enough to be used to detect ovulation, fevers, etc. Transmitting upon every measurement, however, may use too much power as going through the connect process and communication may consume a lot of power relative to the power consumption of the other functions. Rapid transmission also may require the phone to be near the person more often to prevent losing data that may occur if the phone does not receive a transmission. To reduce power consumption and minimize issues with no connections with the phone, the device may log the temperature measurements for a period of time, for example 2.1 hours, and then attempt to connect and transmit temperature records, for example 22 logged temperature records. If a communication is established, the log of temperature records may be transmitted to the computer or phone. If no connection is acknowledged, the data may be stored, new temperatures may be continued to be measured and stored for an additional time period, for example 2.1 more hours, at which time another connection may be attempted. This process may be repeated, such as until a connection is made and all stored data is transferred. If the device does not connect to the phone for several days, and the data memory space in the device is filled, for example, in one embodiment for 1408 temperature measurements (or 5.8 days), the new temperature measurements may overwrite the old data so only oldest data is lost.

More particularly as to dimension, the Applicant indicates that, due to anatomical consideration and established standards, the size of a device may be constrained. One option is one that the FDA has already approved for a vaginal ring, such as 55 mm outer diameter, 46 mm inner diameter and a cross section of 9 mm. The dimensional, flexibility, twisting and survival requirements of the established standards may be met by the specific device design. Specifically, in some embodiments the design may include a flexible printed circuit substrate, perhaps 135 mm long, and perhaps having two short rigid sections and two flexible sections. One of the rigid sections may be located at one end of the substrate and the other may be in the center of the flexible substrate. Rigid sections may be required for mounting the electronic components, for example so that they are not damaged or the solder joints broken when the device is flexed or twisted per the above mentioned ISO 8009 standard. The rigid section on the end may contain components such as the batteries, the reed switch and power conditioning circuitry. The second rigid section, perhaps in the center of the substrate, may contain components such as the electronic components for the microcontroller, temperature sensor, temperature sensor conditioning circuitry and radio communication circuitry. One of the flexible sections may contain a component such as printed trace antenna, and the second flexible section may contain components such as conductors, for example, to connect the battery section to the electronics component section.

Note that any of the inventive technologies disclosed herein may be applied in fields other than vaginal temperature sensing. Such additional applications may be medically related in any fashion, including but not limited to internally inserted or ingested devices, or may be non-medical.

As can be appreciated, another aspect of embodiments of the invention can be the way the system processes data to achieve its purpose. Processing of data may be by software and or firmware, and for systems can be configured in a variety of ways and at a variety of locations. Devices and capabilities can be spread throughout the system as well. For example, in some embodiments the system can involve three major components. Each of these components can be configured as a discrete processor, a programmed dedicated processor, an ASIC, firmware, a device having programmable processing capability, a smart phone, a multipurpose computer, a server, or even internet or cloud computing capability.

In one embodiment, there can be a discrete device, such as some type of body contact device (91). In this embodiment, the body contact device (91) can communicate with a portable device (95). Further, the portable device (95) can communicate with perhaps what can be termed a server (97). This type of system is shown schematically in FIG. 17. As can be appreciated from the other discussion in this application, the body contact device (91) can be a compressible ring for a user such as an insertable item for a woman's body (101). In embodiments, this body contact device (91) can communicate wirelessly such a through a data transmitter (27) or as shown in FIG. 17, a general transmitter (93). This can be received by the portable device (95) which may be a smart phone. The smart phone can communicate via a cellular network, Bluetooth, the Internet, or otherwise perhaps with some more robust computing capability, such as a server (97) which can be a desktop or other computer capability.

As can be seen in FIG. 17, the body contact device (91) can include a variety of components such as for placement in or, more generally in contact with, a woman's body. It can include a processing capability or computer processor (105) that permits it to periodically capture data among other things. At this location, this processing capability can be generally considered a device processor (92) to differentiate it from other processing capabilities that mainly exist at other locations in the figures. The device processor (92) can be powered such as by battery (15) or (94) as shown in FIG. 17. The body contact device (91) can also include some type of sensor such as a periodic capture body temperature sensor (102). This element can act to periodically sense actual internal body temperature values such as at regular intervals (as set number of seconds, minutes, or the like) throughout at least a high temperature timeframe for a user. As can be appreciated the periodic capture body temperature sensor (102) can provide a multitude of individual data points and these can be stored at least temporarily locally on the body contact device (91) such as in an internal body temperature data memory (103) which can be responsive to the periodic capture internal body temperature sensor in obtaining its memory values. To store the correct values for embodiments of the invention, the internal body temperature data memory (103) can be configured to store a bracket of actual internal body temperature values. This configuration of the sensor and memory can allow embodiments to achieve storing a bracket of actual internal body temperature values that include at least the anticipated high temperature timeframe for the user. Further, the body contact device (91) can communicate, perhaps wirelessly, with another computer and capability, perhaps such as the portable device (95). This communication can be through inclusion of a data transmitter (27) or transmitter (93) that can transmit perhaps through the woman's body (101).

Communication can occur with a device that can be located close by, perhaps such as part of the person's carried personal effects or in their pocket or purse. This device can be generally considered a portable device (95) and it, too, may have a variety of capabilities. As can be understood the portable device (95) may even be a smart phone. The capabilities shown schematically in FIG. 17 can include some type of computer processor (105), perhaps considered even any app processor (96). Again, this processor can be quite programmable and the identification as an app processor may only distinguish its location. As an app processor (96), the device can execute a program, perhaps considered an application program or app, to achieve some type of operation. This and the other computer processors (105) can achieve data, capture, data storage, user input, or other operations. It can also transmit results, data, or other information to be able to interact with another processing capability. As shown in FIG. 17, one of the other components of such an embodiment of the system can be termed server (97). Again, it can just be a generally more capable or more available computer capability. The server (97) can also include general programmable capabilities and it may be or include a multipurpose programmable computer or processor. Communication can occur in standard fashions as mentioned above. The programmable or configurable capabilities or components in server (97) can include yet another computer processor (105) which may be termed server processor (98) to distinguish it main location as above. It can also access and interact with an internal or outside capability. This outside capability may be a memory and is shown in FIG. 17 as resource (99). The resource (99) can be a cloud storage capability, a cloud computing capability or the like. Again, memory and even processing capabilities can be distributed at various locales as is known to those in the art.

One of the unique aspects of the invention can be the manner in which the system processes, analyzes, and provides user information from or as a result of its data. In this aspect, the computer processor (105) can be understood as coupled to the internal body temperature data memory in a manner that uses those values to achieve its programmed purpose. The unique manners in which embodiment of the invention can take actual data and transform and recalculated may be achieved by inclusion of some type of automatic computer internal body temperature value transformer (126) in an automatic data transform recalculator (121). As should be appreciated, data processing, data pass-through, and/or data storage can occur at any location. In some preferred embodiments, only limited activity might occur in body contact device (91) to limit battery use and lengthen device life. As such, it may be preferable for embodiments to only provide temporary data storage, limited processing activity, and data transmission capability from the body contact device (91). Somewhat more complex activity can occur in portable device (95), but as is known, if this device is a smart phone, it may be desirable to limit activity in this device. In some embodiments, the most complex activity and most in-depth data storage—such as for multi users— can occur or be achieved at server (97).

Figure 18:
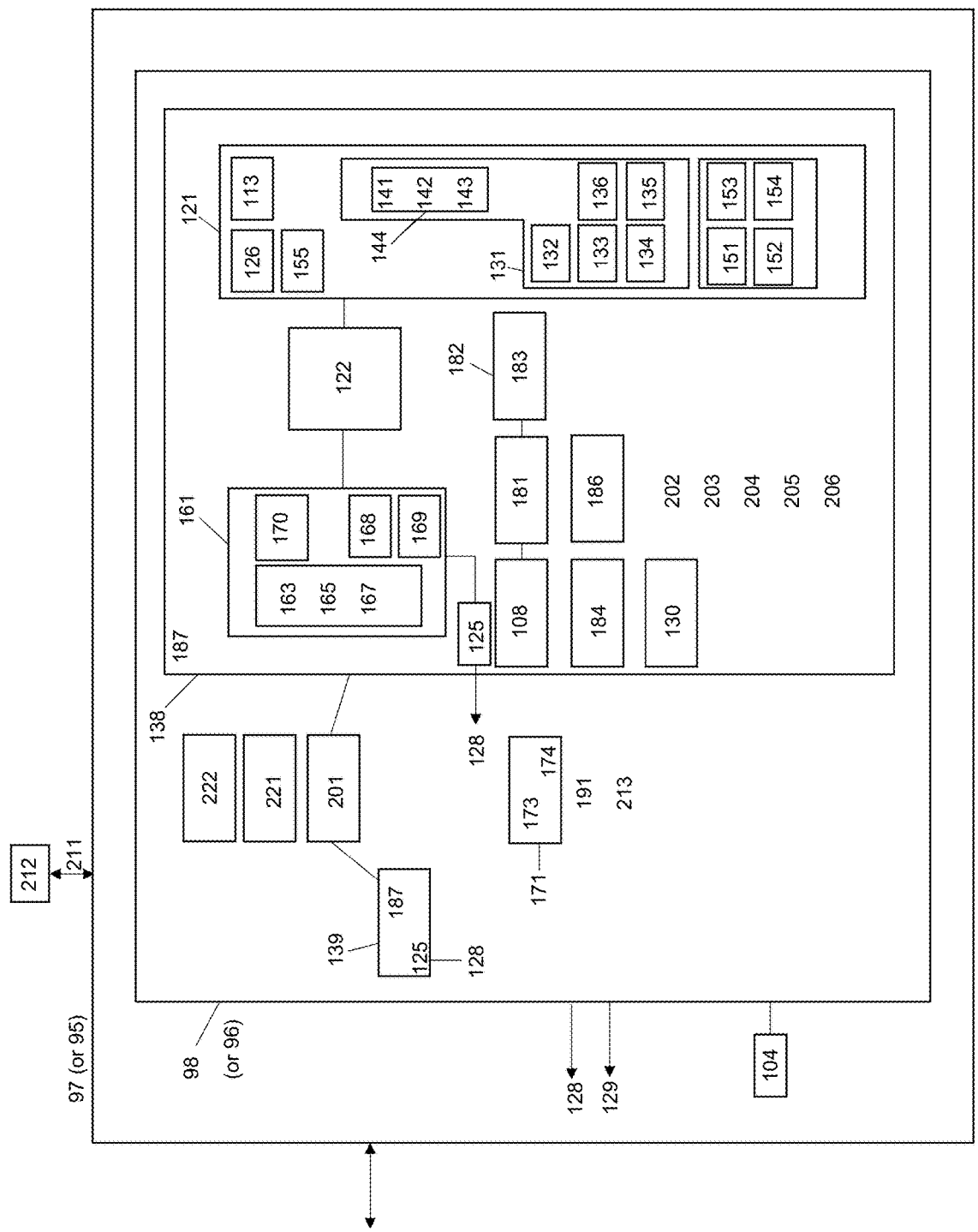
FIG. 18 is a schematic of one of the potential configurations with programming, subroutines, firmware, and processing capabilities shown in differing embodiments that may be combined.
Figure 19:
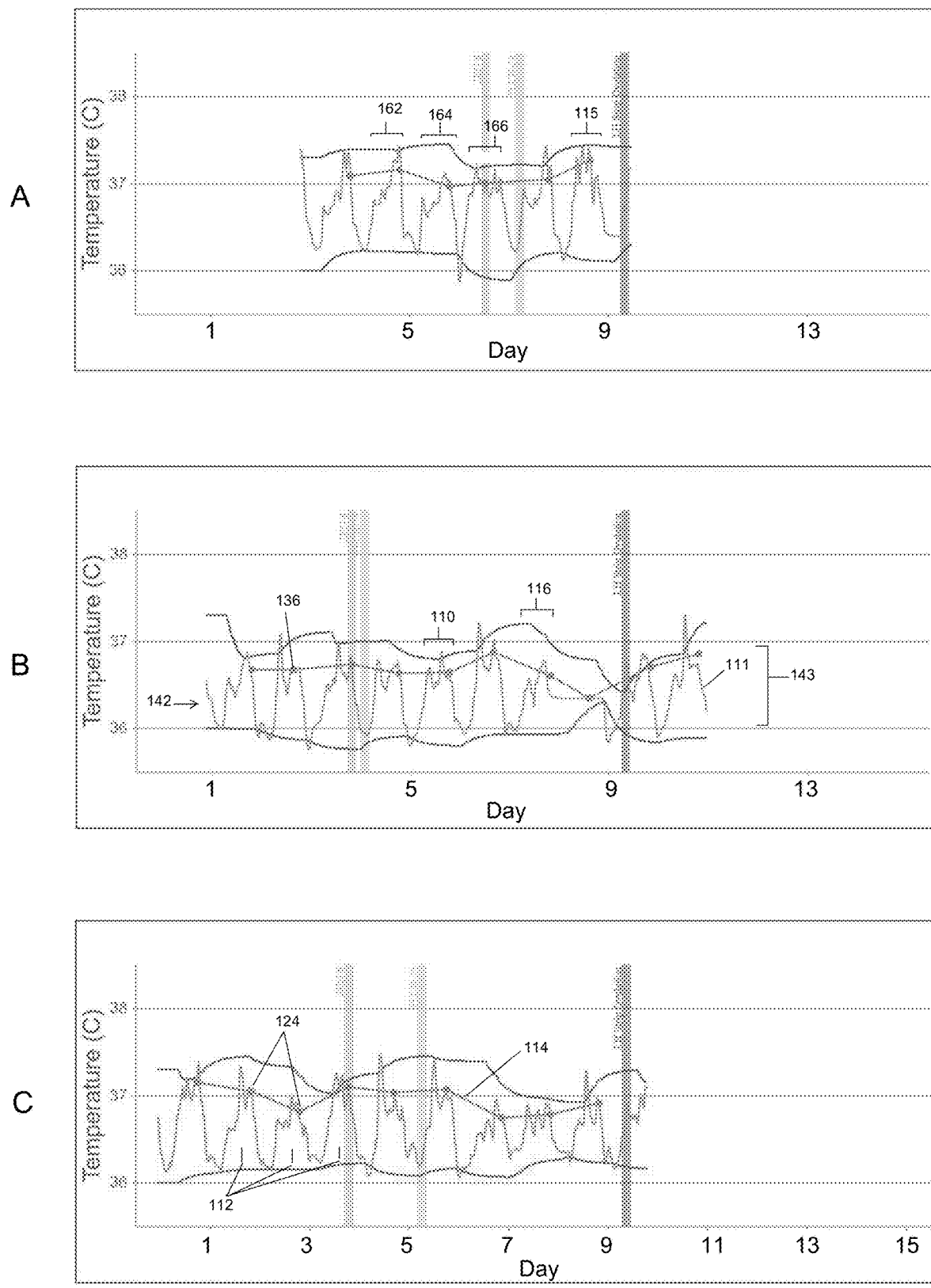
FIG. 19 shows actual temperature data as well as transformed and recalculated values to achieve some goals of differing embodiments of the invention.

An aspect of embodiments of invention can be the fact that instead of using the traditional basal temperature indications as a reference, embodiments of the invention may use daily zenith or high values for analysis. This may be counterintuitive but can be understood by reference to FIG. 19 where a plurality of actual internal body temperature values (111) is shown in the noisy data plots in FIGS. 19A, B, and C. As can be understood, body temperatures vary between day and night, or between times of activity and times of non-activity such as sleep. As shown in FIG. 19C, three active, likely diurnal periods are shown as those time frames indicated to be high temperature timeframes (112) as shown in FIG. 19C. Embodiments of the invention can use a bracket of actual internal body temperature values (110) as shown in FIG. 19 that is set to encompass high temperature timeframes (112). Such brackets of actual internal body temperature values can be used to determine the existence of an ovulation event as explained below. Thus, the computer processor (105) can be configured to act on the bracket of actual internal body temperature values in a manner that actually recalculates a daily zenith value from those values. These recalculated daily zenith values can be stored at least temporarily for later analysis such as storing them in a transformed estimated effective daily zenith created value memory (104) shown in FIG. 18. Significantly, these internal temperature values can be values associated with a daily high or daily zenith value. Aspects of embodiments of the invention can provide an automatic data transform recalculator (121) to analyze data within a bracket of actual internal body temperature values (110) to transform and recalculate such data in a manner that will achieve a transformed estimated effective daily zenith created value. As can be appreciated, the bracket of actual internal body temperature values (110) can be considered a bracket of diurnal internal body temperature values (115) (thus including daytime temperature values) or a bracket of awake period internal body temperature values (116) (thus including day-active as well as those night-active persons such as many emergency room physicians, and the like). Thus embodiments can act to automatically computer transform a bracket of diurnal internal body temperature values, or to automatically computer transform a bracket of awake period internal body temperature values.

As mentioned and shown in FIG. 19 (which is actual data), actual internal body temperature values can be noisy. This is especially true when daily, diurnal, or user active period data is used. An aspect of the invention which makes such data capable of being used is the fact that embodiments that include an automatic data transformer calculator (121) actually transform and recalculate the actual internal body temperature values to remove the noise and even create what is essentially a synthetic value, namely, a transformed estimated effective daily zenith created value (114). As can be seen for the three high temperature time frames (112) as shown in FIG. 19C, the transformed estimated effective daily zenith created values such as the two adjacent transformed estimated effective daily zenith created values (124) many bave little resemblance to the actual daily zenith sensed value. By using a created value aspect, embodiments of the present invention can make use of these time periods possible. Specifically, although in the past the focus was on basal temperature values (which are inherently less noisy), embodiments of the present invention show that by using even the noisy diurnal data, a created value can be achieved and surprisingly applied more accurately to often obtain even earlier indications of the existence of an ovulation event. In fact, the present invention shows that recalculating a daily zenith value can be used to great effect and that this can be superior to the traditional use of basal temperature data. Returning to the hardware designs of some embodiments, as shown in FIG. 18 the automatic data transform recalculator (121) can include programming that acts as an estimated daily zenith automatic data transform recalculator (113). Through appropriate programming, in some embodiments, the processor can be configured to automatically transform the bracket of actual internal body temperature values to automatically generate transformed estimated effective daily zenith created values. As mentioned the processor can be programmed to achieve automatically computer transforming data, perhaps such as the bracket of actual internal body temperature values, to recalculate a daily zenith value. The estimated damage zenith automatic data transform calculator (113) can provide the transformed estimated effective daily zenith created value (the dotted values such as (114) in the transformed recalculated data plots shown in FIGS. 19A, B, and C) for further analysis. In embodiments these transformed estimated effective daily zenith created values (114) can be a series of values such as shown with connected lines for better visualization in FIGS. 19A, B, and C. As mentioned, these individual values can be analyzed to determine whenever a dip occurs, and this dip in created values can be used as an indication of an ovulation event.

As shown in FIG. 19A, three data intervals, such as first data interval (162), second data interval (164), and third data interval (166) can be used to determine the existence of a dip. The determination can be made upon the existence of some raised level in adjacent values. For each of the data intervals, there can be programmed a corresponding data analyzer, thus embodiments can be considered to have a first data interval value analyzer (163), second data interval value analyzer (165), and a third data interval value analyzer (167) as shown in FIG. 18. An automatic estimated daily zenith dip calculator (170) such as by an adjacent transformed estimated effective daily zenith created value dip data processor (161) can be programmed to automatically computer analyze a first data interval value, a second data interval decrease value, and a third data interval increase value to make this determination. In some embodiments this determination can be made upon the completion of analyzing that particular third data interval and so some (perhaps especially the third data interval analyzer (167)) can be configured to be a full bracket of internal body temperature value analyzer (168) that automatically computer analyzes and reaches its determination after a full bracket of internal body temperature values have been gathered. Further, since dips can occur unrelated to ovulation, to increase accuracy, embodiments may include a likely time window since last ovulation event analyzer (169) to make the determination at more likely times perhaps such as 9 to 19 days after a last ovulation event determination. This can permit embodiments to factor in a likely time window since a last ovulation event for the user and increase accuracy in the event non-ovulation related temperature dips were to occur.

The determination of the existence of a dip in transformed and recalculated daily zenith values is shown by the first highlighted vertical bar in FIGS. 19A, B, and C. This represents the value for the time at which the determination can be made using this aspect of the invention. The second highlighted vertical bar represents the existence of a more traditional basal determination. The third highlighted vertical bar represents the existence of a non-temperature-based known way of determining ovulation, namely the luteinizing hormone test was of determination (which was previously considered the most reliable, however it may not remain that way after this invention becomes more widely received). Notably, by comparing the three vertical lines throughout FIGS. 19 A, B, and C, it can be seen at the earliest indication occurs with the present diurnal type of test as now described. As compared to more traditional basal temperature analysis, and even more traditional luteinizing hormone strip analysis, not only is the present invention an earlier indication, it does seem to be more accurate as well. Further as explained below other embodiments may even make it more accurate as further data is obtained. Since these plots represent actual data and actual determination, these particular plots show the significant improvement that embodiments of the present invention can achieve.

Referring to the hardware configurations of FIG. 18, it can be understood that the estimated daily zenith automatic data transform recalculator (113) can provide an output that can be generated by an automatic transformed estimated effective daily zenith created value generator (122). This can be sent to an automatic estimated daily zenith dip calculator (170) such as provided by an adjacent transformed estimated effective daily zenith created value dip data processor (161). This automatic transformed estimated effective daily zenith created value generator (122) can be arranged to be responsive to the computer processor operated automatic data transform recalculator (113) so it generates values that can be used in a potentially simplified manner. It can be configured to automatically analyze a succession of adjacent transformed estimated effective daily zenith created values and to determine the existence of a dip in the transformed estimated effective daily zenith created values. By programming, a processor can automatically computer analyze a succession of adjacent transformed estimated effective daily zenith created values and from this, act to determine the existence of a dip in the transformed estimated effective daily zenith created values. This can be used as an indication of the onset of an ovulation event as explained herein.

Of course, while these various processors and processing capabilities may be separate ASIC's or the like, these separate processors may be nothing but different programming routines to which a single microprocessor is responsive. Thus, these types of capabilities can be simply programming or even firmware arranged in either a general capability termed as server (97), a portable device (95), a single device that combines both of these capabilities, or distributed elsewhere. Further, in various embodiments, the programs can be configured to operate within the app processor (96) or the server processor (98) and so the schematic diagrams in FIG. 18 is shown as involving either processor. In some embodiments it may be desirable to provide calculational or other capability apart from the portable device (95). Such may be dependent on Internet or other communication accessibility as is now common (e.g., Alexa's voice recognition capability requires internet access). As accessibility and processing capabilities increase, it may be more desirable to move these capabilities apart or to a more centralized location, perhaps such as the server (97).

As shown in FIG. 18, ultimately, the output of elements such as the adjacent transformed estimated effective daily zenith created value dip data processor (161) can be provided to a transformed daily zenith ovulation prediction output generator (125) for user indication. The transformed daily zenith ovulation prediction output generator (125) can be arranged to be responsive to the adjacent transformed estimated effective daily zenith created value dip data processor as explained above. Further, this transformed daily zenith ovulation prediction output generator (125) can provide a signal to a zenith based ovulation indicator (106) which may even be in a different device. As shown in figure is 17 and 18, the processing capability can be on server (97), but the zenith based ovulation indicator (106) can be provided to a user more conveniently such as at their portable device (95) as shown in FIG. 17. In this manner embodiments can be programmed to automatically computer generate a transformed ovulation prediction output based on the act of automatically computer analyzing a succession of adjacent transformed estimated effective daily zenith created values and automatically determining a dip in the transformed estimated effective daily zenith created values. From these steps, the system can provide an ovulation indication at whatever location is desired.

As mentioned earlier, the data can be relatively noisy; this is evident from the actual data plots shown in FIGS. 19A, B, and C. To assist in achieving useful data, embodiments of the invention can include an automatic computer internal body temperature value smoother (131). In general and automatic computer internal body temperature value smoother (131) may be a functionality that is designed to endeavor to remove non-ovulation related temperature fluctuations from the actual internal body temperature values. As such, smoothing could be a way of achieving removal such fluctuations. As shown in FIG. 18, the automatic computer internal body temperature value smoother (131) could include an automatic computer estimated non-ovulation related temperature data fluctuation remover (144). This type of programming, firmware, ASIC, or routine could remove the non-ovulation related temperature fluctuations from use in achieving a transformed and recalculated value. Literal removal of data can occur by removing activity related data such as temperature fluctuations that are due to activities (e.g., exercise etc.), removing environmental related temperature fluctuations (e.g., effects from being outside on a cool or cold day and the like), removing short duration temperature fluctuations (perhaps regardless of their cause), removing higher frequency temperature fluctuation conversations, and the like. These types of steps of removing and types of removal elements can be included as separate routines or the like as shown in FIG. 18.

Other types of data removal are possible such as automatically removing and utilizing only threshold selected internal body temperature values (142) and utilizing the only window intermediate internal body temperature values (143). These are shown conceptually in FIG. 19B. As such, embodiments of the invention can include an automatic temperature internal body temperature value threshold selector (141) that acts to selected only desired data for use in the transformation and recalculation. As can be appreciated, these thresholds and windows can be varies, and can allow be operated on only a/the selected bracket of internal body temperature values.

One practical way of smoothing the data can be to utilize some type of average such as by inclusion of an automatic computer internal body temperature value averager (132). The automatic computer internal body temperature value averager (132) can yield a running or other computer internal body temperature value that can output a computer internal body temperature value running value average (136) such as shown in one example in FIG. 19B. The act of automatically computer averaging a bracket of internal body temperature values, can be achieved over a particular range of values. This aspect of utilizing a range of values can be significant in that the range can be varied to obtain a particular range that yields more reliable data. For example, one range that appears particularly useful and accurate for an ovulation event prediction is an eight hour range. Such a time window for the running average can also be varied and other values can be tested and utilized. As such, the automatic computer internal body temperature value averages (132) can be configured to provide an automatic computer internal body temperature value variable time window running value average (151). This average and running time window can be altered and a calculation can be made to provide a statistically optimized window with optimization potentially being on a number of criteria as discussed later. In these types of embodiments, the invention can be configured to achieve an automatic computer internal body temperature value statistically optimized the time window running value average (152). Program and system configurations can include an automatic computer internal body temperature value multiple running value average generator (153) that compares among different running value averages. It can then select the optimal by providing an automatic computer optimal running value average selector (154). The transformation and recalculation can then be achieved using a running average value estimated daily zenith automatic data transform recalculator (155) that applies the new selected running average.

One aspect of smoothing the data can be to eliminate data that appears with frequencies that are higher than some desired value. For example, aspects of the invention can include an automatic computer internal body temperature value frequency spectrum generator (133), an automatic computer internal body temperature value higher frequency eliminator (134), or an automatic computer internal body temperature value relevant frequency isolator (135). These elements can act to isolate or eliminate only desired frequencies. For example, data can be considered as existing as a composite of a number of different frequencies. For example, from use of a Fourier transform or the like, the actual data can be frequency spectrum analyzed and undesired frequencies eliminated or desired frequencies isolated for use. Given that many activity and many environmental occurrences that can lead to temperature fluctuations are usually more short-lived as compared to an ovulation event based temperature change (e.g., a period of hours versus a multi-day event), a frequency distinction can be of particular value. Such frequencies can be set at various levels. In embodiments of the invention, these frequencies can't be as follows—for frequency elimination, frequencies can be: frequencies greater than: one-half cycle/every thirty minutes frequency, one-half cycle/every hour frequency, one-half cycle/every two hours frequency, and one-half cycle/every three hours frequency; and correspondingly, the processor can be consider to include a greater than one-half cycle per every thirty minutes automatic computer internal body temperature value higher frequency eliminator; a less than one-half cycle per hour automatic computer internal body temperature value higher frequency eliminator; a less than one-half cycle per every two hours automatic computer internal body temperature value higher frequency eliminator; and a less than one-half cycle per every three hours automatic computer internal body temperature value higher frequency eliminator; for frequency isolation, frequencies can be: frequencies lower than: one-half cycle/every thirty minutes frequency, one-half cycle/every hour frequency, one-half cycle/every two hours frequency, and one-half cycle/every three hours frequency; and correspondingly, the processor can be consider to include a less than one-half cycle per every thirty minutes automatic computer internal body temperature value frequency isolator; a less than one-half cycle per hour automatic computer internal body temperature value frequency isolator; a less than one-half cycle per every two hours automatic computer internal body temperature value frequency isolator; and a less than one-half cycle per every three hours automatic computer internal body temperature value frequency isolator.

As mentioned in the foregoing relative to altering the range over which a running average may be calculated, it can be understood that aspects of the invention can be applied so that the system itself can automatically optimize its own internal processes. Similar to the manner in which the time range for a running average can be optimized, so too, can the system be configured to evaluate and compare different data transformation processes to select a more appropriate model. This can be accomplished not only for a then-available collection of information but also for particular users, for particular user demographics, and even a user's individual situation.

As shown in FIG. 17, for these types of embodiments a basic system can involve configuration aspects that can use computer capability at different locations in the system. For example, the portable device (95) can accept computer data from the sensor such in a manner that provides a computer data input (107). In an embodiment of the invention, this data can be used and applied to more than one data transform recalculator. Recalculators can be located at various processing capabilities within the overall system for example, as shown in FIG. 18, there can be more than one data transformer calculator at a server (97) or at a portable device (95). Considering two recalculators, there can be a first automatic data transformer calculator (138) and a second automatic data transformer calculator (139). Further the second automatic data transformer calculator (139) can, but need not be, be an identical recalculator as the first, although in this figure for simplicity the internal details are not shown as they are for the first. From this example with just two recalculators, it can be more readily understood how different data transforming recalculations can occur and how the system can act to compare the two and select between or include data from the two.

Such a system can be configured by programming, firmware, of use of an ASIC to automatically transform the internal body temperature values to provide a first or second transformation computation generated ovulation prediction output (128). For understanding but not as a limit, these outputs could perhaps be from a first or second transformed daily zenith ovulation prediction output generator (125) for those embodiments that also involve use of the other, daily zenith embodiments of the invention even though not required. Thus, it can be understood how such a system can automatically transform perhaps (but not necessarily) the same sensor computer data input (107) accessed values through a second transformation computation and use a second ovulation prediction output generator (125) to achieve, more generally, a second transformation computation generated ovulation prediction output (128). As shown, this can be in addition to the first transformation computation that uses the first ovulation prediction output generator (125) to achieve, again more generally, the first transformation computation generated ovulation prediction output (128). These two types of outputs can be compared and, depending upon the criteria selected or applied for a user, one or the other can be chosen as the one that is more likely to provide a user-preference aligned indication of the likely existence of an ovulation event.

The aspect of providing a more user-preference aligned indication can be achieved such as by programming or an element such as an automatic user high sense preference ovulation transformation comparator (171) as indicated in FIG. 18. This automatic user-preference ovulation transformation comparator (171) can act to automatically compare any number of a variety of generated ovulation prediction outputs, namely indications that can be used to determine the likely existence of an ovulation event. For example, as shown in FIG. 18, two or more different transforms can be compared such as by using the ovulation prediction output (128) by the automatic user-preference ovulation transformation comparator (171). A decision can be made by applying a variety of criteria that can be separately provided, for example, there can be a user-preference input (172) such as shown in FIG. 17 on the portable device (95). Through the user-preference input (172), a user or even general programming or a default stored input can provide a desired selection criterion. For example, if a user chooses, that user can select the earliest ovulation event indication as the desired criterion. In such a configuration, the automatic user-preference ovulation transformation comparator (171) can be configured as an earliest transformation indication ovulation transformation comparator (173). As but one other alternative, the user or a default setting could indicate a least false positive indication as the desired criterion. In this type of configuration, the system could be configured so as to be considered as having a least a false positive ovulation transformation comparator (174). Of course, other selection criteria could be provided including but not limited to criteria such as: higher probability of occurrence model selection or indication criteria, lower probability of occurrence model selection or indication criteria, lower conception probability onset criteria, higher conception probability onset criteria, most likely ovulation event occurrence criteria, possibly likely ovulation occurrence criteria and the like as the particular user-preference criteria. Ultimately, in such an embodiment, the final ovulation prediction output such as might result in a display to a user on their portable device (95) through inclusion of some type of ovulation indicator (106) (which could include but is not limited to being a zenith based ovulation indicator (106) for embodiments including that feature of the invention). Thus, embodiments of the system can be configured to achieve a desired comparison whatever it may be, and to provide that type of indication as optimally as possible for comparison among more than one different transformation recalculation process.

The example above shows one type of comparison, in general the system can be configured to provide indications that are peculiarly helpful or desirable to different particular users depending on their goals whether they be to achieve pregnancy, avoid pregnancy, or anticipate an upcoming activity. From the general ability to compare and select among different models or transformations, it can be understood that the system can be extended or use different configuration to include an ability to self-improve. The aspect of having a system that can automatically self-improve is particularly useful in the context of predicting an ovulation event. This can afford another independent aspect and another type of embodiment of this improved ovulation system. In this regard, the system can be configured to use its data perhaps in conjunction with other users' data or perhaps prior data for just that user to provide automatically enhanced and improved prediction routines. For example, as can be most easily understood from the earlier instance of using a variable range of values such as for a running average process, it can be understood that the ovulation transformation can be achieved through the application of ovulation transformation parameters (181). In that example, parameters can be considered perhaps the value(s) that represent the ranges of data points over which the running average would be calculated. Such ovulation transformation parameters (181) can be applied to the automatic data transform recalculator (121), and can be varied such as from a starting value (initially or at any reapplication of the process) for application such as by an ovulation transformation parameter vary routine (182) as shown in FIG. 18. Of course, by varying parameters, different results can be achieved. And these results can be compared automatically based on default or even user selected criteria such as by an automatic transformed ovulation prediction output comparator (191). Some types of ultimate or intermediate ovulation prediction outputs (128) can be made available automatically for comparison, or inclusion through combination of multiple transformations. The output can be considered an automatic transformed ovulation prediction output (129) regardless of the stage in the transformation or recalculation from which it is derived.

By storing the ovulation transformation parameters (181) in an ovulation transformation parameter memory (108), these parameters can be made available for later use, later variation, and even cumulative adjustment. When varied either initially or after cumulative improvement or the like, the system can be considered as applying varied ovulation transformation parameters (183) such as to achieve a varied ovulation data transform (184). There can be a starting ovulation data transform and then as a result of varying parameters, a varied ovulation data transform and this process can happen automatically. This varied ovulation data transformation (184) can provide an output that is used by an automatic varied transformation ovulation prediction outfit generator (130). As can be understood from the above, such a system can have an automatic transform the ovulation prediction output comparator (191) to allow decisions to be made based on the varied parameters applied.

In an iterative, self-improving process with a number of transformations, such embodiments can be considered as establishing an automated ovulation computational transform program with starting ovulation transformation parameters that may be at the beginning of any improvement process be it cumulative of just beginning initiation. Such starting transformation parameters can be applied to at least some of the internal body temperature values to automatically create a starting ovulation data transform. This starting ovulation data transform can generate an ovulation prediction output which can then be compared. Importantly, a comparison can be achieved by varying the starting ovulation transformation parameters to achieve a varied automated ovulation computational transformation which can be similarly applied to at least a portion of the internal body temperature values then available. Such a system can be configured to automatically compare the starting transformed ovulation prediction output, perhaps such as with the varied transform ovulation prediction output, to determine which of these is likely to provide a more user-preference aligned indication of the likely existence of an ovulation event. Once this decision is made, the selected parameters can then be stored and used perhaps as the next re-established starting ovulation transformation parameters so that continued system learning and improvement can build on itself by further revising and re-establishing desired parameters. These parameters can be cumulatively varied so that the system builds on itself as mentioned above. Cumulative variation can be achieved by using then-available data that includes some labeling or other ovulation indication, perhaps through a user-condition input (175) to assess what is likely most accurate. Determinations can also occur automatically even with computer determined weighting so that in some embodiments more recent data or perhaps more applicable data can be weighted heavier than other data. In general, cumulative improvement can be achieved by inclusion of a cumulative ovulation transformation parameter vary routine (186). Further, systems can include a neural network architecture capable of incorporating temperature data and other indications, perhaps such as discrete user data, user determined activity or occurrence data, clinical data, test data, LH test data, or the like, to allow improved predictions of likely ovulation events or to allow linkage to user preferences. Processing functions can take temperatures as input arguments and output ovulation predictions. By using temperature data that is correlated with ovulation test results or other indications, embodiments of the system can allow the computer to iteratively tune the weights in the neural network in such a way as to minimize an error function. Further, the error function may be any function of the difference between the neural network output and the ovulation test results. As more temperature data paired with ovulation test results or other indicia (call this "labeled data") becomes available, the system can automatically continue its iterative weight tuning process (called "training") to produce preferable ovulation event predictions on subsequent user cycles to yield a lower error as judged by the error function. There may also be several neural networks with different internal architectures and different error functions if desired. These can be re-trained whenever new data is available, and then re-compared with each other to see which is best, however that may be defined.

It should be understood that the parameters utilized can be simplistic or complex. More simplistic parameters can be considered as parameters like weights, ranges, coefficients, and other, perhaps linear, parameters. In addition, the parameters can be more complex and even non-linear. These can even include parameters that completely vary the entire nature of the transformation and recalculation itself. Regardless whether simplistic or complex, variation in parameters can consider or react to a user-preference input (172) which may be a default value. The system can make recommendations and even suggest alterations to or as a result of this input. Furthermore, the user can even have the option of providing a user-condition input (175) to which transformations, comparisons, and ovulation prediction outputs can be responsive.

Computer programming-wise, it can be understood that the system may be considered as including a multiple, a plurality, and any number of computer processor operated automatic data transform recalculators (187). Each of these can be configured to apply variable ovulation transformation parameters as mentioned above. Further, embodiments of the system can use the multiple transformation recalculations either in the alternative or as a composite way to provide a desired ovulation prediction output. In embodiments that combine or create a composite to provide a desired ovulation prediction output, the system can include an automatic transform recalculator combiner (201). This automatic transform recalculator combiner (201) can be responsive to a plurality of automatic transform re-calculators (187) which, again, may be identical capabilities that apply different parameters or may be entirely differently programmed recalculators. For clarity, it should be appreciated that the second, left, of the two of the plurality of depicted automatic data transform recalculators (187) is shown without depicting the internal details of the first, right, one but such may be and are likely included in each.

A further understanding of the way in which parameters can be varied can be understood by the more simplistic application of the running average transformation routine and the like as discussed above. Using this as but one example, as shown in FIG. 18, the system can include an ovulation transformation range size vary routine (202), an ovulation transformation range drift vary routine (203), an ovulation transformation threshold inclusion vary routine (204), an ovulation transformation coefficient vary routine (205), and/or an ovulation transformation weight vary routine (206). Of course, other variations are possible, and by inclusion of these types of processes and others, decisions and even some type of determination can be made based upon any desired optimization. Furthermore, the use of weight vary routines can show how a composite ovulation prediction output can be used with any number of transformations and any number of parameter variations with each having its own weight assigned to a total calculation or prediction output. Weighting of differing transforms can be particularly useful with consideration of the user-condition input (175) whereby user conditions that existed at that particular time can be applied or even removed to more appropriately achieve a prediction and perhaps even more appropriately apply then available multi user data to the situation then existing.

In its general sense, embodiments of the invention can involve a decision or prediction output that can be made on a combination of differing transforms, and a composite of various transforms. In just one general sense, an embodiment can involve a transform T, such as a first transform ($T_1$), a second transform ($T_2$), up to an $n^{th}$ transform ($T_n$) which can each be fundamentally different and can apply one or many persons' data. Further, each transform can have its own coefficient (constant, look up, function, or otherwise) to indicate any scaling such as for a particularly applicable factor (demographic, age, etc.) for that transform ($c_1$, $c_2$, $c_n$ so as to have $c_1T_1$, $c_2T_2$, $c_nT_n$) its own non-linear factor (indicated as a superscript, or power but not to be limited to such a mathematical process, $c_nT_n^1$, $c_nT_n^2$, $c_nT_n^m$), and a weight ($w_1$, $w_2$, $w_n$ so as to have $w_1c_1T_1$, $w_2c_2T_2$, $w_nc_nT_n$), and these can be used individually, in the alternative, or summed, added ($w_1c_1T_1+w_2c_2T_2+ \ldots w_nc_nT_n$) or otherwise combined as a composite to give an enhanced ovulation prediction output, $\rho$, perhaps such as $\rho=\Sigma\, w_nc_nT_n$. As can be appreciated, by understanding that weighting can even include zero weighting—meaning that that one transform is effectively removed from the process—any number of transformed recalculations, from one to many, can be included in a more general embodiment of the system. Such a composite can be interactively varied and evaluated to result in a continually self-improved system such as can be considered an instance of an artificial intelligence system or even a neural network based AI system as should be readily understood or separately available to a person of ordinary skill in the art.

One aspect that is particularly interesting for an ovulation prediction is the aspect of determining which result is the most optimal. This can be a challenge for an aspect such as predicting or onset sensing something as complex as ovulation which can be difficult to sense or know with certainty prior to its actual occurrence and which may be accompanied by discernable indicia only after the fact. As mentioned above, optimal-ness can be determined based upon a user selection or the like. In addition, the aspect of being optimal such as perhaps being earliest or perhaps most accurate, etc. can be achieved by comparison to a variety of data. This data can be a user condition input (175) perhaps such as, but not limited to, a user's input of physical symptoms indicating that ovulation is occurring. The data can also be a variety of other types of input perhaps, a prior computer input, a luteinizing hormone test computer input, a fertility test result computer input, a user menstrual cycle computer input, a user body type computer input, a user physical condition computer input, a user medical history computer input, a user text message computer input, and even a plurality of these various inputs.

In some embodiments, many user composite data can be used. This can be data such as may be contained in a many user composite database (212) as may perhaps be stored in resource (99). This can be accessed and used perhaps through a many user composite computer data input (211) to allow decisions to be made that are optimal based on a larger set of data. As mentioned earlier, the many user composite computer data input (211) can be a demographically grouped many user composite computer data input. This type of input can group or allow access to users demographically such as by ethnically grouping, prior pregnancy grouping, medication taken grouping, physical activity grouping, physical condition grouping, pre-existing medical condition grouping, or the like. Thus, the system can be considered as providing a computer data input that provides information as appropriate for that application.

Automated decisions on which output and which transformation is determined to be optimal can be made by using an error function analysis. In such a system, programming can be considered as configured to provide a minimum error value calculator (221) such as perhaps a minimum least squares value calculator (222) as should be well understood or available to persons of ordinary skill in the field. Again, as can be understood from the above where multiple embodiments can apply different aspects of the invention, each of these can be applied such as to provide in different embodiments. Embodiments can include any aspect with an estimated daily zenith automatic data transform recalculator or an estimated running average value estimated daily zenith automatic data transform recalculator among other examples. By providing a plurality of ovulation events prediction output comparator (213), applications such as a many user composite database can be considered and evaluated for applicability based on the system desired.

While the invention has been described in connection with some preferred embodiments, it is not intended to limit the scope of the invention to the particular form set forth, but on the contrary, it is intended to cover such alternatives, modifications, and equivalents as may be included within the spirit and scope of the invention as defined by the statements of inventions. Examples of alternative claims may include:

1. A vaginal temperature sensing apparatus comprising:
    a cured, flexible, outer ring shell made of first material;
    temperature sensing electrical componentry established in said cured, flexible, outer ring shell, said temperature sensing electrical componentry comprising a battery, vaginal temperature sensor componentry, and sensed vaginal temperature transmission componentry; and
    cured second material established within said cured, flexible, outer ring shell and between said temperature sensing electrical componentry and said cured, flexible, outer ring shell,
    wherein said cured second material and said cured, flexible, outer ring shell were cured during two distinct cures, said apparatus further comprising:
    user-initiated device activation componentry configured to start use of said battery power upon occurrence of an event; and
    a timer configured to start a countdown of a time period in response to said start of said use of said battery power,
    wherein said apparatus is configured to terminate said use of said battery power in the event of non-occurrence of establishment of a communication link between said apparatus and a different electronic device before the expiration of said time period.
2. A vaginal temperature sensing apparatus as described in clause 1, or any other clause, wherein said first material comprises first cure temperature material and said second material comprises second cure temperature material.
3. A vaginal temperature sensing apparatus as described in clause 1, or any other clause, wherein said apparatus comprises a ring.
4. A vaginal temperature sensing apparatus as described in clause 1, or any other clause, wherein said second material comprises transparent material.

5. A vaginal temperature sensing apparatus as described in clause 1, or any other clause, wherein said apparatus comprises a ring, wherein said temperature sensing electrical componentry further comprises a visually sense-able, batter power-on indicator, and wherein at least a portion of said transparent material is positioned so that light from said visually sense-able, battery power-on indicator passes through said at least a portion of said transparent material to outside of said ring.
6. A method of manufacturing a vaginal temperature sensing ring, comprising the steps of:
establishing a first material in a mold;
curing said first material in said mold at a first heating profile having a first maximum cure temperature, to form a cured, flexible, outer ring shell;
establishing an access opening in said cured, flexible outer ring shell;
inserting temperature sensing electrical componentry through said access opening and into said cured, flexible, outer ring shell;
establishing second material within said cured, flexible, outer ring shell to fill at least a portion of voids between said temperature sensing electrical componentry and said cured, flexible, outer ring shell; and
curing said second material at a second heating profile having a second maximum cure temperature, wherein said second maximum cure temperature is lower than said first maximum cure temperature.
7. A method of manufacturing a vaginal temperature sensing ring as described in clause 6, or any other clause, wherein said first material comprises a first cure temperature material and wherein said second material comprises a second cure temperature material.
8. A method of manufacturing a vaginal temperature sensing ring as described in clause 6, or any other clause, wherein said step of establishing second material within said cured, flexible, outer ring shell comprises the step of inserting said second material through said access opening.
9. A method of manufacturing a vaginal temperature sensing ring as described in clause 6, or any other clause, wherein said step of establishing an access opening in said cured, flexible outer ring shell comprises the step of establishing an access opening while performing said step of curing said first material in said mold.
10. A method of manufacturing a vaginal temperature sensing ring as described in clause 6, or any other clause, wherein said access opening comprises a circumferential slit.
11. A method of manufacturing a vaginal temperature sensing ring as described in clause 9, or any other clause, wherein said access opening comprises an inner circumferential slit.
12. A method of manufacturing a vaginal temperature sensing ring as described in clause 9, or any other clause, wherein said access opening comprises an outer circumferential slit.
13. A method of manufacturing a vaginal temperature sensing ring as described in clause 6, or any other clause, wherein said temperature sensing electrical componentry comprises a battery.
14. A method of manufacturing a vaginal temperature sensing ring as described in clause 13, or any other clause, wherein said battery is harmed when exposed to said first maximum cure temperature under said first heating profile but not when exposed to said second maximum cure temperature under said second heating profile.
15. A method of manufacturing a vaginal temperature sensing ring as described in clause 6, or any other clause, wherein said electronic componentry comprises a battery and a visually sense-able, battery power-on indicator electrically connected with said battery.
16. A method of manufacturing a vaginal temperature sensing ring as described in clause 6, or any other clause, and further comprising the step of establishing a window in said cured, flexible, outer ring shell.
17. A method of manufacturing a vaginal temperature sensing ring as described in clause 16, or any other clause, wherein said window is located immediately proximate where said visually sense-able, battery power-on indicator is established within said cured, flexible, outer ring shell.
18. A method of manufacturing a vaginal temperature sensing ring as described in clause 16, or any other clause, and further comprising the step of establishing said second material in said window.
19. A method of manufacturing a vaginal temperature sensing ring as described in clause 6, or any other clause, wherein said first material has a higher tensile strength than does said second material.
20. A method of manufacturing a vaginal temperature sensing ring as described in clause 6, or any other clause, wherein said second material is transparent after curing.
21. A method of manufacturing a vaginal temperature sensing ring as described in clause 6, or any other clause, wherein said second material is curable at a lower temperature than is said first material.
22. A method of manufacturing a vaginal temperature sensing ring as described in clause 6, or any other clause, wherein said first material and said second material are each a type of silicone.
23. A method of manufacturing a vaginal temperature sensing ring as described in clause 6, or any other clause, wherein said first material is medical grade material.
24. A method of manufacturing a vaginal temperature sensing ring as described in clause 23, or any other clause, wherein said first material is medical grade plastic.
25. A method of manufacturing a vaginal temperature sensing ring as described in clause 24, or any other clause, wherein said first material is a thermoplastic.
26. A method of manufacturing a vaginal temperature sensing ring as described in clause 23, or any other clause, wherein said first material is medical grade silicone.
27. A method of manufacturing a vaginal temperature sensing ring as described in clause 6, or any other clause, wherein said first material is opaque.
28. A method of manufacturing a vaginal temperature sensing ring as described in clause 6, or any other clause, wherein said second material is transparent.
29. A method of manufacturing a vaginal temperature sensing ring as described in clause 6, or any other clause, wherein said second material is medical grade material.
30. A method of manufacturing a vaginal temperature sensing ring as described in clause 29, or any other clause, wherein said second material is medical grade plastic.
31. A method of manufacturing a vaginal temperature sensing ring as described in clause 30, or any other clause, wherein said second material is a thermoplastic.
32. A method of manufacturing a vaginal temperature sensing ring as described in clause 29, or any other clause, wherein said second material is medical grade silicone.
33. A method of manufacturing a vaginal temperature sensing ring as described in clause 6, or any other clause, wherein said at least a portion of voids comprises at least a significant portion of voids.

34. A method of manufacturing a vaginal temperature sensing ring as described in clause 33, or any other clause, wherein said at least a significant portion of voids comprises at least a majority portion of voids.
35. A method of manufacturing a vaginal temperature sensing ring as described in clause 34, or any other clause, wherein said at least a majority portion of voids comprises substantially all voids.
36. A vaginal temperature sensing ring comprising:
a cured, flexible, outer ring shell made of first material;
temperature sensing electrical componentry established in said cured, flexible, outer ring shell; and
cured second material established within said cured, flexible, outer ring shell and between said temperature sensing electrical componentry and said cured, flexible, outer ring shell,
wherein said cured second material and said cured, flexible, outer ring shell were cured during two distinct cures.
37. A vaginal temperature sensing ring as described in clause 36, or any other clause, wherein said first material comprises a first cure temperature material and wherein said cured second material comprises a second cure temperature material.
38. A vaginal temperature sensing ring as described in clause 36, or any other clause, wherein said cured, flexible, outer ring shell comprises a sealed circumferential slit.
39. A vaginal temperature sensing ring as described in clause 36, or any other clause, wherein said temperature sensing electrical componentry comprises a battery.
40. A vaginal temperature sensing ring as described in clause 39, or any other clause, wherein said temperature sensing electrical componentry further comprises a visually sense-able, battery power-on indicator electrically connected with said battery.
41. A vaginal temperature sensing ring as described in clause 40, or any other clause, and further comprising a cured second material-filled window in said cured, flexible, outer ring shell.
42. A vaginal temperature sensing ring as described in clause 41, or any other clause, wherein said cured second material-filled window is located immediately proximate where said visually sense-able, battery power-on indicator is established within said cured, flexible, outer ring shell
43. A vaginal temperature sensing ring as described in clause 37, or any other clause, wherein said first material is opaque.
44. A vaginal temperature sensing ring as described in clause 37, or any other clause, wherein said cured second material is transparent.
45. A vaginal temperature sensing ring as described in clause 36, or any other clause, wherein said cured second material is of a different material type as compared with said first material.
46. A vaginal temperature sensing ring as described in clause 37, or any other clause, wherein said first material and said second material are identical material types.
47. A vaginal temperature sensing ring as described in clause 37, or any other clause, wherein said first material is medical grade silicone.
48. A vaginal temperature sensing ring as described in clause 37, or any other clause, wherein said first material has a higher tensile strength than does said cured second material.
49. A vaginal temperature sensing ring as described in clause 37, or any other clause, wherein said cured second material cures at a lower temperature than said first material.
50. A vaginal temperature sensing ring as described in clause 37, or any other clause, wherein said first material is medical grade material.
51. A vaginal temperature sensing ring as described in clause 50, or any other clause, wherein said first material is medical grade plastic.
52. A vaginal temperature sensing ring as described in clause 51, or any other clause, wherein said first material is a thermoplastic.
53. A vaginal temperature sensing ring as described in clause 50, or any other clause, wherein said first material is medical grade silicone.
54. A vaginal temperature sensing ring as described in clause 36, or any other clause, wherein said cured second material is medical grade material.
55. A vaginal temperature sensing ring as described in clause 54, or any other clause, wherein said cured second material is medical grade plastic.
56. A vaginal temperature sensing ring as described in clause 55, or any other clause, wherein said cured second material is a thermoplastic.
57. A vaginal temperature sensing ring as described in clause 54, or any other clause, wherein said cured second material is medical grade silicone.
58. A vaginal temperature sensing ring comprising:
temperature sensing electrical componentry that comprises a battery and a visually sense-able, battery power-on indicator electrically connected with said battery; and
flexible, non-conductive vaginal ring material in which said temperature sensing electrical componentry is established, said flexible, non-conductive vaginal ring material comprising transparent, vaginal ring material and non-transparent vaginal ring material,
wherein at least a portion of said transparent, vaginal ring material is positioned so that light from said visually sense-able, battery power-on indicator passes through said at least a portion of said transparent vaginal ring material to outside of said vaginal temperature sensing ring.
59. A vaginal temperature sensing ring as described in clause 58, or any other clause, wherein said visually sense-able, battery power-on indicator comprises a LED.
60. A vaginal temperature sensing ring as described in clause 58, or any other clause, wherein said at least a portion of said transparent vaginal ring material is established between said visually sense-able, battery power-on indicator and an outwardly exposed surface of said vaginal temperature sensing ring.
61. A vaginal temperature sensing ring as described in clause 58, or any other clause, and further comprising a window through which said light passes to outside of said vaginal temperature sensing ring.
62. A vaginal temperature sensing ring as described in clause 61, or any other clause, wherein said at least a portion of said transparent vaginal ring material positioned so that light passes to outside of said vaginal temperature sensing ring is established in said window.
63. A vaginal temperature sensing ring as described in clause 62, or any other clause, wherein said non-transparent vaginal ring material comprises cured, flexible, outer ring shell material.
64. A vaginal temperature sensing ring as described in clause 63, or any other clause, wherein said window is created through said cured, flexible, outer ring shell material.

65. A vaginal temperature sensing ring as described in clause 64, or any other clause, wherein said transparent vaginal ring material comprises void filling material and window filling material.

66. A vaginal temperature sensing ring as described in clause 63, or any other clause, wherein said window is a transparent, vaginal ring material-filled window.

67. A vaginal temperature sensing ring as described in clause 61, or any other clause, wherein said window comprises a small window.

68. A vaginal temperature sensing ring as described in clause 67, or any other clause, wherein said window is just large enough to allow light from said indicator to pass through said window to outside of said vaginal temperature sensing ring so said light can be visually noticed by a user.

69. A vaginal temperature sensing ring as described in clause 67, or any other clause, wherein said window is just large enough to allow injection therethrough of said transparent, vaginal ring material.

70. A vaginal temperature sensing ring as described in clause 66, or any other clause, wherein light from said indicator passes through said transparent, vaginal ring material-filled window.

71. A vaginal temperature sensing ring as described in clause 58, or any other clause, wherein said flexible, non-conductive vaginal ring material comprises silicone.

72. A vaginal temperature sensing ring as described in clause 58, or any other clause, wherein said non-transparent vaginal ring material comprises first cure temperature material.

73. A vaginal temperature sensing ring as described in clause 72, or any other clause, wherein said transparent vaginal ring material comprises second cure temperature material.

74. A vaginal temperature sensing ring as described in clause 58, or any other clause, wherein said non-transparent vaginal ring material comprises a first material and said transparent vaginal ring material comprises a second material.

75. A vaginal temperature sensing ring as described in clause 58, or any other clause, wherein said temperature sensing electrical componentry further comprises a temperature sensor and an antenna.

76. A vaginal temperature sensing ring as described in clause 75, or any other clause, wherein said temperature sensing electrical componentry further comprises a microprocessor, data transmitter and signal receiver.

77. A vaginal temperature sensing ring method comprising the steps of:
establishing temperature sensing electrical componentry in flexible, non-conductive vaginal ring material, said temperature sensing electrical componentry comprising a battery and a visually sense-able, battery power-on indicator electrically connected with said battery;
wherein said flexible, non-conductive vaginal ring material comprises transparent, vaginal ring material; and
positioning at least a portion of said transparent, vaginal ring material so that light from said visually sense-able, battery power-on indicator passes through said at least a portion of said transparent vaginal ring material to outside of said vaginal temperature sensing ring.

78. A vaginal temperature sensing ring method as described in clause 77, or any other clause, wherein said visually sense-able, battery power-on indicator comprises a LED.

79. A vaginal temperature sensing ring method as described in clause 77, or any other clause, wherein said at least a portion of said transparent vaginal ring material is established between said visually sense-able, battery power-on indicator and an outwardly exposed surface of said vaginal temperature sensing ring.

80. A vaginal temperature sensing ring method as described in clause 77, or any other clause, and further comprising the step of curing a flexible, outer vaginal ring shell.

81. A vaginal temperature sensing ring method as described in clause 80, or any other clause, and further comprising the step of creating a window through said flexible, outer vaginal ring shell.

82. A vaginal temperature sensing ring method as described in clause 81, or any other clause, wherein said step of creating a window comprises the step of creating a window at a visually sense-able, battery power-on indicator location.

83. A vaginal temperature sensing ring method as described in clause 81, or any other clause, wherein said step of positioning at least a portion of said transparent, vaginal ring material so that light from said visually sense-able, battery power-on indicator passes through said at least a portion of said transparent vaginal ring material to outside of said vaginal temperature sensing ring comprises the step of positioning said at least a portion of said transparent, vaginal ring material in said window.

84. A vaginal temperature sensing ring method as described in clause 77, or any other clause, wherein said flexible, non-conductive vaginal ring material further comprises non-transparent vaginal ring material.

85. A vaginal temperature sensing ring method as described in clause 84, or any other clause, wherein said non-transparent vaginal ring material comprises first cure temperature material that is curable at a first cure temperature.

86. A vaginal temperature sensing ring method as described in clause 85, or any other clause, wherein said transparent vaginal ring material comprises second cure temperature material that is curable at a second cure temperature material that is lower than said first cure temperature.

87. A vaginal temperature sensing ring method as described in clause 77, or any other clause, wherein said temperature sensing electrical componentry further comprises a temperature sensor and an antenna.

88. A vaginal temperature sensing ring method as described in clause 87, or any other clause, wherein said temperature sensing electrical componentry further comprises a microprocessor, data transmitter, and a signal receiver.

89. A vaginal temperature sensor apparatus comprising:
temperature sensing electrical componentry comprising a battery, vaginal temperature sensor componentry, and sensed vaginal temperature transmission componentry;
flexible, non-conductive material proximate said temperature sensing electrical componentry;
user-initiated device activation componentry configured to start use of said battery power upon occurrence of an event;
a timer configured to start a countdown of a time period in response to said start of said use of said battery power,
wherein said apparatus is configured to terminate said use of said battery power in the event of non-occurrence of establishment of a communication link between said apparatus and a different electronic device before the expiration of said time period.

90. A vaginal temperature sensor apparatus as described in clause 89, or any other clause, wherein at least part of said apparatus forms a ring.

91. A vaginal temperature sensor apparatus as described in clause 90, or any other clause, wherein a portion of said user-initiated device activation componentry is established outside of said ring.
92. A vaginal temperature sensor apparatus as described in clause 91, or any other clause, wherein said user-initiated device activation componentry comprises a permanent magnet and a magnetic reed switch.
93. A vaginal temperature sensor apparatus as described in clause 92, or any other clause, wherein said permanent magnet is established close enough to a switch reconfiguration site so that, when said ring is placed at said switch reconfiguration site, said magnetic reed switch reconfigures.
94. A vaginal temperature sensor apparatus as described in clause 93, or any other clause, wherein said magnetic reed switch reconfigures from an open condition to a closed condition when said ring is placed at said switch reconfiguration site.
95. A vaginal temperature sensor apparatus as described in clause 93, or any other clause, wherein said switch reconfiguration site comprises a cradle.
96. A vaginal temperature sensor apparatus as described in clause 89, or any other clause, wherein said apparatus is further configured to terminate said use of said battery power in the event of failure to establish a communication link between said apparatus and a computing device that remains external of a body of said user when said apparatus is established internally of said body in order to sense temperature.
97. A vaginal temperature sensor apparatus as described in clause 96, or any other clause, wherein said computing device comprises an electronic device selected from the group consisting of cell phone, a tablet, a laptop and a watch.
98. A vaginal temperature sensor apparatus as described in clause 89, or any other clause, further comprising a transistor, wherein said apparatus is configured to switch a transistor to closed configuration upon said start of use of said battery power.
99. A vaginal temperature sensor apparatus as described in clause 98, or any other clause, wherein said transistor is a FET.
100. A vaginal temperature sensor apparatus as described in clause 98, or any other clause, wherein said apparatus is further configured to leave said transistor in said closed configuration at said expiration of said time period if said communication link is established.
101. A vaginal temperature sensor apparatus as described in clause 89, or any other clause, wherein said flexible, non-conductive material proximate said temperature sensing electrical componentry and at least part of said battery power use prevention componentry forms a vaginal temperature sensing ring.
102. A vaginal temperature sensor apparatus as described in clause 89, or any other clause, wherein said flexible, non-conductive material comprises closed curvilinear shaped material.
103. A vaginal temperature sensor apparatus as described in clause 102, or any other clause, wherein said closed curvilinear shaped material comprises ring shaped material.
104. A vaginal temperature sensor apparatus as described in clause 89, or any other clause, wherein said user-initiated device activation componentry comprises substantially error-free user-initiated device activation componentry.
105. A vaginal temperature sensor apparatus as described in clause 104, or any other clause, wherein said event comprises an event selected so as to substantially eliminate possibility of premature disablement of said substantially error-free, battery power use prevention componentry.
106. A vaginal temperature sensor apparatus as described in clause 105, or any other clause, wherein said event comprises a human-initiated event.
107. A vaginal temperature sensor apparatus as described in clause 106, or any other clause, wherein said event comprises a user-initiated event.
108. A vaginal temperature sensor apparatus as described in clause 104, or any other clause, wherein said event is selected so that said substantially error-free, battery power use prevention componentry is not disabled during pre-sale device transportation or storage.
109. A vaginal temperature sensor apparatus as described in clause 104, or any other clause, wherein said event comprises a user-caused mechanical action.
110. A vaginal temperature sensor apparatus as described in clause 109, or any other clause, wherein said event comprises sufficient device bending.
111. A vaginal temperature sensor apparatus as described in clause 109, or any other clause, wherein said event comprises sufficient device pressurization.
112. A vaginal temperature sensor apparatus as described in clause 111, or any other clause, wherein said event comprises sufficient switch pressurization.
113. A vaginal temperature sensor apparatus as described in clause 109, or any other clause, wherein said event comprises device placement into a cradle.
114. A vaginal temperature sensor apparatus as described in clause 113, or any other clause, wherein said cradle is a part of device packaging.
115. A vaginal temperature sensor apparatus as described in clause 109, or any other clause, wherein said event comprises package manipulation.
116. A vaginal temperature sensor apparatus as described in clause 109, or any other clause, wherein said event comprises proximity condition change.
117. A vaginal temperature sensor apparatus as described in clause 109, or any other clause, wherein said event comprises movement of a wand.
118. A vaginal temperature sensor apparatus as described in clause 98, or any other clause, wherein said user-initiated device activation componentry comprises a normally open switch.
119. A vaginal temperature sensor apparatus as described in clause 118, or any other clause, wherein said normally open switch comprises a magnetic read switch.
120. A vaginal temperature sensor apparatus as described in clause 98, or any other clause, and further comprising a visually sense-able, battery power-on indicator connected with said battery.
121. A vaginal temperature sensor apparatus as described in clause 120, or any other clause, wherein said visually sense-able, battery power-on indicator comprises a LED.
122. A vaginal temperature sensor apparatus as described in clause 121, or any other clause, wherein said LED comprises a short duration LED.
123. A vaginal temperature sensing method comprising the steps of:
    establishing a battery, vaginal temperature sensor componentry, and sensed vaginal temperature transmission componentry as part of temperature sensing electrical componentry;

establishing flexible, non-conductive material proximate said temperature sensing electrical componentry;

configuring user-initiated device activation componentry to start use of said battery power upon occurrence of an event;

configuring a timer to a start countdown of a time period in response to said start of said use of said battery power, wherein said temperature sensing electrical componentry, said flexible, non-conductive material, said timer and at least part of said user-initiated device activation componentry are configured to form a device shaped for insertion into a vagina of said user;

configuring electrical componentry to terminate said use of said battery power in the event of non-occurrence of establishment of a communication link between said device and a different electronic device before the expiration of said time period.

124. A vaginal temperature sensing method as described in clause 123, or any other clause, wherein said device is a ring.

125. A vaginal temperature sensing method as described in clause 123, or any other clause, wherein said step of configuring user-initiated device activation componentry comprises the step of configuring a portion of said user-initiated device activation componentry to be outside of said device.

126. A vaginal temperature sensing method as described in clause 125, or any other clause, wherein said step of configuring user-initiated device activation componentry comprises the step of configuring a permanent magnet and a magnetic reed switch.

127. A vaginal temperature sensing method as described in clause 126, or any other clause, wherein said step of configuring user-initiated device activation componentry comprises the step of configuring said permanent magnet close enough to a switch reconfiguration site so that, when said ring is placed at said switch reconfiguration site, said magnetic reed switch reconfigures.

128. A vaginal temperature sensing method as described in clause 127, or any other clause, wherein, when said ring is placed at said switch reconfiguration site, said magnetic reed switch reconfigures from an open configuration to a closed configuration.

129. A vaginal temperature sensing method as described in clause 123, or any other clause, wherein said step of configuring electrical componentry comprises the step of configuring electrical componentry to terminate said use of said battery power in the event of non-occurrence of establishment of a communication link between said device shaped for insertion into a vagina of said user and an electronic device that remains external of a body of said user.

130. A vaginal temperature sensing method as described in clause 123, or any other clause, further comprising the step of configuring electrical componentry to switch a transistor to closed configuration upon said start of use of said battery power.

131. A vaginal temperature sensing method as described in clause 130, or any other clause, further comprising the step of configuring said electrical componentry to leave said transistor in said closed configuration at said expiration of said time period if said communication link is established.

132. A vaginal temperature sensing method as described in clause 123, or any other clause, wherein said step of configuring user-initiated device activation componentry comprises the step of configuring user-initiated device activation componentry to start use of said battery power upon occurrence of a user-caused mechanical event.

133. A vaginal temperature sensing method as described in clause 132, or any other clause, wherein said user-caused mechanical event comprises placement of said device at a switch reconfiguration site.

134. A vaginal temperature sensing method as described in clause 133, or any other clause, wherein said placement of said device at a switch reconfiguration site comprises placement of said device at a site that effects switch reconfiguration from an open configuration to a closed configuration.

135. A vaginal temperature sensing method as described in clause 133, or any other clause, wherein said placement of said device at a switch reconfiguration site comprises placement of said device in a cradle.

136. A vaginal temperature sensing method as described in clause 133, or any other clause, wherein said placement of said device at a switch reconfiguration site comprises movement of a wand that comprises a permanent magnet sufficiently close to said device.

137. A vaginal temperature sensing method as described in clause 123, or any other clause, wherein said step of configuring user-initiated device activation componentry comprises the step of configuring componentry that comprises a permanent magnet and a magnetically reconfigurable switch.

138. A vaginal temperature sensing method as described in clause 137, or any other clause, wherein said magnetically reconfigurable switch comprises a magnetic reed switch.

139. A vaginal temperature sensing method as described in clause 123, or any other clause, further comprising the step of configuring a visually sense-able, battery power-on indicator to indicate said use of said battery power at at least some point in time during said use of said battery power.

140. A vaginal temperature sensor apparatus comprising:
temperature sensing electrical componentry comprising a battery, vaginal temperature sensor componentry, and sensed vaginal temperature transmission componentry;
flexible, non-conductive material proximate said temperature sensing electrical componentry; and
substantially error-free, user-initiated device activation componentry configured to start use of said battery power upon occurrence of an event.

141. A vaginal temperature sensor apparatus as described in clause 140, or any other clause, wherein said flexible, non-conductive material proximate said temperature sensing electrical componentry and at least part of said substantially error-free, user-initiated device activation componentry forms at least part of a vaginal temperature sensing ring.

142. A vaginal temperature sensor apparatus as described in clause 140, or any other clause, wherein said flexible, non-conductive material comprises closed curvilinear shaped material.

143. A vaginal temperature sensor apparatus as described in clause 142, or any other clause, wherein said closed curvilinear shaped material comprises ring shaped material.

144. A vaginal temperature sensor apparatus as described in clause 140, or any other clause, wherein said temperature sensing electrical componentry further comprises an antenna.

145. A vaginal temperature sensor apparatus as described in clause 144, or any other clause, wherein said antenna is established along only a less than 30% portion of a device centerline.

146. A vaginal temperature sensor apparatus as described in clause 145, or any other clause, wherein said device centerline is a ring centerline.

147. A vaginal temperature sensor apparatus as described in clause 144, or any other clause, wherein said antenna is established along substantially all of a device centerline.

148. A vaginal temperature sensor apparatus as described in clause 147, or any other clause, wherein said device centerline is a ring centerline.

149. A vaginal temperature sensor apparatus as described in clause 144, or any other clause, wherein said temperature sensing electrical componentry is flexible.

150. A vaginal temperature sensor apparatus as described in clause 140, or any other clause, wherein said temperature sensing electrical componentry further comprises a signal receiver.

151. A vaginal temperature sensor apparatus as described in clause 140, or any other clause, wherein said flexible, non-conductive material is established substantially around said temperature sensing electrical componentry.

152. A vaginal temperature sensor apparatus as described in clause 140, or any other clause, wherein said substantially error-free, user-initiated device activation componentry is configured so that, upon said occurrence of an event, said apparatus initiates entry into a lower power mode.

153. A vaginal temperature sensor apparatus as described in clause 152, or any other clause, wherein said lower power mode is observed after an initialization power mode.

154. A vaginal temperature sensor apparatus as described in clause 152, or any other clause, wherein said lower power mode is a sleep mode power mode.

155. A vaginal temperature sensor apparatus as described in clause 140, or any other clause, wherein said substantially error-free, user-initiated device activation componentry is configured so that, upon said occurrence of an event, said apparatus initiates enablement of vaginal temperature sensing.

156. A vaginal temperature sensor apparatus as described in clause 155, or any other clause, wherein said substantially error-free, user-initiated device activation componentry is configured so that, upon said occurrence of an event, said apparatus initiates enablement of data transmission and signal monitoring.

157. A vaginal temperature sensor apparatus as described in clause 156, or any other clause, wherein said signal monitoring and said data transmission is achieved via Bluetooth.

158. A vaginal temperature sensor apparatus as described in clause 140, or any other clause, wherein said event comprises an event selected so as to substantially eliminate possibility of premature initiation of said substantially error-free, user-initiated device activation componentry.

159. A vaginal temperature sensor apparatus as described in clause 158, or any other clause, wherein said event comprises a human-initiated event.

160. A vaginal temperature sensor apparatus as described in clause 159, or any other clause, wherein said event comprises a user-initiated event.

161. A vaginal temperature sensor apparatus as described in clause 158, or any other clause, wherein said event is selected so that said substantially error-free, user-initiated device activation componentry is not initiated during pre-sale device transportation or storage.

162. A vaginal temperature sensor apparatus as described in clause 158, or any other clause, wherein said substantially error-free, user-initiated device activation componentry comprises a thermocouple.

163. A vaginal temperature sensor apparatus as described in clause 158, or any other clause, wherein said event comprises a user-caused mechanical action.

164. A vaginal temperature sensor apparatus as described in clause 163, or any other clause, wherein said event comprises sufficient device bending.

165. A vaginal temperature sensor apparatus as described in clause 163, or any other clause, wherein said event comprises sufficient device pressurization.

166. A vaginal temperature sensor apparatus as described in clause 165, or any other clause, wherein said event comprises sufficient switch pressurization.

167. A vaginal temperature sensor apparatus as described in clause 163 wherein said event comprises device removal from packaging.

168. A vaginal temperature sensor apparatus as described in clause 163 wherein said event comprises device placement into a cradle.

169. A vaginal temperature sensor apparatus as described in clause 168 wherein said cradle is a part of device packaging.

170. A vaginal temperature sensor apparatus as described in clause 163 wherein said event comprises package manipulation.

171. A vaginal temperature sensor apparatus as described in clause 163 wherein said event comprises proximity condition change.

172. A vaginal temperature sensor apparatus as described in clause 140 wherein said event comprises device removal from packaging.

173. A vaginal temperature sensor apparatus as described in clause 172 wherein said event comprises movement of at least portion of said apparatus.

174. A vaginal temperature sensor apparatus as described in clause 140 wherein said event comprises movement of at least a portion of said apparatus.

175. A vaginal temperature sensor apparatus as described in clause 140 wherein said event comprises movement of a wand.

176. A vaginal temperature sensor apparatus as described in clause 140 wherein said substantially error-free, user-initiated device activation componentry comprises a switch that is open until said occurrence of an event.

177. A vaginal temperature sensor apparatus as described in clause 176 wherein said switch comprises a proximity switch.

178. A vaginal temperature sensor apparatus as described in clause 177 wherein said proximity switch comprises a magnetic reed switch and magnetic attraction keeps said switch open until said occurrence of said event.

179. A vaginal temperature sensor apparatus as described in clause 178, or any other clause, wherein said substantially error-free, user-initiated device activation componentry comprises a permanent magnet.

180. A vaginal temperature sensor apparatus as described in clause 176, or any other clause, wherein said switch comprises a latching switch.

181. A vaginal temperature sensor apparatus as described in clause 140, or any other clause, wherein said substantially error-free, user-initiated device activation componentry comprises a latching switch.

182. A vaginal temperature sensor apparatus as described in clause 181, or any other clause, wherein said latching switch is closed upon said occurrence of said event.
183. A vaginal temperature sensor apparatus as described in clause 181, or any other clause, wherein said latching switch comprises a magnetically triggered latching switch.
184. A vaginal temperature sensor apparatus as described in clause 181, or any other clause, wherein said latching switch comprises a "push"-to-make latching switch.
185. A vaginal temperature sensor apparatus as described in clause 140, or any other clause, wherein said substantially error-free, user-initiated device activation componentry is further configured to be re-enabled at some point after it is reset, upon occurrence of a re-enabling event.
186. A vaginal temperature sensor apparatus as described in clause 185, or any other clause, wherein said re-enabling event comprises device immobility.
187. A vaginal temperature sensor apparatus as described in clause 185, or any other clause, wherein said re-enabling event comprises duration within a temperature range.
188. A vaginal temperature sensor apparatus as described in clause 185, or any other clause, wherein said re-enabling event comprises unbending of said device.
189. A vaginal temperature sensor apparatus as described in clause 140, or any other clause, and further comprising a sensor configured to re-enable said substantially error-free, user-initiated device activation componentry upon occurrence of a re-enabling event.
190. A vaginal temperature sensor apparatus as described in clause 189, or any other clause, wherein said sensor comprises a sensor selected from the group consisting of: magnetic field sensor, capacitive sensor, induction sensor, photoelectric sensor, moisture sensor, device flexure sensor, thermal sensor, pressure sensor, and optical sensor.
191. A vaginal temperature sensor apparatus as described in clause 140, or any other clause, wherein said substantially error-free, user-initiated device activation componentry is configured to start use of said battery power upon occurrence of a primary event and a secondary event.
192. A vaginal temperature sensor apparatus as described in clause 191, or any other clause, wherein said primary event comprises an event selected from the group consisting of: device removal from packaging, moisture, device bending, pressure, switch pressure, device placement into a cradle, and temperature.
193. A vaginal temperature sensor apparatus as described in clause 191, or any other clause, wherein said secondary event is different from said primary event.
194. A vaginal temperature sensor apparatus as described in clause 140, or any other clause, and further comprising componentry configured to trigger a shift from a lower power mode to a full activation mode where temperatures can actually be sensed.
195. A vaginal temperature sensor apparatus as described in clause 140, or any other clause, and further comprising a visually sense-able, battery power-on indicator connected with said battery.
196. A vaginal temperature sensor apparatus as described in clause 137, or any other clause, wherein said visually sense-able, battery power-on indicator comprises a LED.
197. A vaginal temperature sensor apparatus as described in clause 138, or any other clause, wherein said LED comprises a short duration LED.
198. A vaginal temperature sensing method comprising the steps of:

establishing a battery, vaginal temperature sensor componentry, and sensed vaginal temperature transmission componentry as part of temperature sensing electrical componentry;
establishing flexible, non-conductive material proximate said temperature sensing electrical componentry; and
configuring substantially error-free, user-initiated device activation componentry to start use of said battery power upon occurrence of an event.
199. A vaginal temperature sensing method as described in clause 198, or any other clause, wherein said step of establishing flexible, non-conductive material proximate said temperature sensing electrical componentry comprises the step of generating a closed curvilinear shape.
200. A vaginal temperature sensing method as described in clause 199, or any other clause, wherein said closed curvilinear shape comprises a ring shape.
201. A vaginal temperature sensing method as described in clause 200, or any other clause, wherein said step of establishing flexible, non-conductive material proximate said temperature sensing electrical componentry comprises the step of forming at least part of a vaginal temperature sensing ring.
202. A vaginal temperature sensing method as described in clause 198, or any other clause, wherein said step of configuring substantially error-free, user-initiated device activation componentry comprises the step of configuring said substantially error-free, user-initiated device activation componentry so that, upon said occurrence of an event, power from said battery is drawn under a lower power mode.
203. A vaginal temperature sensing method as described in clause 202, or any other clause, wherein said lower power mode is observed after an initialization power mode.
204. A vaginal temperature sensing method as described in clause 202, or any other clause, wherein said lower power mode is a sleep mode power mode.
205. A vaginal temperature sensing method as described in clause 198, or any other clause, and further comprising the step of configuring said componentry to trigger a shift from a lower power mode to a full activation mode where temperatures can actually be sensed.
206. A vaginal temperature sensing method as described in clause 198, or any other clause, wherein said step of configuring substantially error-free, user-initiated device activation componentry comprises the step of configuring said substantially error-free, user-initiated device activation componentry so that said occurrence of an event initiates enablement of a full activation power mode during which vaginal temperature can be sensed.
207. A vaginal temperature sensing method as described in clause 206, or any other clause, wherein said occurrence of an event also initiates enablement of data transmission.
208. A vaginal temperature sensing method as described in clause 207, or any other clause, wherein said data transmission is achieved via BlueTooth™.
209. A vaginal temperature sensing method as described in clause 198, or any other clause, wherein said event comprises an event selected so as to substantially eliminate possibility of premature activation of said substantially error-free, user-initiated device activation componentry.
210. A vaginal temperature sensing method as described in clause 209, or any other clause, wherein said event comprises a human-initiated event.

211. A vaginal temperature sensing method as described in clause 210, or any other clause, wherein said event comprises a user-initiated event.
212. A vaginal temperature sensing method as described in clause 209, or any other clause, wherein said event is selected so that said substantially error-free, user-initiated device activation componentry does not initiate power consumption during pre-sale device transportation or storage.
213. A vaginal temperature sensing method as described in clause 209, or any other clause, wherein said substantially error-free, user-initiated device activation componentry comprises a thermocouple.
214. A vaginal temperature sensing method as described in clause 209, or any other clause, wherein said substantially error-free, user-initiated device activation componentry further comprises a temperature duration sensor.
215. A vaginal temperature sensing method as described in clause 209, or any other clause, wherein said event comprises a user-caused mechanical action.
216. A vaginal temperature sensing method as described in clause 215, or any other clause, wherein said event comprises sufficient device bending.
217. A vaginal temperature sensing method as described in clause 215, or any other clause, wherein said event comprises sufficient device pressurization.
218. A vaginal temperature sensing method as described in clause 217, or any other clause, wherein said event comprises switch pressurization.
219. A vaginal temperature sensing method as described in clause 215, or any other clause, wherein said event comprises device removal from packaging.
220. A vaginal temperature sensing method as described in clause 215, or any other clause, wherein said event comprises device placement into a cradle.
221. A vaginal temperature sensing method as described in clause 220, or any other clause, wherein said cradle is a part of device packaging.
222. A vaginal temperature sensing method as described in clause 215, or any other clause, wherein said event comprises package manipulation.
223. A vaginal temperature sensing method as described in clause 215, or any other clause, wherein said event comprises proximity condition change.
224. A vaginal temperature sensing method as described in clause 198, or any other clause, and further comprising the step of configuring said substantially error-free, user-initiated device activation componentry to initiate consumption of said battery power until upon occurrence of a primary event and a secondary event.
225. A vaginal temperature sensing method as described in clause 22, or any other clause,4 wherein said primary event comprises an event selected from the group consisting of: device removal from packaging, moisture, device bending, pressure, switch pressure, device placement into a cradle, light incident on at least a portion of said apparatus, and temperature.
226. A vaginal temperature sensing method as described in clause 224, or any other clause, wherein said secondary event is different from said primary event.
227. A vaginal temperature sensing method as described in clause 198, or any other clause, and further comprising the step of further configuring said substantially error-free, user-initiated device activation componentry to be re-start power consumption after it is reset, upon occurrence of a re-enabling event.
228. A vaginal temperature sensing method as described in clause 227, or any other clause, wherein said re-enabling event comprises device immobility.
229. A vaginal temperature sensing method as described in clause 227, or any other clause, wherein said re-enabling event comprises duration within a temperature range.
230. A vaginal temperature sensing method as described in clause 227, or any other clause, and further comprising the step of sensing a re-enabling event with a sensor.
231. A vaginal temperature sensing method as described in clause 230, or any other clause, wherein said sensor comprises a sensor selected from the group consisting of: material proximity sensor, magnet sensor, magnetic field sensor, capacitive sensor, induction sensor, photoelectric sensor, moisture sensor, device flexure sensor, thermal sensor, pressure sensor, and optical sensor.
232. A vaginal temperature sensing method as described in clause 198, or any other clause, wherein said step of configuring substantially error-free, user-initiated device activation componentry to initiate use of said battery power upon occurrence of an event comprises configuring said substantially error-free, user-initiated device activation componentry to comprise a switch that is open before said occurrence of an event.
233. A vaginal temperature sensing method as described in clause 232, or any other clause, wherein said switch comprises a proximity switch.
234. A vaginal temperature sensing method as described in clause 232, or any other clause, wherein said proximity switch comprises a magnetic reed switch and magnetic attraction keeps said switch open until said occurrence of said event.
235. A vaginal temperature sensing method as described in clause 234, or any other clause, wherein said substantially error-free, user-initiated device activation componentry comprises a permanent magnet.
236. A vaginal temperature sensing method as described in clause 232, or any other clause, wherein said switch comprises a latching switch.
237. A vaginal temperature sensing method as described in clause 198, or any other clause, wherein said step of configuring substantially error-free, user-initiated device activation componentry to initiate use of said battery power comprises the step of configuring said substantially error-free, user-initiated device activation componentry to comprise a latching switch.
238. A vaginal temperature sensing method as described in clause 237, or any other clause, wherein said latching switch is closed upon said occurrence of said event.
239. A vaginal temperature sensing method as described in clause 237, or any other clause, wherein said latching switch comprises a magnetically triggered latching switch.
240. A vaginal temperature sensing method as described in clause 237, or any other clause, wherein said latching switch comprises a "push"-to-make latching switch.
241. A vaginal temperature sensing method as described in clause 198, or any other clause, and further comprising the step of establishing a visually sense-able, battery power-on indicator that is connected with said battery.
242. A vaginal temperature sensing method as described in clause 241, or any other clause, wherein said visually sense-able, battery power-on indicator comprises a LED.
243. A vaginal temperature sensing method as described in clause 242, or any other clause, wherein said LED comprises a short duration LED.

244. A vaginal temperature sensing method as described in clause 198, or any other clause, and further comprising the step of establishing an antenna as part of said temperature sensing electrical componentry.
245. A vaginal temperature sensing method as described in clause 244, or any other clause, wherein said antenna is established along only a less than 30% portion of a device centerline.
246. A vaginal temperature sensing method as described in clause 245, or any other clause, wherein said device centerline is a ring centerline.
247. A vaginal temperature sensing method as described in clause 244, or any other clause, wherein said antenna is established along substantially all of a device centerline.
248. A vaginal temperature sensing method as described in clause 247, or any other clause, wherein said device centerline is a ring centerline.
249. A vaginal temperature sensing method as described in clause 244, or any other clause, wherein said temperature sensing electrical componentry is flexible.
250. A system or apparatus substantially as herein described with reference to any one or more of the figures and description.
251. An apparatus that includes any componentry or feature(s) disclosed in either the written description or figures, combined in any manner or permutation.
252. The method according to any of the method clauses and further comprising any of the steps as shown in any of the figures, separately, in any combination or permutation.
253. A process for analyzing transformed body temperature indications of a user to notify of an ovulation event comprising the steps of:
    periodically sensing actual internal body temperature values throughout at least a high temperature timeframe for said user;
    storing a bracket of said actual internal body temperature values that include at least said high temperature timeframe for said user;
    automatically computer transforming said bracket of actual internal body temperature values to recalculate a daily zenith value;
    automatically generating a transformed estimated effective daily zenith created value;
    storing said transformed estimated effective daily zenith created value;
    automatically computer analyzing a succession of adjacent transformed estimated effective daily zenith created values to determine a dip in said transformed estimated effective daily zenith created values;
    automatically computer generating a transformed ovulation prediction output based on said step of automatically computer analyzing a succession of adjacent transformed estimated effective daily zenith created values to determine a dip in said transformed estimated effective daily zenith created values; and
    providing an ovulation indication as a result of step of automatically computer generating a transformed ovulation prediction output.
254. A process for analyzing transformed body temperature indications of a user to notify of an ovulation event as described in clause 253, or any other clause, wherein said step of automatically computer transforming said bracket of actual internal body temperature values to recalculate a daily zenith value comprises the step of automatically computer transforming a bracket of diurnal internal body temperature values.
255. A process for analyzing transformed body temperature indications of a user to notify of an ovulation event as described in clause 253, or any other clause, wherein said step of automatically computer transforming said bracket of actual internal body temperature values to recalculate a daily zenith value comprises the step of automatically computer transforming a bracket of awake period internal body temperature values.
256. A process for analyzing transformed body temperature indications of a user to notify of an ovulation event as described in clause 253, or any other clause, wherein said step of automatically computer transforming said bracket of actual internal body temperature values to recalculate a daily zenith value comprises the step of automatically computer smoothing a bracket of internal body temperature values.
257. A process for analyzing transformed body temperature indications of a user to notify of an ovulation event as described in clause 256, or any other clause, wherein said step of automatically computer smoothing a bracket of internal body temperature values comprises the step of automatically computer averaging a bracket of internal body temperature values
258. A process for analyzing transformed body temperature indications of a user to notify of an ovulation event as described in clause 256, or any other clause, wherein said step of automatically computer smoothing a bracket of internal body temperature values comprises the step of automatically computer utilizing only threshold selected internal body temperature values.
259. A process for analyzing transformed body temperature indications of a user to notify of an ovulation event as described in clause 258, or any other clause, wherein said step of automatically computer utilizing only threshold selected internal body temperature values comprises the step of automatically computer utilizing only windowed intermediate internal body temperature values.
260. A process for analyzing transformed body temperature indications of a user to notify of an ovulation event as described in clause 256, or any other clause, wherein said step of automatically computer smoothing a bracket of internal body temperature values comprises the steps of: automatically computer generating a frequency spectrum for said internal body temperature values; and automatically computer eliminating higher frequency compositions from said frequency spectrum for said internal body temperature values.
261. A process for analyzing transformed body temperature indications of a user to notify of an ovulation event as described in clause 256, or any other clause, wherein said step of automatically computer smoothing a bracket of internal body temperature values comprises the steps of: automatically computer generating a frequency spectrum for said internal body temperature values; and automatically computer isolating relevant frequency compositions from said frequency spectrum for said internal body temperature values.
262. A process for analyzing transformed body temperature indications of a user to notify of an ovulation event as described in clause 260, or any other clause, wherein said step of automatically computer eliminating higher frequency compositions from said frequency spectrum for said internal body temperature values comprises automatically computer eliminating frequency compositions from said frequency spectrum for said internal body temperature values that have a frequency greater than those selected from a group consisting of: one-half cycle/ every thirty minutes frequency, one-half cycle/every hour frequency, one-half cycle/every two hours frequency, and one-half cycle/every three hours frequency.

263. A process for analyzing transformed body temperature indications of a user to notify of an ovulation event as described in clause 261, or any other clause, wherein said step of automatically computer isolating relevant frequency compositions from said frequency spectrum for said internal body temperature values comprises automatically computer isolating frequency compositions from said frequency spectrum for said internal body temperature values that have a frequency lower than those selected from a group consisting of: one-half cycle/every thirty minutes frequency, one-half cycle/every hour frequency, one-half cycle/every two hours frequency, and one-half cycle/every three hours frequency.

264. A process for analyzing transformed body temperature indications of a user to notify of an ovulation event as described in clause 253, or any other clause, wherein said step of automatically computer transforming said bracket of actual internal body temperature values to recalculate a daily zenith value comprises the step of automatically computer transforming a bracket of internal body temperature values to create average values over a plurality of actual internal body temperature values.

265. A process for analyzing transformed body temperature indications of a user to notify of an ovulation event as described in clause 264, or any other clause, wherein said step of automatically computer transforming a bracket of internal body temperature values to create average values over a plurality of actual internal body temperature values comprises the step of automatically computer transforming a bracket of internal body temperature values to create a running average value over a plurality of actual internal body temperature values.

266. A process for analyzing transformed body temperature indications of a user to notify of an ovulation event as described in clause 264, or any other clause, wherein said step of automatically computer transforming a bracket of internal body temperature values to create average values over a plurality of actual internal body temperature values comprises the step of automatically computer transforming a bracket of internal body temperature values to create a variable time window running average value over a plurality of actual internal body temperature values.

267. A process for analyzing transformed body temperature indications of a user to notify of an ovulation event as described in clause 265, or any other clause, wherein said step of automatically computer transforming a bracket of internal body temperature values to create average values over a plurality of actual internal body temperature values comprises the step of automatically computer transforming a bracket of internal body temperature values to create an eight hour running average value of actual internal body temperature values.

268. A process for analyzing transformed body temperature indications of a user to notify of an ovulation event as described in clause 266, or any other clause, wherein said step of automatically computer transforming a bracket of internal body temperature values to create a variable time window running average value over a plurality of actual internal body temperature values comprises the step of automatically computer transforming a bracket of internal body temperature values to create a statistically optimized running average value of actual internal body temperature values.

269. A process for analyzing transformed body temperature indications of a user to notify of an ovulation event as described in clause 266, or any other clause, wherein said step of automatically computer transforming a bracket of internal body temperature values to create average values over a plurality of actual internal body temperature values further comprises the steps of:
automatically computer generating a plurality of running average values; and
automatically computer selecting an optimal running average of internal body temperature values from said plurality of running average values.

270. A process for analyzing transformed body temperature indications of a user to notify of an ovulation event as described in clause 253, or any other clause, wherein said step of automatically computer transforming said bracket of actual internal body temperature values to recalculate a daily zenith value comprises the step of automatically computer transforming said bracket of internal body temperature values to endeavor to remove non-ovulation related temperature fluctuations from said actual internal body temperature values.

271. A process for analyzing transformed body temperature indications of a user to notify of an ovulation event as described in clause 270, or any other clause, wherein said step of automatically computer transforming a said bracket of internal body temperature values to endeavor to remove non-ovulation related temperature fluctuations from said actual internal body temperature values comprises the step of automatically computer transforming a bracket of internal body temperature values to endeavor to remove non-ovulation related temperature fluctuations from said actual internal body temperature values selected from a group consisting of: endeavoring to remove activity related temperature fluctuations from said actual internal body temperature values; endeavoring to remove environmental related temperature fluctuations from said actual internal body temperature values; endeavoring to remove short duration temperature fluctuations from said actual internal body temperature values; and endeavoring to remove higher frequency temperature fluctuation compositions from said actual internal body temperature values.

272. A process for analyzing transformed body temperature indications of a user to notify of an ovulation event as described in clause 253, or any other clause, wherein said step of automatically computer analyzing a succession of adjacent transformed estimated effective daily zenith created values to determine a dip in said transformed estimated effective daily zenith created values comprises the steps of: automatically computer analyzing a first data interval value; automatically computer analyzing a second data interval decrease value; and automatically computer analyzing a third data interval increase value.

273. A process for analyzing transformed body temperature indications of a user to notify of an ovulation event as described in clause 272, or any other clause, wherein said step of automatically computer analyzing a third data interval increase value comprises the step of automatically computer analyzing a full bracket of internal body temperature values.

274. A process for analyzing transformed body temperature indications of a user to notify of an ovulation event as described in clause 253, or any other clause, wherein said step of automatically computer analyzing a succession of adjacent transformed estimated effective daily zenith created values to determine a dip in said transformed estimated effective daily zenith created values further comprises the step of factoring in a likely time window since a last ovulation event for said user.

275. A computerized ovulation analysis system to improve results from obtained and transformed user data and indicate an onset of an ovulation event comprising:
a periodic capture internal body temperature sensor for placement in contact with a woman's body;
an internal body temperature data memory responsive to said periodic capture internal body temperature sensor, wherein said internal body temperature data memory is configured to store a bracket of actual internal body temperature values that include at least a high temperature timeframe for said user;
a computer processor operated automatic data transform recalculator that is coupled to said internal body temperature data memory, and that is configured to act on said bracket of actual internal body temperature values and recalculate a daily zenith value;
an automatic transformed estimated effective daily zenith created value generator responsive to said computer processor operated automatic data transform recalculator, wherein said automatic transformed estimated effective daily zenith created value generator is configured to automatically transform said bracket of actual internal body temperature values to generate transformed estimated effective daily zenith created value;
a transformed estimated effective daily zenith created value memory into which said transformed estimated effective daily zenith created value is at least temporarily stored;
an adjacent transformed estimated effective daily zenith created value dip data processor configured to automatically analyze said a succession of adjacent transformed estimated effective daily zenith created values and determine a dip in said transformed estimated effective daily zenith created values;
a transformed daily zenith ovulation prediction output generator responsive to said adjacent transformed estimated effective daily zenith created value dip data processor; and
a zenith-based ovulation indicator responsive to said transformed daily zenith ovulation prediction output generator.

276. A computerized ovulation analysis system as described in clause 275, or any other clause, wherein said computer processor operated automatic data transform recalculator comprises an automatic computer internal body temperature value transformer configured to act on a bracket of diurnal internal body temperature values.

277. A computerized ovulation analysis system as described in clause 275, or any other clause, wherein said computer processor operated automatic data transform recalculator comprises an automatic computer internal body temperature value transformer configured to act on a bracket of awake period internal body temperature values.

278. A computerized ovulation analysis system as described in clause 275, or any other clause, wherein said computer processor operated automatic data transform recalculator comprises an automatic computer internal body temperature value smoother configured to act on a bracket of internal body temperature values.

279. A computerized ovulation analysis system as described in clause 278, or any other clause, wherein said automatic computer internal body temperature value smoother comprises an automatic computer internal body temperature value averager configured to act on a bracket of internal body temperature values.

280. A computerized ovulation analysis system as described in clause 278, or any other clause, wherein said automatic computer internal body temperature value smoother comprises an automatic computer internal body temperature value threshold selector configured to utilize only threshold selected internal body temperature values.

281. A computerized ovulation analysis system as described in clause 280, or any other clause, wherein said automatic computer internal body temperature value threshold selector comprises an automatic computer internal body temperature value threshold selector configured to utilize only windowed intermediate internal body temperature values.

282. A computerized ovulation analysis system as described in clause 278, or any other clause, wherein said automatic computer internal body temperature value smoother comprises:
an automatic computer internal body temperature value frequency spectrum generator; and
an automatic computer internal body temperature value higher frequency eliminator.

283. A computerized ovulation analysis system as described in clause 278 wherein said automatic computer internal body temperature value smoother comprises:
an automatic computer internal body temperature value frequency spectrum generator; and
an automatic computer internal body temperature value relevant frequency isolator.

284. A computerized ovulation analysis system as described in clause 282, or any other clause, wherein said automatic computer internal body temperature value higher frequency eliminator comprises an automatic computer internal body temperature value relevant higher frequency eliminator selected from a group consisting of:
a greater than one-half cycle per every thirty minutes automatic computer internal body temperature value higher frequency eliminator;
a less than one-half cycle per hour automatic computer internal body temperature value higher frequency eliminator;
a less than one-half cycle per every two hours automatic computer internal body temperature value higher frequency eliminator; and
a less than one-half cycle per every three hours automatic computer internal body temperature value higher frequency eliminator.

285. A computerized ovulation analysis system as described in clause 283, or any other clause, wherein said automatic computer internal body temperature value relevant frequency isolator comprises an automatic computer internal body temperature value frequency isolator selected from a group consisting of:
a less than one-half cycle per every thirty minutes automatic computer internal body temperature value frequency isolator;
a less than one-half cycle per hour automatic computer internal body temperature value frequency isolator;
a less than one-half cycle per every two hours automatic computer internal body temperature value frequency isolator; and
a less than one-half cycle per every three hours automatic computer internal body temperature value frequency isolator.

286. A computerized ovulation analysis system as described in clause 275, or any other clause, wherein said computer processor operated automatic data transform recalculator comprises an automatic computer internal body temperature value averager configured to act on a plurality of actual internal body temperature values.

287. A computerized ovulation analysis system as described in clause 286, or any other clause, wherein said automatic computer internal body temperature value averager comprises an automatic computer internal body temperature value running value averager.

288. A computerized ovulation analysis system as described in clause 286, or any other clause, wherein said automatic computer internal body temperature value averager comprises an automatic computer internal body temperature value variable time window running value averager.

289. A computerized ovulation analysis system as described in clause 287, or any other clause, wherein said automatic computer internal body temperature value running value averager comprises an automatic computer internal body temperature value eight hour running value averager.

290. A computerized ovulation analysis system as described in clause 288, or any other clause, wherein said automatic computer internal body temperature value variable time window running value average comprises an automatic computer internal body temperature value statistically optimized time window running value averager.

291. A computerized ovulation analysis system as described in clause 288, or any other clause, wherein said automatic computer internal body temperature value averager comprises:
an automatic computer internal body temperature value multiple running value average generator; and
an automatic computer optimal running value average selector responsive to said automatic computer internal body temperature value multiple running value average generator.

292. A computerized ovulation analysis system as described in clause 275, or any other clause, wherein said computer processor operated automatic data transform recalculator comprises an automatic computer estimated non-ovulation related temperature data fluctuation remover.

293. A computerized ovulation analysis system as described in clause 292, or any other clause, wherein said automatic computer estimated non-ovulation related temperature data fluctuation remover comprises an automatic computer estimated non-ovulation related temperature data fluctuation remover selected from a group consisting of:
an automatic computer environmental related temperature data fluctuation remover;
an automatic computer short duration temperature data fluctuation remover; and
an automatic computer higher frequency temperature data fluctuation remover.

294. A computerized ovulation analysis system as described in clause 275, or any other clause, wherein said adjacent transformed estimated effective daily zenith created value dip data processor comprises:
a first data interval value analyzer;
a second data interval decrease value analyzer; and
a third data interval increase value analyzer.

295. A computerized ovulation analysis system as described in clause 294, or any other clause, wherein said third data interval increase value analyzer comprises a full bracket of internal body temperature value analyzer.

296. A computerized ovulation analysis system as described in clause 275, or any other clause, wherein said adjacent transformed estimated effective daily zenith created value dip data processor further comprises a likely time window since last ovulation event analyzer.

297. A process for improved notification of an ovulation event for a user comprising the steps of:
periodically sensing internal body temperature values for said user;
automatically transforming said internal body temperature values to a first transformation computation generated ovulation prediction output;
automatically transforming said internal body temperature values to a second transformation computation generated ovulation prediction output;
automatically comparing said first transformation computation generated ovulation prediction output with said second transformation computation generated ovulation prediction output;
automatically determining whether said first transformation computation generated ovulation prediction output or said second transformation computation generated ovulation prediction output is likely to provide a more user-preference aligned indication of the likely existence of an ovulation event;
automatically utilizing whichever ovulation prediction output provides a more user-preference aligned indication of a likely existence of an ovulation event; and
providing an ovulation indication based on said step of automatically utilizing whichever ovulation prediction output provides a more user-preference aligned indication of a likely existence of an ovulation event.

298. A process for improved notification of an ovulation event for a user as described in clause 297, or any other clause, wherein said step of automatically determining whether said first transformation computation ovulation prediction output or said second transformation computation ovulation prediction output is likely to provide a more user-preference aligned indication of the likely existence of an ovulation event comprises the step of automatically utilizing whichever computation ovulation prediction output provides the earliest indication of a likely existence of an ovulation event based upon said step of determining the likely existence of an ovulation event.

299. A process for improved notification of an ovulation event for a user as described in clause 297, or any other clause, wherein said step of automatically determining whether said first transformation computation ovulation prediction output or said second transformation computation ovulation prediction output is likely to provide a more user-preference aligned indication of the likely existence of an ovulation event comprises the step of automatically utilizing whichever computation ovulation prediction output provides the least false positive indications of a likely existence of an ovulation event based upon said step of determining the likely existence of an ovulation event.

300. A process for improved notification of an ovulation event for a user as described in clause 297, or any other clause, wherein said step of automatically determining whether said first transformation computation ovulation prediction output or said second transformation computation ovulation prediction output is likely to provide a more user-preference aligned indication of the likely existence of an ovulation event comprises the step of automatically utilizing whichever computation ovulation prediction output provides the least missed indications of a likely existence of an ovulation event based upon said step of determining the likely existence of an ovulation event.

301. A process for improved notification of an ovulation event for a user as described in clause 297, or any other clause, and further comprising the step of providing a user-preference input to which said step of automatically determining whether said first transformation computation generated ovulation prediction output or said second transformation computation generated ovulation prediction output is likely to provide a more user-preference aligned indication of the likely existence of an ovulation event is responsive.

302. A computerized improved reliability ovulation notification system comprising:
   a periodic capture internal body temperature sensor for placement in contact with a woman's body;
   a computer data input from said periodic capture internal body temperature sensor;
   a computer processor operated first automatic data transform recalculator responsive to said computer data input from said periodic capture internal body temperature sensor;
   a computer processor operated second automatic data transform recalculator responsive to said computer data input from said periodic capture internal body temperature sensor;
   an automatic user-preference ovulation transformation comparator responsive to said first automatic data transform recalculator and said second automatic data transform recalculator, and configured to automatically determine whether said first automatic data transform recalculator or said second automatic data transform recalculator is likely to provide a more user-preference aligned indication of the likely existence of an ovulation event; and
   an ovulation prediction output responsive to said automatic user-preference ovulation transformation comparator.

303. A computerized improved reliability ovulation notification system as described in clause 302, or any other clause, wherein said automatic user-preference ovulation transformation comparator comprises an earliest transformation indication ovulation transformation comparator.

304. A computerized improved reliability ovulation notification system as described in clause 302, or any other clause, wherein said automatic user-preference ovulation transformation comparator comprises a least false positive ovulation transformation comparator.

305. A computerized improved reliability ovulation notification system as described in clause 302, or any other clause, wherein said automatic user-preference ovulation transformation comparator comprises a least false positive ovulation transformation comparator.

306. A computerized improved reliability ovulation notification system as described in clause 302, or any other clause, and further comprising a user-preference input to which said automatic user-preference ovulation transformation comparator is responsive.

307. A process for improved reliability notification of an ovulation event for a user comprising the steps of:
   periodically sensing internal body temperature values for said user;
   automatically accepting a data input to a computer based at least in part on said step of periodically sensing internal body temperature values;
   establishing in a computer at least one automated ovulation computational transformation program with starting ovulation transformation parameters;
   automatically applying said automated ovulation computational transformation program with said starting ovulation transformation parameters, to at least some of said internal body temperature values to automatically create a starting ovulation data transform;
   generating a transformed ovulation prediction output based on said starting ovulation data transform;
   automatically varying said starting ovulation transformation parameters for said automated ovulation computational transformation program to establish a varied automated ovulation computational transformation;
   automatically applying said varied automated ovulation computational transformation program with said automatically varying said ovulation transformation parameters, to at least some of said internal body temperature values to automatically create a varied ovulation data transform;
   generating a varied transform ovulation prediction output based on said varied ovulation data transform;
   automatically comparing said starting transformed ovulation prediction output with said varied transform ovulation prediction output;
   automatically determining whether said starting transformed ovulation prediction output or said varied transform ovulation prediction output is likely to provide a more user-preference aligned indication of the likely existence of an ovulation event;
   providing an ovulation indication based on said step of automatically determining whether said starting transformed ovulation prediction output or said varied transform ovulation prediction output is likely to provide a more user-preference aligned indication of the likely existence of an ovulation event; and
   storing ovulation transformation parameters that are determined to provide a more user-preference aligned indication of the likely existence of an ovulation event for future use.

308. A process for improved reliability notification of an ovulation event for a user as described in clause 307, or any other clause, and further comprising the step of re-establishing starting ovulation transformation parameters in response to said step of automatically determining whether said starting transformed ovulation prediction output or said varied transform ovulation prediction output is likely to provide a more user-preference aligned indication of the likely existence of an ovulation event.

309. A process for improved reliability notification of an ovulation event for a user as described in clause 308, or any other clause, wherein said step of re-establishing starting ovulation transformation parameters comprises the step of cumulatively re-establishing starting ovulation transformation parameters.

310. A process for improved reliability notification of an ovulation event for a user as described in clause 307, or any other clause, wherein said step of automatically varying said ovulation transformation parameters for said automated ovulation computational transformation program to establish a varied automated ovulation computational transformation program comprises the step of automatically varying previously varied ovulation transformation parameters for said automated ovulation computational transformation program to establish a varied automated ovulation computational transformation program.

311. A process for improved reliability notification of an ovulation event for a user as described in clause 307, or any other clause, wherein said step of automatically varying said ovulation transformation parameters for said automated ovulation computational transformation program to establish a varied automated ovulation computational transformation program comprises the step of automatically cumulatively varying previously applied ovulation transformation parameters for said automated ovulation computational transformation program to establish a varied automated ovulation computational transformation program.

312. A process for improved reliability notification of an ovulation event for a user as described in clause 307, or any other clause, and further comprising the step of providing a user-preference input to which said step of automatically determining whether said transformed ovulation prediction output or said varied transform ovulation prediction output is likely to provide a more user-preference aligned indication of the likely existence of an ovulation event is responsive.

313. A process for improved reliability notification of an ovulation event for a user as described in clause 307, or any other clause, and further comprising the step of establishing a plurality of automated ovulation computational transformation programs each having ovulation transformation parameters applied to that automated ovulation computational transformation program.

314. A process for improved reliability notification of an ovulation event for a user as described in clause 313, or any other clause, and further comprising the step of combining the results of each of said plurality of automated ovulation computational transformation programs in an ovulation prediction output.

315. A process for improved reliability notification of an ovulation event for a user as described in clause 313, or any other clause, and further comprising the step of including the results of at least two of said plurality of automated ovulation computational transformation programs in an ovulation prediction output.

316. A process for improved reliability notification of an ovulation event for a user as described in clause 307 wherein said step of automatically varying said ovulation transformation parameters for said automated ovulation computational transformation program to establish a varied automated ovulation computational transformation program comprises the step of automatically varying a range size ovulation transformation parameter for said automated ovulation computational transformation program to establish a varied automated ovulation computational transformation program.

317. A process for improved reliability notification of an ovulation event for a user as described in clause 307, or any other clause, wherein said step of automatically varying said ovulation transformation parameters for said automated ovulation computational transformation program to establish a varied automated ovulation computational transformation program comprises the step of automatically varying a range drift ovulation transformation parameter for said automated ovulation computational transformation program to establish a varied automated ovulation computational transformation program.

318. A process for improved reliability notification of an ovulation event for a user as described in clause 307, or any other clause, wherein said step of automatically varying said ovulation transformation parameters for said automated ovulation computational transformation program to establish a varied automated ovulation computational transformation program comprises the step of automatically varying a threshold inclusion ovulation transformation parameter for said automated ovulation computational transformation program to establish a varied automated ovulation computational transformation program.

319. A process for improved reliability notification of an ovulation event for a user as described in clause 307, or any other clause, wherein said step of automatically varying said ovulation transformation parameters for said automated ovulation computational transformation program to establish a varied automated ovulation computational transformation program comprises the step of automatically varying an ovulation transformation coefficient parameter for said automated ovulation computational transformation program to establish a varied automated ovulation computational transformation program.

320. A process for improved reliability notification of an ovulation event for a user as described in clause 307, or any other clause, wherein said step of automatically varying said ovulation transformation parameters for said automated ovulation computational transformation program to establish a varied automated ovulation computational transformation program comprises the step of automatically varying an ovulation transformation weight parameter for said automated ovulation computational transformation program to establish a varied automated ovulation computational transformation program.

321. A process for improved reliability notification of an ovulation event for a user as described in clause 320 wherein said step of automatically varying said starting ovulation transformation parameters for said automated ovulation computational transformation program to establish a varied automated ovulation computational transformation comprises the step of automatically varying a plurality of ovulation transformation weight parameters to which said plurality of automated ovulation computational transformation programs are responsive.

322. A process for improved reliability notification of an ovulation event for a user as described in clause 307 and further comprising the step of accepting an independent user condition input to a computer, and wherein said step of automatically determining whether said transformed ovulation prediction output or said varied transform ovulation prediction output is likely to provide a more user-preference aligned indication of the likely existence of an ovulation event comprises the step of automatically utilizing said independent user condition input in determining which of said transformed ovulation prediction outputs is likely to provide a more user-preference aligned indication.

323. A process for improved reliability notification of an ovulation event for a user as described in clause 322 wherein said step of automatically accepting an independent user condition input to a computer comprises a step selected from a group consisting of: automatically accepting a prior period input to a computer; automatically accepting a luteinizing hormone test input to a computer; automatically accepting a fertility test result input to a computer; automatically accepting a user data input to a computer; automatically accepting a user menstrual cycle input to a computer; automatically accepting user body type input to a computer; automatically accepting user physical condition input to a computer; automatically accepting user medical history input to a computer; automatically accepting user text message input to a computer; and automatically accepting plurality of many user inputs to a computer.

324. A process for improved reliability notification of an ovulation event for a user as described in clause 307, or any other clause, wherein said step of automatically accepting at least one series of inputs to a computer based at least in part on said step of periodically sensing internal body temperature values further comprises the step of automatically accepting a many user composite input to a computer.

325. A process for improved reliability notification of an ovulation event for a user as described in clause 324, or any other clause, wherein said step of automatically accepting a many user composite input to a computer comprises the step of automatically accepting a demographically grouped many user composite input to a computer.

326. A process for improved reliability notification of an ovulation event for a user as described in clause 325, or any other clause, wherein said step of automatically accepting a demographically grouped many user composite input to a computer comprises the step of automatically accepting a demographically grouped many user composite input to a computer selected from a group consisting of: automatically accepting an age grouped many user composite input to a computer; automatically accepting an ethnically grouped many user composite input to a computer; automatically accepting a prior pregnancy grouped many user composite input to a computer; automatically accepting a medication-taken grouped many user composite input to a computer; automatically accepting a physical activity grouped many user composite input to a computer; automatically accepting a physical condition grouped many user composite input to a computer; automatically accepting a pre-existing medical condition grouped many user composite input to a computer.

327. A process for improved reliability notification of an ovulation event for a user as described in clause 324, or any other clause, wherein said step of automatically comparing said transformed ovulation prediction output with said varied transform ovulation prediction output comprises the step of automatically comparing said transformed ovulation prediction output with said varied transform ovulation prediction output to a many user composite database, and wherein said step of automatically determining whether said transformed ovulation prediction output or said varied transform ovulation prediction output is likely to provide a more user-preference aligned indication of the likely existence of an ovulation event comprises the step of automatically determining whether said transformed ovulation prediction output or said varied transform ovulation prediction output is likely to provide a more user-preference aligned indication of the likely existence of an ovulation event from application of said many user composite database.

328. A process for improved reliability notification of an ovulation event for a user as described in clause 327, or any other clause, wherein said step of automatically determining whether said transformed ovulation prediction output or said varied transform ovulation prediction output is likely to provide a more user-preference aligned indication of the likely existence of an ovulation event from application of said many user composite database comprises the step of automatically determining a minimum error value from application of said many user composite database 329. A process for improved reliability notification of an ovulation event for a user as described in clause 328, or any other clause, wherein said step of automatically determining a minimum error value from application of said many user composite database comprises the step of automatically determining a minimum least squares error value from application of said many user composite database.

330. A process for improved reliability notification of an ovulation event for a user as described in clause 307, or any other clause, wherein said step of automatically applying said automated ovulation computational transformation program with said ovulation transformation parameters, to said at least one series of inputs to automatically create an ovulation data transform comprises the step of automatically creating a transformed estimated effective daily zenith created value.

331. A process for improved reliability notification of an ovulation event for a user as described in clause 330, or any other clause, wherein said step of automatically creating a transformed estimated effective daily zenith created value comprises the step of automatically computer transforming a bracket of internal body temperature values to create a running average value over a plurality of actual internal body temperature values.

332. A process for improved reliability notification of an ovulation event for a user as described in clause 330, or any other clause, wherein said step of generating a transformed ovulation prediction output based on said ovulation data transform comprises the step of automatically computer analyzing a succession of adjacent transformed estimated effective daily zenith created values to determine a dip in said transformed estimated effective daily zenith created values.

333. A process for improved reliability notification of an ovulation event for a user as described in clause 331, or any other clause, wherein said step of generating a transformed ovulation prediction output based on said ovulation data transform comprises the step of automatically computer analyzing a succession of adjacent transformed estimated effective daily zenith created values to determine a dip in said transformed estimated effective daily zenith created values.

334. A process for improved reliability notification of an ovulation event for a user as described in clause 333, or any other clause, wherein said step of automatically determining whether said transformed ovulation prediction output or said varied transform ovulation prediction output is likely to provide a more user-preference aligned indication of the likely existence of an ovulation event comprises the step of automatically applying said transformed ovulation prediction output and said varied transform ovulation prediction output to a plurality of ovulation events.

335. A process for improved reliability notification of an ovulation event for a user as described in clause 334, or any other clause, wherein said step of automatically applying said transformed ovulation prediction output and said varied transform ovulation prediction output to a plurality of ovulation events comprises the step of automatically applying said transformed ovulation prediction output and said varied transform ovulation prediction output to a many user composite database.

336. A process for improved reliability notification of an ovulation event for a user as described in clause 334, or any other clause, wherein said step of automatically applying said transformed ovulation prediction output and said varied transform ovulation prediction output to a plurality of ovulation events comprises the step of automatically applying said transformed ovulation prediction output and said varied transform ovulation prediction output to a then-available many user composite database.

337. A computerized improved reliability ovulation notification system comprising:
- a periodic capture internal body temperature sensor for placement in contact with a woman's body;
- a computer data input from said periodic capture internal body temperature sensor;
- at least one computer processor operated automatic data transform recalculator configured to apply ovulation transformation parameters and coupled to said computer data input;
- an automatic transformed ovulation prediction output responsive to said at least one computer processor operated automatic data transform recalculator;
- an ovulation transformation parameter vary routine to which said at least one computer processor operated automatic data transform recalculator is automatically responsive to apply varied ovulation transformation parameters to create a varied ovulation data transform;
- an automatic varied transform ovulation prediction output generator;
- an automatic transformed ovulation prediction output comparator responsive to said automatic varied transform ovulation prediction output generator configured to assess a plurality of varied transform ovulation prediction outputs and provide a more user-preference aligned indication of the likely existence of an ovulation event; and
- an ovulation transformation parameter memory responsive to said automatic transformed ovulation prediction output comparator, and configured to store revised ovulation transformation parameters that provide said more user-preference aligned indication of the likely existence of an ovulation event for future use.

338. A computerized improved reliability ovulation notification system as described in clause 337, or any other clause, wherein said at least one computer processor operated automatic data transform recalculator configured to apply ovulation transformation parameters comprises at least one computer processor operated automatic data transform recalculator configured to apply revised ovulation transformation parameters in response to said automatic transformed ovulation prediction output comparator.

339. A computerized improved reliability ovulation notification system as described in clause 338, or any other clause, wherein said at least one computer processor operated automatic data transform recalculator configured to apply revised ovulation transformation parameters comprises at least one computer processor operated automatic data transform recalculator configured to cumulatively apply revised ovulation transformation parameters.

340. A computerized improved reliability ovulation notification system as described in clause 337, or any other clause, wherein said ovulation transformation parameter vary routine comprises an ovulation transformation parameter vary routine configured to vary at least one previously varied ovulation transformation parameter.

341. A computerized improved reliability ovulation notification system as described in clause 337, or any other clause, wherein said ovulation transformation parameter vary routine comprises a cumulative ovulation transformation parameter vary routine.

342. A computerized improved reliability ovulation notification system as described in clause 337, or any other clause, and further comprising a user-preference input to which said automatic transformed ovulation prediction output comparator is responsive.

343. A computerized improved reliability ovulation notification system as described in clause 337, or any other clause, wherein said at least one computer processor operated automatic data transform recalculator configured to apply ovulation transformation parameters and coupled to said computer data input comprises a plurality of computer processor operated automatic data transform recalculators, each configured to apply variable ovulation transformation parameters.

344. A computerized improved reliability ovulation notification system as described in clause 343, or any other clause, and further comprising an automatic transform recalculator combiner responsive to said plurality of computer processor operated automatic data transform recalculators and to which said automatic varied transform ovulation prediction output generator is responsive.

345. A computerized improved reliability ovulation notification system as described in clause 343, or any other clause, wherein at least two of plurality of computer processor operated automatic data transform recalculators are utilized by said automatic varied transform ovulation prediction output generator.

346. A computerized improved reliability ovulation notification system as described in clause 343, or any other clause, wherein said ovulation transformation parameter vary routine comprises an ovulation transformation range size vary routine.

347. A computerized improved reliability ovulation notification system as described in clause 337, or any other clause, wherein said ovulation transformation parameter vary routine comprises an ovulation transformation range drift vary routine.

348. A computerized improved reliability ovulation notification system as described in clause 337, or any other clause, wherein said ovulation transformation parameter vary routine comprises an ovulation transformation threshold inclusion vary routine.

349. A computerized improved reliability ovulation notification system as described in clause 337, or any other clause, wherein said ovulation transformation parameter vary routine comprises an ovulation transformation coefficient vary routine.

350. A computerized improved reliability ovulation notification system as described in clause 337, or any other clause, wherein said ovulation transformation parameter vary routine comprises an ovulation transformation weight vary routine.

351. A computerized improved reliability ovulation notification system as described in clause 342, or any other clause, wherein said ovulation transformation parameter vary routine comprises a plurality of ovulation transformations weight vary routines, each of said plurality of ovulation transformations weight vary routines, configured to vary a weight for one of said plurality of computer processor operated automatic data transform recalculators.

352. A computerized improved reliability ovulation notification system as described in clause 337, or any other clause, and further comprising a user-condition input to which said automatic transformed ovulation prediction output comparator is responsive.

353. A computerized improved reliability ovulation notification system as described in clause 352, or any other clause, wherein said user-condition input comprises a user-condition input selected from a group consisting of:
a prior period computer input;
a luteinizing hormone test computer input;
a fertility test result computer input;
a user data computer input;
a user menstrual cycle computer input;
a user body type computer input;
a user physical condition computer input;
a user medical history computer input;
a user text message computer input; and
a plurality of many user inputs to a computer.

354. A computerized improved reliability ovulation notification system as described in clause 337, or any other clause, and further comprising a many user composite computer data input and wherein said automatic transformed ovulation prediction output comparator is configured to be responsive to said many user composite computer data input.

355. A computerized improved reliability ovulation notification system as described in clause 354, or any other clause, wherein said many user composite computer data input comprises a demographically grouped many user composite computer data input.

356. A computerized improved reliability ovulation notification system as described in clause 355, or any other clause, wherein said demographically grouped many user composite computer data input comprises a demographically grouped many user composite computer data input selected from a group consisting of:
an age grouped many user composite computer data input;
an ethnically grouped many user composite computer data input;
a prior pregnancy grouped many user composite computer data input;
a medication-taken grouped many user composite computer data input;
a physical activity grouped many user composite computer data input;
a physical condition grouped many user composite computer data input;
a pre-existing medical condition grouped many user composite computer data input.

357. A computerized improved reliability ovulation notification system as described in clause 355, or any other clause, and further comprising a minimum error value calculator to which said automatic transformed ovulation prediction output comparator is responsive.

358. A computerized improved reliability ovulation notification system as described in clause 357, or any other clause, wherein said minimum error value calculator comprises a minimum least squares value calculator.

259. A computerized improved reliability ovulation notification system as described in clause 337, or any other clause, wherein said at least one computer processor operated automatic data transform recalculator comprises an estimated daily zenith automatic data transform recalculator.

360. A computerized improved reliability ovulation notification system as described in clause 359, or any other clause, wherein said estimated daily zenith automatic data transform recalculator comprises a running average value estimated daily zenith automatic data transform recalculator.

361. A computerized improved reliability ovulation notification system as described in clause 359, or any other clause, and further comprising an automatic estimated daily zenith dip calculator responsive to said running average value estimated daily zenith automatic data transform recalculator.

362. A computerized improved reliability ovulation notification system as described in clause 360, or any other clause, and further comprising an automatic estimated daily zenith dip calculator responsive to said running average value estimated daily zenith automatic data transform recalculator.

363. A computerized improved reliability ovulation notification system as described in clause 337, or any other clause, wherein said automatic transformed ovulation prediction output comparator comprises a plurality of ovulation events prediction output comparator.

364. A computerized improved reliability ovulation notification system as described in clause 363, or any other clause, and further comprising a many user composite database to which said plurality of ovulation events prediction output comparator is responsive.

As can be easily understood from the foregoing, the basic concepts of the present invention may be embodied in a variety of ways. It involves both vaginal temperature sensing techniques as well as devices to accomplish the appropriate temperature sensing. In this application, the temperature-related techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this non-provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sensor" should be understood to encompass disclosure of the act of "sensing"—whether explicitly discussed or not— and, conversely, were there effectively disclosure of the act of "sensing", such a disclosure should be understood to encompass disclosure of a "sensor" and even a "means for sensing." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, standards information publication, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Finally, all references listed in the list of references below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

REFERENCES TO BE INCORPORATED BY REFERENCE

I. U.S. Patents

| Pat. No. | Kind Code | Date Issued | Patentee |
| --- | --- | --- | --- |
| 8,496,597 | B2 | 2013 Jul. 30 | James et al. |
| 9,155,522 | B2 | 2015 Oct. 13 | James et al. |
| 9,155,523 | B2 | 2015 Oct. 13 | James et al. |
| 5,406,961 | | 1995 Apr. 18 | Artal |
| 8,715,204 | B2 | 2014 May 6 | Webster et al. |
| 9,314,227 | B2 | 2016 Apr. 19 | Runkewitz et al. |
| D703,319 | S | 2014 Apr. 22 | Ziegner |
| 8,930,147 | B2 | 2015 Jan. 6 | Pollack et al. |
| 6,447,448 | B1 | 2002 Sep. 10 | Ishikawa et al. |

II. U.S. Patent Application Publications

| Publication No. | Kind Code | Date Published | Patentee |
| --- | --- | --- | --- |
| 20160296210 | A1 | 2016 Oct. 13 | Matsushima |
| 20150044398 | A1 | 2015 Feb. 12 | Oguri et al. |
| 20160030011 | A1 | 2016 Feb. 4 | James et al. |
| 20130237771 | A1 | 2013 Sep. 12 | Runkewitz et al. |
| 20130131541 | A1 | 2013 May 23 | Tsai et al. |
| 20090326410 | A1 | 2009 Dec. 31 | James et al. |
| 20140213927 | A1 | 2014 Jul. 31 | Webster et al. |
| 20090296742 | A1 | 2009 Dec. 3 | Sicurello et al. |
| 20090221882 | A1 | 2009 Sep. 3 | Furman |
| 20050288737 | A1 | 2005 Dec. 29 | Feliss et al. |
| 20100004707 | A1 | 2010 Jan. 7 | Hochman et al. |
| 20090270948 | A1 | 2009 Oct. 29 | Nghiem et al. |
| 20100274105 | A1 | 2010 Oct. 28 | Rosenshein |
| 20100036208 | A1 | 2010 Feb. 11 | Koh et al. |
| 20140104059 | A1 | 2014 April | Tran |
| 2007059761 | A2 | 2007 May 31 | Alexander et al. |
| 2004058999 | A2 | 2004 Jul. 15 | Zimmermann et al. |

III. Foreign Patent Documents

| Patent No. | Kind Code | Country Code | Date Issued | Patentee |
| --- | --- | --- | --- | --- |
| 2567680 | B1 | EP | 2016 Mar. 23 | Runkewitz et al. |
| 1636594 | B1 | EP | 2011 Aug. 24 | Alexander et al. |
| 1579007 | B1 | EP | 2015 May 27 | Zimmermann et al. |
| 19943456 | B4 | DE | 2005 Oct. 20 | Zosel et al. |
| 10345282 | B3 | DE | 2005 Apr. 14 | Zosel et al. |
| 0424102 | B1 | EP | 1998 Dec. 2 | Nishitomo Co. Ltd. |

IV. Non Patent Literature

WIKIPEDIA, Artificial neural network,
https://en.wikipedia.org/wiki/Artificial_neural_network, Jun. 12, 2018, 40 pages
https://www.ovularing.com, Shop-OvulaRing, 2 pages
Rodrigues, Intra-Body Sensor for Vaginal Temperature Monitoring. Open Access; Sensors ISSN: 1424-8220; 2009. 12 pages Machine Translated version of DE 10345282. Machine translation was provided by espace.net on Dec. 17, 2013
U.S. Non-Provisional Application No. 13/182,565, filed Jul. 14, 2011, entitled "Wireless Vagina Sensor Probe", entire Image File Wrapper available on USPTO PAIRS
U.S. Provisional application No. 61/364,034, filed Jul. 14, 2010, entitled "Wireless Vagina Sensor Probe', entire Image File Wrapper available on USPTO PAIR
U.S. Provisional Application No. 62/287,806, filed Jan. 27, 2016, entitled "User-Enhanced Body Temperature Sensing Device", entire Image File Wrapper available via USPTO PAIR
U.S. Non-Provisional Application No. 14/253,560, filed Apr. 15, 2014, entitled "Physiologic Change Sensor Probe", entire Image File Wrapper available on USPTO PAIRS
U.S. Non-Provisional Application No. 14/253,560, filed Apr. 15, 2014, entitled "Physiologic Change Sensor Probe", Office Action dated Jun. 20, 2014, 14 pages.
U.S. Non-Provisional Application No. 14/253,560, filed Apr. 15, 2014, entitled "Physiologic Change Sensor Probe", Office Action dated Dec. 22, 2014, 13 pages.
U.S. Non-Provisional Application No. 14/253,560, filed Apr. 15, 2014, entitled "Physiologic Change Sensor Probe", Office Action dated Jan. 25, 2016, 14 pages.
U.S. Non-Provisional Application No. 13/021,806, filed Feb. 7, 2011, entitled "Multi-Sensor Patch and Systems", entire Image File Wrapper available on USPTO PAIRS
U.S. Non-Provisional Application No. 13/021,806, filed Feb. 7, 2011, entitled "Multi-Sensor Patch and Systems", Office Action dated May 9, 2014; 7 pages.
U.S. Non-Provisional Application No. 13/182,565, filed Jul. 14, 2011, entitled "Wireless Vagina Sensor Probe", Office Action dated May 24, 2013; 13 pages.
Goodfellow, et al., Deep Learning. The MIT Press (10 Nov. 2016). ASIN: B01MRVFGX4.
ISO Standard 8009 (2014) "Mechanical contraceptives -- Reusable natural and silicone rubber contraceptive diaphragms -- Requirements and tests."
ISO 8009 (2004).

Thus, the applicant(s) should be understood to have support to claim and make a statement of invention to at least: i) each of the vaginal temperature sensing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

In addition and as to computer aspects and each aspect amenable to programming or other electronic automation, it should be understood that in characterizing these and all other aspects of the invention—whether characterized as a device, a capability, an element, or otherwise, because all of these can be implemented via software, hardware, or even firmware structures as set up for a general purpose computer, a programmed chip or chipset, an ASIC, application specific controller, subroutine, or other known programmable or circuit specific structure—it should be understood that all such aspects are at least defined by structures including, as person of ordinary skill in the art would well recognize: hardware circuitry, firmware, programmed application specific components, and even a general purpose computer programmed to accomplish the identified aspect. For such items implemented by programmable features, the applicant(s) should be understood to have support to claim and make a statement of invention to at least: xv) processes performed with the aid of or on a computer, machine, or computing machine as described throughout the above discussion, xvi) a programmable apparatus as described throughout the above discussion, xvii) a computer readable memory encoded with data to direct a computer comprising means or elements which function as described throughout the above discussion, xviii) a computer, machine, or computing machine configured as herein disclosed and described, xix) individual or combined subroutines and programs as herein disclosed and described, xx) a carrier medium carrying computer readable code for control of a computer to carry out separately each and every individual and combined method described herein or in any claim, xxi) a computer program to perform separately each and every individual and combined method disclosed, xxii) a computer program containing all and each combination of means for performing each and every individual and combined step disclosed, xxiii) a storage medium storing each computer program disclosed, xxiv) a signal carrying a computer program disclosed, xxv) a processor executing instructions that act to achieve the steps and activities detailed, xxvi) circuitry configurations (including configurations of transistors, gates, and the like) that act to sequence and/or cause actions as detailed, xxvii) computer readable medium(s) storing instructions to execute the steps and cause activities detailed, xxviii) the related methods disclosed and described, xxix) similar, equivalent, and even implicit variations of each of these systems and methods, xxx) those alternative designs which accomplish each of the functions shown as are disclosed and described, xxxi) those alternative designs and methods which accomplish each of the functions shown as are implicit to accomplish that which is disclosed and described, xxxii) each feature, component, and step shown as separate and independent inventions, and xxxiii) the various combinations of each of the above and of any aspect, all without limiting other aspects in addition.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims. Note that the term "configured to" (or related versions thereof) implies that the referenced componentry is designed, including, e.g., arranged, manufactured, programmed, prepared, and/or positioned, to achieve the indicated capability, whether via use of particular subcomponent(s), arrangements thereof, or via other ways.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A user friendly vaginal temperature sensor system comprising:
    a flexible outer ring shell made of a cured, non-transparent material;
    a window in said flexible outer ring shell; and
    electrical componentry established within said flexible outer ring shell, comprising:
        at least one battery;
        vaginal temperature sensor componentry electrically responsive to said at least one battery;
        sensed vaginal temperature transmission componentry electrically responsive to said at least one battery;
        a visually sense-able, battery power-on indicator electrically responsive to said at least one battery; and
        a timer configured to start a countdown of a time period in response to said start of said use of said battery power; and
        user-initiated device activation componentry configured with a type of redundant protection against unintentional initiation of said use of battery power;
    wherein said user-initiated device activation componentry is further configured to allow a start use of battery power upon occurrence of an event that has a higher probability of being user-initiated and of being intended by said user to initiate said use of said battery power;
    wherein said redundant protection is configured to terminate said use of said battery power in the event of non-occurrence of establishment of a communication link between said system and a different electronic device before the expiration of said time period; and wherein said window is filled with transparent material and positioned so that light from said visually sense-able; battery power-on indicator passes through said window to outside of said flexible ring.

2. A user friendly vaginal temperature sensor system as described in claim 1 wherein said user-initiated device activation componentry comprises a user-operable switch.

3. A user friendly vaginal temperature sensor system as described in claim 1 wherein said user-operable switch comprises a compression switch.

4. A user friendly vaginal temperature sensor system as described in claim 1 wherein said transparent material allows sufficient light therethrough so that said light can be visually sensed by a user holding said vaginal temperature sensor apparatus.

5. A user friendly vaginal temperature sensor system comprising:
a flexible outer ring shell;
at least one battery established within said flexible outer ring shell;
vaginal temperature sensor componentry established within said flexible outer ring shell;
sensed vaginal temperature transmission componentry established within said flexible outer ring shell;
visually sense-able, battery power-on indicator electrically responsive to said at least one battery;
user-initiated device activation componentry comprising a user-operable switch to which power from said at least one battery is electrically responsive, and configured to start use of battery power upon user operation of said user-operable switch; and
a timer configured to start a countdown of a time period in response to said start of said use of said battery power,
wherein said apparatus is configured to terminate said use of said battery power in the event of non-occurrence of establishment of a communication link between said apparatus and a different electronic device before the expiration of said time period.

6. A user friendly vaginal temperature sensor system as described in claim 5 wherein said user-operable switch comprises a compression switch.

7. A user friendly vaginal temperature sensor system as described in claim 6 wherein said flexible outer ring shell comprises cured non-transparent material configured and arranged so as to prevent visual recognition of said user-initiated device activation componentry, of said timer, and of said vaginal temperature sensor componentry but not of said visually sense-able, battery power-on indicator.

8. A user friendly vaginal temperature sensor system as described in claim 7 wherein said flexible ring further comprises a cured, transparent material filled window positioned so that light from said visually sense-able, battery power-on indicator passes through said cured, transparent material filled window to outside of said vaginal temperature sensor apparatus.

9. A user friendly vaginal temperature sensor system as described in claim 8 wherein said cured, transparent material of said cured; transparent material filled window allows sufficient light through said cured, transparent material filled window so that said light from said visually sense-able, battery power-on indicator can be visually sensed by a user holding said vaginal temperature sensor apparatus.

10. A user friendly vaginal temperature sensor system as described in claim 9 wherein said cured, transparent material fills voids between said flexible outer ring shell and said vaginal temperature sensor componentry, said at least one battery, and said user-initiated device activation componentry.

11. A user friendly vaginal temperature sensor system as described in claim 10 wherein said cured, non-transparent material has a higher tensile strength than does said cured, transparent material, said system further comprising a computer processor operated ovulation transformation parameter vary routine responsive to said vaginal temperature sensor componentry.

12. A user friendly vaginal temperature sensor system comprising:
a cured, non-transparent, flexible outer ring shell made of cured, non-transparent material;
vaginal temperature sensor componentry established within said cured, non-transparent, flexible outer ring shell;
at least one battery established within said cured, non-transparent, flexible outer ring shell;
a visually sense-able, battery power-on indicator electrically responsive to said at least one battery; and
user-initiated device activation componentry;
wherein said cured non-transparent material is configured and arranged so as to prevent visual recognition, by a user, of said vaginal temperature sensor componentry, and said at least one battery, but not of said visually sense-able, battery power-on indicator,
said system further comprising a window in said cured, non-transparent, flexible outer ring shell, said window positioned, and filled with cured, transparent material, so that light from said visually sense-able, battery power-on indicator passes through said window to outside of said cured; non-transparent, flexible outer ring shell.

13. A user friendly vaginal temperature sensor system as described in claim 12 and further comprising:
a temperature sensor;
an antenna;
a microprocessor;
a data transmitter; and
a signal receiver.

14. A user friendly vaginal temperature sensor system as described in claim 12 wherein said user-initiated device activation componentry is configured with redundant protection against unintentional initiation of use of battery power, and wherein said user-initiated device activation componentry is further configured to allow a start of said use of battery power upon occurrence of an event that has a higher probability of being user-initiated and of being intended by said user to initiate said use of said battery power.

15. A user friendly vaginal temperature sensor system as described in claim 14 wherein said event user-initiated device activation componentry comprises components external of said cured, non-transparent, flexible outer ring shell.

16. A user friendly vaginal temperature sensor system as described in claim 14 wherein said event comprises a user-caused mechanical action.

17. A user friendly vaginal temperature sensor system as described in claim 16 wherein said user-caused mechanical action comprises switch pressurization.

18. A user friendly vaginal temperature sensor system as described in claim 16 wherein said user-caused mechanical action comprises either device bending or a proximity condition change.

19. A user friendly vaginal temperature sensor system as described in claim 12 wherein said cured, transparent material fills voids between said cured, non-transparent, flexible ring shell and said vaginal temperature sensor componentry, said at least one battery, and said user-initiated device activation componentry.

20. A user friendly vaginal temperature sensor system as described in claim 12 wherein said cured non-transparent material has a higher tensile strength than does said cured, transparent material.

* * * * *